(12) United States Patent
Bossis et al.

(10) Patent No.: US 8,927,269 B2
(45) Date of Patent: Jan. 6, 2015

(54) AVIAN ADENOASSOCIATED VIRUS AND USES THEREOF

(75) Inventors: Ioannis Bossis, Columbia, MD (US); John A. Chiorini, Silver Spring, MD (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 2156 days.

(21) Appl. No.: 10/557,662

(22) PCT Filed: May 18, 2004

(86) PCT No.: PCT/US2004/015534
§ 371 (c)(1),
(2), (4) Date: Dec. 21, 2006

(87) PCT Pub. No.: WO2005/017101
PCT Pub. Date: Feb. 24, 2005

(65) Prior Publication Data
US 2007/0092866 A1    Apr. 26, 2007

Related U.S. Application Data

(60) Provisional application No. 60/472,066, filed on May 19, 2003.

(51) Int. Cl.
| | | |
|---|---|---|
| C12N 15/86 | (2006.01) |
| A61K 48/00 | (2006.01) |
| C12N 7/00 | (2006.01) |
| C12N 15/85 | (2006.01) |
| C12N 15/861 | (2006.01) |
| C07H 21/00 | (2006.01) |
| C07H 21/02 | (2006.01) |
| C07H 21/04 | (2006.01) |
| C07H 19/06 | (2006.01) |
| C07H 19/16 | (2006.01) |
| C07K 14/47 | (2006.01) |
| C07K 14/005 | (2006.01) |
| C07K 14/075 | (2006.01) |

(52) U.S. Cl.
CPC ............ *C12N 15/86* (2013.01); *A61K 48/0091* (2013.01); *C07K 14/005* (2013.01); *C12N 7/00* (2013.01); *C12N 2750/14121* (2013.01); *C12N 2750/14122* (2013.01); *C12N 2750/14143* (2013.01)
USPC ..... 435/320.1; 435/69.1; 435/70.1; 435/70.3; 536/22.1; 536/24.1

(58) Field of Classification Search
None
See application file for complete search history.

(56) References Cited

U.S. PATENT DOCUMENTS

| | | |
|---|---|---|
| 6,146,874 A | 11/2000 | Zolotukhin et al. |
| 6,180,613 B1 | 1/2001 | Kaplitt et al. |
| 6,221,349 B1 | 4/2001 | Couto et al. |
| 6,309,634 B1 | 10/2001 | Bankiewicz et al. |
| 6,391,858 B2 | 5/2002 | Podsakoff et al. |
| 6,468,524 B1 | 10/2002 | Chiorini et al. |
| 6,485,976 B1 | 11/2002 | Nadler et al. |
| 6,855,314 B1 | 2/2005 | Chiorini et al. |
| 6,984,517 B1 | 1/2006 | Chiorini et al. |
| 2002/0076754 A1 | 6/2002 | Sun et al. |
| 2003/0228282 A1 | 12/2003 | Gao et al. |
| 2004/0086490 A1 | 5/2004 | Chiorini et al. |
| 2004/0110266 A1 | 6/2004 | Chiorini et al. |
| 2004/0115789 A1 | 6/2004 | Meruelo et al. |
| 2005/0255089 A1 | 11/2005 | Chiorini et al. |

FOREIGN PATENT DOCUMENTS

| | | | |
|---|---|---|---|
| DE | 44 36 664 A1 | 7/1996 | |
| EP | 1 310 571 | 5/2003 | |
| WO | WO 93/24641 A | 12/1993 | |
| WO | WO 95/11997 A | 5/1995 | |
| WO | WO 96/00587 A | 1/1996 | |
| WO | WO 96/15777 A | 5/1996 | |
| WO | WO 96/18727 | 6/1996 | |
| WO | WO 97/06272 | 2/1997 | |
| WO | WO 98/11244 A | 3/1998 | |
| WO | WO 98/41240 A | 9/1998 | |
| WO | WO 98/45462 A | 10/1998 | |
| WO | WO 99/18227 | * 4/1999 | ............. C12N 15/86 |
| WO | WO 99/61601 A | 12/1999 | |
| WO | WO 00/26254 | 5/2000 | |
| WO | WO 00/28061 | 5/2000 | |
| WO | WO 01/70276 A | 9/2001 | |
| WO | WO 01/83692 | 11/2001 | |
| WO | WO 03/093479 | 11/2003 | |
| WO | WO 2004/112727 A | 12/2004 | |
| WO | WO 2005/056807 A | 6/2005 | |
| WO | WO 2006/029196 | 3/2006 | |
| WO | WO 2006/119432 | 11/2006 | |

OTHER PUBLICATIONS

Bauer et al (Virology, 1993. vol. 193, pp. 478-482).*
Hess et al (Arch. Virol. 1995, vol. 140, pp. 591-598).*
Estevez et al (Poultry Science, 2002. vol. 81, supplement 1, p. 164).*
Bauer et al., "Herpesviruses Provide Helper Functions for Avian Adeno-associated Parvovirus" 67 Journal of General Virology 181-185 (1986).*
Alexander et al., "DNA-Damaging Agents Greatly Increase the Transduction of Nondividing Cells by Adeno-Associated Virus Vectors," Dec. 1994, *J. Virol.*, 68(12):8282-8287.
Alisky et al., "Transduction of Murine Cerebellar Neurons with Recombinant FIV and AAV5 Vectors," Aug. 2000, *Mol. Neurosci.*, 11(1221):2669-2673.

(Continued)

*Primary Examiner* — Celine Qian
*Assistant Examiner* — Nancy J Leith
(74) *Attorney, Agent, or Firm* — Sheridan Ross P.C.

(57) ABSTRACT

The present invention provides an Avian adeno-associated virus (AAAV) virus and vectors and particles derived therefrom. In addition, the present invention provides methods of delivering a nucleic acid to a cell using the AAAV vectors and particles. Methods of isolating the AAAV are provided.

21 Claims, 22 Drawing Sheets

(56) References Cited

OTHER PUBLICATIONS

Alisky J.M. And Tolbert D.M., "Differential labeling of converging afferent pathways using biotinylated dextran amine and cholera toxin subunit B," 1994, *Journal of Neuroscience Methods*, 52:143-148.
Allen, J.M., Halbert, C.L. and Miller, A.D., "Improved adeno-associated virus vector production with transfection of a single helper adenovirus gene, E4orf6," 2000, *Mol Ther*, 1:88-95.
Arnberg, N., A. H. Kidd, K. Edlund, J. Nilsson, P. Pring-Akerblom, and G. Wadell, "Adenovirus type 37 binds to cell surface sialic acid through a charge-dependent interaction," 2002, *Virology*, 302:33-43.
Atchison, R. W., B. C. Casto, and W. M. Hammon, "Adenovirus-Associated Defective Virus Particles," 1965, *Science*, 149:754-756.
Auricchio et al., "A Single-Step Affinity Column for Purification of Serotype-5 Based Adeno-Associated Viral Vectors," Oct. 2001, *Mol Ther*, 4(4):372-374.
Bachmann, P.A., M.D. Hoggan, E. Kurstak, J.L. Melnick, H.G. Pereira, P. Tattersall, and C. Vago, Parvoviridae: second report, 1979, *Interverology*, 11:248-254.
Bajocchi G, Feldman SH, Crystal RG, Mastrangeli A., "Direct in vivo gene transfer to ependymal cells in the central nervous system using recombinant adenovirus vectors," 1993, *Nat Genet*, 3:229-234.
Bantel-Schaal U, Delius H, Schmidt R, zur Hausen H., "Human adeno-associated virus type 5 is only distantly related to other known primate helper-dependent parvoviruses," 1999, *J Virol.*, 73(2):939-947.
Bantel-Schaal U, zur Hausen H., "Characterization of the DNA of a defective human parvovirus isolated from a genital site," 1984, *Virology*, 134(1):52-63, XP009028974.
Bantel-Schaal, U. and M. Stohr, "Influence of adeno-associated virus on adherence and growth properties of normal cells," 1992, *J. Virol.*, 66:773-779.
Bantel-Schaal, U., Hub, B. and Kartenbeck, J., "Endocytosis of adeno-associated virus type 5 leads to accumulation of virus particles in the Golgi compartment," 2002, *J Virol*, 76:2340-2349.
Bartlett JS, Kleinschmidt J., Boucher RC and Samulski RJ, "Targeted adeno-associated virus vector transduction of nonpermissive cells mediated by a bispecific F(ab'gamma)$_2$ antibody," 1999, *Nat Biotechnol*, 17:181-186.
Bartlett JS, Samulski RJ, McCown TJ., "Selective and rapid uptake of adeno-associated virus type 2 in brain," 1998, *Hum Gene Ther*, 9(8):1181-1186.
Bartlett, J.S., Wilcher, R. and Samulski, R.J., "Infectious entry pathway of adeno-associated virus and adeno-associated virus vectors," 2000, *J Virol*, 74:2777-2785.
Ben-Israel, H. and Kleinberger, T., "Adenovirus and cell cycle control," 2002, *Front Biosci*, 7:d1369-1395.
Bergelson, JM, Cunningham JA, Droguett G., Kurt-Jones EA, Krithivas A., Hong JS, Horwitz MS, Crowell RL, and Finberg RW, "Isolation of a common receptor for Coxsackie B viruses and adenoviruses 2 and 5," 1997, *Science*, 275:1320-1323.
Berns, K. I., "Parvoviridae: the viruses and their replication," *In* F. B. N., K. D. M., and H. P. M. (ed.), *Fields virology*, 3rd ed. Lippincott-Raven Publishers, Philadelphia, PA, p. 2173-2197, 1996.
Blacklow, et al., "Serologic Evidence for Human Infection With Adenovirus-Associated Viruses," 1968, *J NCI*, 40(2):319-327.
Blacklow, N.R., Hoggan, M.D. and Rowe, W.P. "Isolation of adenovirus-associated viruses from man," 1967, *Proc Natl Acad Sci U S A*,58:1410-1415.
Bomsel M, Alfsen A, "Entry of viruses through the epithelial barrier: pathogenic trickery," 2003, *Nat Rev Mol Cell Biol*, 4:57-68.
Bomsel M, David V, "Mucosal gatekeepers: selecting HIV viruses for early infection," 2002, *Nat Med*, 8:114-116.8
Bossis, I. And Chiorini, J.A., "Cloning of an Avian Adeno-Associated Virus (AAAV) and Generation of Recombinant Aaav Particles," 2003, *J Virol*, 77(12):6799-6810.
Burcin, M.M., O'Malley, B.W. And S.Y. Tsai, "A regulatory system for target gene expression," 1998, *Frontiers in Bioscience*, 3:c1-7.
Carter, B. J., B. A. Antoni, and D. F. Klessig, "Adenovirus containing a deletion of the early region 2A gene allows growth of adeno-associated virus with decreased efficiency," 1992, *Virology*, 191:473-476.
Carter, B. J., C. A. Laughlin, L. M. de la Maza, and M. Myers, "Adeno-associated virus autointerference," 1979, *Virology*, 92:449-462.
Casto, B. C., R. W. Atchison, and W. M. Hammon, "Studies on the relationship between adeno-associated virus type I (AAVC-1) and adenoviruses. I. Replication of AAV-1 in certain cell cultures and its effect on helper adenovirus," 1967a, *Virology*, 32:52-59.
Casto, B. C., J. A. Armstrong, R. W. Atchison, and W. M. Hammon, "Studies on the relationship between adeno-associated virus type 1 (AAV-1) and adenoviruses. II. Inhibition of adenovirus plaques by AAV; its nature and specificity," 1967b, *Virology*, 33:452-458.
Chang, L.S. and Shenk, T., "The adenovirus DNA-binding protein stimulates the rate of transcription directed by adenovirus and adeno-associated virus promoters," 1990, *J Virol*, 64:2103-2109.
Chang, L.S., Y. Shi, and T. Shenk, "Adeno-associated virus P5 promoter contains an adenovirus E1A-inducible element and a binding site for the major late transcription factor,"1989, *J. Virol.*, 63:3479-3488.
Chao H et al., "Several Log Increase in Therapeutic Transgene Delivery by Disticnt Adeno-Associated Viral Serotype Vectors," 2000, *Molecular Therapy*, 2(6):619-623.
Chejanovsky, N. and B.J. Carter, "Replication of a human parvovirus nonsense mutant in mammalian cells containing an inducible amber suppressor," 1989a, *Virology*, 171:239-247.
Chejanovsky, N. and B.J. Carter, "Mutagenesis of an AUG codon in the adeno-associated virus rep gene: effects on viral DNA replication," 1989b, *Virology*, 173:120-128.
Chiorini et al. "Cloning of Adeno-Associated Virus Type 4 (AAV4) and Generation of Recombinant AAV4 Particles" Sep. 1997, *J. Virol.*, 71(9):6823-6833, XP002058635.
Chiorini JA, Afione S, Kotin RM, "Adeno-associated virus (AAV) type 5 Rep protein cleaves a unique terminal resolution site compared with other AAV serotypes," 1999a May, *J Virol.*, 73(5):4293-4298.
Chiorini JA, Kim F, Yang L, Kotin RM, "Cloning and characterization of adeno-associated virus type 5," 1999b, Feb., *J Virol.*, 73(2):1309-1319, XP-002125035.
Chiorini, J.A., C.M. Wendtner, E. Urcelay, B. Safer, M. Hallek, and R.M. Kotin, "High-efficiency transfer of the T cell co-stimulatory molecule B7-2 to lymphoid cells using high-titer recombinant adeno-associated virus vectors,"1995, *Human Gene Therapy*, 6:1531-1541.
Chiorini, J.A., L. Yang, B. Safer, and R.M. Kotin, "Determination of adeno-associated virus Rep68 and Rep78 binding sites by random sequence oligonucleotide selection," 1995, *J. Virol.*, 69:7334-7338.
Chiorini, J.A., M.D. Weitzman, R.A. Owens, E. Urcelay, B. Safer, and R.M. Kotin, "Biologically active Rep proteins of adeno-associated virus type 2 produced as fusion proteins in *Escherichia coli*," 1994a, *J. Virol.*, 68:797-804.
Chiorini, J.A., S.M. Wiener, R.M. Kotin, R.A. Owens, SRM Kyöstiö, and B. Safer, "Sequence requirements for stable binding and function of Rep68 on the adeno-associated virus type 2 inverted terminal repeats,"1994b, *J. Virol.*, 68:7448-7457.
Clark et al., "Highly Purified Recombinant Adeno-Associated Virus Vectors are Biologically Active and Free of Detectable Helper and Wild-Type Viruses," 1999, *Hum. Gene Ther.*, 10:1031-1039.
Cohen-Salmon et al., "Targeted ablation of connexin26 in the inner ear epithelial gap junction network causes hearing impairment and cell death," 2002, *Curr Biol*, 12:1106-1111.
Coria et al., "Isolation and identification of a bovine adenovirus type 3 with an adenovirus-associated virus", 1978, *American Journal of Veterinary Research*, 39(12):1904-1906, XP009050511.
Crystal RG, "Transfer of genes to humans: early lessons and obstacles to success," 1995, *Science*, 270(5235):404-410.
Database EMBL, Entry GGACTAA, GenBank Accession No. M61166, Mar. 27, 1991, XP002125220.
Davidson BL, Doran SE, Shewach DS, Latta JM, Hartman JW, Roessler BJ., "Expression of *Escherichia coli* beta-galactosidase and rat HPRT in the CNS of *Macaca mulatta* following adenoviral mediated gene transfer,"1994, *Exp Neurol*, 125:258-267.
Davidson BL, Stein CS, Heth JA, Martins I, Kotin RM, Derksen TA, Zabner J, Ghodsi A, Chiorini JA, "Recombinant adeno-associated virus type 2, 4, and 5 vectors: Transduction of variant cell types and regions in the mammalian central nervous system," 2000, *Proc Natl Acad Sci U S A.*, 97(7):3428-3432.

(56) References Cited

OTHER PUBLICATIONS

Deonarain MP, "Ligand-targeted receptor-mediated vectors for gene delivery," 1998, *Molecular Conjugate Vectors*, 8(1):53-69.
Derby, M. L., M. Sena-Esteves, et al., "Gene transfer into the mammalian inner ear using HSV-1 and vaccinia virus vectors," 1999, *Hear Res*, 134(1-2):1-8.
Di Pasquale, G., Rzadzinska, A., Schneider, M.E., Bossis, I., Chiorini, J.A., Kachar, B., "A novel bovine virus efficiently transduces inner ear neuroepithelial cells," 2005, *Molecular Therapy*, Academic Press, 11(6):849-855, XP004908862.
Di Pasquale, G., and J. A. Chiorini, "PKA/PrKX activity is a modulator of AAV/adenovirus interaction," 2003, *EMBO J*, 22:1716-1724.
Di Pasquale, G., B. L. Davidson, et al., "Identification of PDGFR as a receptor for AAV-5 transduction," 2003, *Nat Med*, 9(10):1306-1312.
Dixit, M., M.S. Webb, W.C. Smart, and S. Ohi," Construction and expression of a recombinant adenoassociated virus that harbors a human *beta*-globin-encoding cDNA," 1991, *Gene*, 104:253-257.
Doll RF, Crandall JE, Dyer CA, Aucoin JM, Smith FI., "Comparison of promoter strengths on gene delivery into mammalian brain cells using AAV vectors," 1996, *Gene Ther*, 3:437-447.
Duan, D., Yue Y., Yan Z., McCray PBJr, and Engelhardt JF., "Polarity influences the efficiency of recombinant adenoassociated virus infection in differentiated airway epithelia," 1998, *Hum Gene Ther*, 9:2761-2776.
During MJ, Symes CW, Lawlor PA, Lin J, Dunning J, Fitzsimons HL, Poulsen D, Leone P, Xu R, Dicker BL, Lipski J, Young D, "An oral vaccine against NMDAR1 with efficacy in experimental stroke and epilepsy," 2000, *Science*, 287:1453-1460.
During MJ, Xu R, Young D, Kaplitt MG, Sherwin RS, Leone P., "Peroral gene therapy of lactose intolerance using an adeno-associated virus vector," 1998, *Nat Med*, 4(10):1131-1135.
During MJ, Leone P, "Adeno-associated virus vectors for gene therapy of neurodegenerative disorders," 1995-96, *Clin Neurosci*, 3(5):292-300, XP-002125034.
Erles, K., Sebokova, P. and Schlehofer, J.R., "Update on the prevalence of serum antibodies (IgG and IgM) to adeno-associated virus (AAV)," 1999, *J Med Virol*, 59:406-411.
Fan D-S, Ogawa M, Fujimoto K-I, Ikeguchi K, Ogasawara Y, Urabe M, Nishizawa M, Nakano I, Yoshida M, Nagatsu I, Ichinose H, Nagatsu T, Kurtzman Gj, Ozawa K, "Behavioral recovery in 6-hydroxydopamine-lesioned rats by cotransduction of striatum with tyrosine hydroxylase and aromatic L-amino acid decarboxylase genes using two separate adeno-associated virus vectors," 1998, *Hum Gene Ther*, 9:2527-2535.
Fisher, Kj, Jooss K., Alston J., Yang Y., Haecker SE, High K., Pathak R. Raper SE, and Wilson JM, "Recombinant adeno-associated virus for muscle directed gene therapy," 1997, *Nat Med*, 3:306-312.
Fisher, R.E., H.D. Mayor, "The evolution of defective and autonomous parvoviruses," 1991, *J Theor Biol*, 149:429-439.
Flannery et al., "Efficient Photoreceptor-targeted Gene Expression in vivo by Recombinant Adeno-Associated Virus," 1997, *Proc Natl Aced Sci USA*, 94:6916-6921.
Flotte TR, Solow R, Owens RA, Afione S, Zeitlin PL, Carter BJ, "Gene expression from adeno-associated virus vectors in airway epithelial cells," 1992, *Am J Respir Cell Mol Biol*, 7(3):349-356; XP000609213.
Flotte, T.R., S.A. Afione, C. Conrad, S.A. McGrath, R. Solow, H. Oka, P.L. Zeitlin, W.B. Guggino, and B.J. Carter, "Stable in vivo expression of the cystic fibrosis transmembrane conductance regulator with an adeno-associated virus vector," 1993, *Proc. Natl. Acad. Sci.*, 90:10613-10617.
Flotte, T.R., S.A. Afione, R. Solow, M.L. Drumm, D. Markakis, W.B. Guggino, P.L. Zeitlin, and B.J. Carter, "Expression of the cystic fibrosis transmembrane conductance regulator from a novel adeno-associated virus promoter," 1993, *J Biol Chem*, 268:3781-3790.
Frolenkov Gi, Belyantseva IA, Friedman TB, Griffith AJ, "Genetic insights into the morphogenesis of inner ear hair cells," 2004, *Nat Rev Genet*, 5:489-498.
Gao, G., L. H. Vandenberghe, M. R. Alvira, Y. Lu, R. Calcedo, X. Zhou, and J. M. Wilson, "Clades of Adeno-associated viruses are widely disseminated in human tissues," 2004, *J Virol*, 78:6381-6388.
Gao, G.P., Alvira, M.R., Wang, L., Calcedo, R., Johnston, J. And Wilson, J.M., "Novel adeno-associated viruses from rhesus monkeys as vectors for human gene therapy," 2002, *Proc Natl Aced Sci USA*, 99:11854-11859.
GenBank Accession No. AY186198, 2003.
Georg-Fries B, Biederlack S, Wolf J, zur Hausen H, "Analysis of proteins, helper dependence, and seroepidemiology of a new human parvovirus," 1984, *Virology*, 134(1):64-71, XP002027460.
Ghodsi A., Stein C., Derksen T., Martins I., Anderson RD, & Davidson BL, "Systemic hyperosmolality improves *beta*-glucuronidase distribution and pathology in murine MPS VII brain following intraventricular gene transfer," 1999, *Exp Neurol*, 160:109-116.
Ghodsi A., Stein, C., Derksen T., Yang, G., Anderson R.D., Davidson B.L., "Extensive beta-glucuronidase activity in murine central nervous system after adenovirus-mediated gene transfer to brain,"1998, *Hum Gene Ther*, 9:2331-2340.
Girod A., Ried M., Wobus C., Lahm H., Leike K., Kleinschmidt J., Deleage G., and Hallek M., "Genetic capsid modifications allow efficient re-targeting of adeno-associated virus type 2," 1999, *Nat Med*, 5:1052-1056.
Grimm, D. And M. A. Kay, "From virus evolution to vector revolution: use of naturally occurring serotypes of adeno-associated virus (AAV) as novel vectors for human gene therapy," 2003, *Curr Gene Ther*, 3(4)::281-304.
Grimm D and Kern A, Rittner K Kleinschmidt JA, "Novel Tools for Production and Purification of Recombinant Adenoassociated Virus Vectors," 1998, *Human Gene Therapy*, 9:2745-2760.
Guy J., Qi X., Muzyczka N., and Hauswirth WW, "Reporter expression persists 1 year after adeno-associated virus-mediated gene transfer to the optic nerve," 1999, *Arch Ophthalmol*, 117:929-937.
Halbert CL, Standaert TA, Aitken ML, Alexander IE, Russell DW, and Miller AD, "Transduction by adeno-associated virus vectors in the rabbit airway: efficiency, persistence, and readministration," 1997, *J. Virol.*, 71:5932-5941.
Halbert, C. L., J. M. Allen, and A. D. Miller, "Adeno-associated virus type 6 (AAV6) vectors mediate efficient transduction of airway epithelial cells in mouse lungs compared to that of AAV2 vectors," 2001, *J Virol*, 75:6615-6624.
He, D. Z., J. Zheng, et al., "Development of acetylcholine receptors in cultured outer hair cells," 2001, *Hear Res*, 162(1-2):113-125.
Hehir K.M., Armentano D., Cardoza L.M., Choquette T.L., Berthelette P.B., White G.A., Couture L.A., Everton M.B., Keegan J., Martin J.M., Pratt D.A., Smith M.P., Smith A.E., Wadsworth S.C., "Molecular characterization of replication-competent variants of adenovirus vectors and genome modifications to prevent their occurrence," 1996, *J Virol*, 70(12):8459-8467.
Heister, T., Heid, I. Ackermann, M., Fraefel, C., "Herpes simplex virus type 1/adeno-associated virus hybrid vectors mediate site-specific integration at the adeno-associated virus preintegration site, AAVS1, on human chromosome 19," 2002, *J Virol*, 76(14):7163-7173.
Hermonat PL, Santin AD, De Greve J, De Rijcke M, Bishop BM, Han L, Mane M, Kokorina N, "Chromosomal latency and expression at map unit 96 of a wild-type plus adeno-associated virus (AAV)/Neo vector and identification of p81, a new AAV transcriptional promoter," Nov.-Dec. 1999, J Hum Virol, 2(6):359-368.
Hermonat, PL and N Muzyczka, "Use of adeno-associated virus as a mammalian DNA cloning vector: transduction of neomycin resistance into mammalian tissue culture cells," 1984, *Proc Natl Aced Sci USA*, 81:6466-6470.
Hermonat, P.L., M.A. Labow, R. Wright, K.I. Berns, and N. Muzyczka, "Genetics of adeno-associated virus: isolation and preliminary characterization of adeno-associated virus type 2 mutants," 1984, *J. Virol.*, 51:329-339.
Hoggan, M. D., N. R. Blacklow, and W. P. Rowe, "Studies of small DNA viruses found in various adenovirus preparations: physical, biological, and immunological characteristics," 1966, *Proc Natl Acad Sci USA*, 55:1467-1474.

(56) References Cited

OTHER PUBLICATIONS

Hoggan, M.D., "Adenovirus associated viruses," 1970, *Prog Med Virol*, 12:211-239.

Holt, J. R., "Viral-mediated gene transfer to study the molecular physiology of the Mammalian inner ear" 2002, *Audiol Neurootol*, 7(3):157-160.

Holt, J. R., D. C. Johns, et al., "Functional expression of exogenous proteins in mammalian sensory hair cells infected with adenoviral vectors," 1999, *J Neurophysiol*, 81(4):1881-1888.

Hsueh Y-P, Sheng M., "Regulated expression and subcellular localization of syndecan heparan sulfate proteoglycans and the syndecan-binding protein CASK/LIN-2 during rat brain development," 1999, *J Neurosci*, 19(17):7415-7425.

Hsueh Y-P, Yang F-C, Kharazia V, Naisbitt S, Cohen AR, Weinberg Rj, Sheng M, "Direct interaction of CASK/LIN-2 and syndecan heparan sulfate proteoglycan and their overlapping distribution in neuronal synapses," 1998, *J Cell Biol*, 142(1):139-151.

Hull, R. N., J. R. Minner, and J. W. Smith, "New viral agents recovered from tissue cultures of monkey kidney cells. I. Origin and properties of cytopathogenic agents S.V.1, S.V.2, S.V.4, S.V.5, S.V.6, S.V.11, S.V.12 and S.V.15," 1956, *Am J Hyg*, 63:204-215.

Hull, R. N., and J. R. Minner, "New viral agents recovered from tissue cultures of monkey kidney cells. II. Problems of isolation and identification," 1957, *Ann Ny Acad Sci*, 67:413-423.

Hull, R. N., J. R. Minner, and C. C. Mascoli, "New viral agents recovered from tissue cultures of monkey kidney cells. III. Recovery of additional agents both from cultures of monkey tissues and directly from tissues and excreta," 1958, *Am J Hyg*, 68:31-44.

Hunter, L.A. and R.J. Samulski, "Colocalization of adeno-associated virus Rep and capsid proteins in the nuclei of infected cells," 1992, *J. Virol.*, 66:317-324.

Im DS, Muzyczka N, "Partial purification of adeno-associated virus Rep78, Rep52, and Rep40 and their biochemical characterization," Feb. 1992, *J Virol.*, 66(2):1119-1128, XP002125031.

Inglis VI, Jones MP, TSE AD, Easton AS, "Neutrophils both reduce and increase permeability in a cell culture model of the blood-brain barrier," 2004, *Brain Res*, 998(2):218-229.

Ito, M. and H.D. Mayor, "Hemagglutinin of type 4 adeno-associated satellite virus," 1968, *J. Immunol*, 100:61-68.

Jaksch, M., K.D. Gerbitz, and C. Kilger, "Screening for mitochondrial Dna (mtDNA) point mutations using nonradioactive single strand conformation polymorphism (SSCP) analysis," 1995, *Clin. Biochem.*, 28:503-509.

Janik, J.E., M.M. Huston, K. Cho, and J.A. Rose, "Efficient syntheses of adeno-associated virus structural proteins requires both adenovirus DNA binding protein and VA I RNA," 1989, *Virology*, 168:320-329.

Jero J, Mhatre AN, Tseng CJ, Stern RE, Coling DE, Goldstein JA, Hong K, Zheng WW, Hogue AT, Lalwani AK., "Cochlear gene delivery through an intact round window membrane in mouse," 2001, *Hum Gene Ther*, 12(5):539-548.

Johansson CB, Momma S, Clarke DL, Risling M, Lendahl U, Frisen J, "Identification of a neural stem cell in the adult mammalian central nervous system," 1999, *Cell*, 96(1):25-34.

Kaludov et al., "Adeno-Associated Virus Serotype 4 (AAV4) and AAV5 Both Require Sialic Acid Binding for Hemagglutination and Efficient Transduction but Differ in Sialic Acid Linkage Specificity" 2001, *J. Virol.*, 75(15):6884-6893.

Kaludov et al., "Scalable Purification of Adeno-Associated Virus Type 2, 4 or 5 Using Ion-Exchange Chromatography," 2002, *Human Gene Therapy*, 13:1235-1243.

Kanzaki, S., K. Ogawa, et al., "Transgene expression in neonatal mouse inner ear explants mediated by first and advanced generation adenovirus vectors," 2002, *Hear Res*, 169(1-2):112-120.

Kaplitt, M.G., P. Leone, R.J. Samulski, X. Xiao, D.W. Pfaff, K.L. O'Malley, and J.M. During, "Long-term gene expression and phenotypic correction using adeno-associated virus vectors in the mammalian brain," 1994, *Nature Genetics*, 8:148-154.

Katano et al., "Identification of adeno-associated virus contamination in cell and virus stocks by PCR," Apr. 2004, *Biotechniques*, 36(4):676-680, XP001207105.

Kelsell, D.P., Dunlop, J., Stevens, H.P., Lench, n. J., Liang, J.N., Parry, G., Mueller, R.F., Leigh, I.M., "Connexin 26 mutations in hereditary non-syndromic sensorineural deafness," 1997, *Nature*, 387(6628):80-83.

Kern, A., K. Schmidt, C. Leder, O. J. Muller, C. E. Wobus, K. Bettinger, C. W. Von der Lieth, J. A. King, and J. A. Kleinschmidt, "Identification of a heparin-binding motif on adeno-associated virus type 2 capsids," 2003, *J Virol*, 77:11072-11081.

Klein RL, Meyer EM, Peel AL, Zolotukhin S, Meyers C, Muzyczka N, King MA., "Neuron-specific transduction in the rat septohippocampal or nigrostriatal pathway by recombinant adeno-associated virus vectors," 1998, *Exp Neurol*, 150:183-194.

Kondo M., Finkbeiner WE, and Widdicombe JH., "Simple technique for culture of highly differentiated cells from dog tracheal epithelium," 1991, *Am.J.Physiol*, 261:L106-L117.

Kotin et al., "Organization of adeno-associated virus DNA in latently infected Detroit 6 cells," 1989, *Virology*, 170(2):460-467.

Kotin, R.M., M. Siniscalco, R.J. Samulski, X. Zhu, L. Hunter, C.A. Laughlin, S. McLaughlin, N. Muzyczka, M. Rocchi, and K.I. Berns, "Site-specific integration by adeno-associated virus," 1990, *Proc. Natl. Acad. Sci. USA*, 87:2211-2215.

Kovacs P, Pinter M, Csaba G, "Effect of glucosphingolipid synthesis inhibitor (PPMP and PDMP) treatment on *Tetrahymena pyriformis*: data on the evolution of the signaling system," 2000, *Cell Biochem Funct*, 18(4):269-280.

Kyo S, Nakamura M, Kiyono T, Maida Y, Kanaya T, Tanaka M, Yatabe N, Inoue M, "Successful immortalization of endometrial glandular cells with normal structural and functional characteristics," 2003, *Am J Pathol*, 163(6):2259-2269.

Kyostio SR, Owens RA, Weitzman MD, Antoni BA, Chejanovsky N, Carter BJ, "Analysis of adeno-associated virus (AAV) wild-type and mutant Rep proteins for their abilities to negatively regulate AAV $p_5$ and $p_{19}$ mRNA levels," 1994, *J Virol*, 68(5):2947-2957, XP-002125032.

Laughlin, C.A., M.W. Myers, D.L. Risin, B.J. Carter, "Defective-interfering particles of the human parvovirus adeno-associated virus," 1979, *Virology*, 94:162-174.

Laughlin, C.A., N. Jones, and B.J. Carter, "Effect of deletions in adenovirus early region 1 genes upon replication of adeno-associated virus," 1982, *J. Virol*, 41:868-876.

Lee K, Kim YG, Jo EC, "Shuttle PCR-based cloning of the infectious adeno-associated virus type 5 genome," 2003, *J Virol Methods*, 111(2):75-84.

Li J, Samulski R, Xiao X, "Role for Highly Regulated rep Gene Expression in Adeno-Associated Virus Vector Production," 1997, *J Virol*, 71(7):5236-5243.

Li Duan, M., T. Bordet, et al., "Adenoviral and adeno-associated viral vector mediated gene transfer in the guinea pig cochlea," 2002, *Neuroreport*, 13(10):1295-1299.

Liang Y, Annan RS, Carr SA, Popp S, Mevissen M, Margolis RK, Margolis RU., "Mammalian homologues of the *Drosophila* slit protein are ligands of the heparan sulfate proteoglycan glypican-1 in brain," 1999, *J Biol Chem.*, 274(25):17885-17892.

Lo WD, Qu G, Sferra TJ, Clark R, Chen R, Johnson PR., "Adeno-associated virus-mediated gene transfer to the brain: duration and modulation of expression," 1999, *Hum Gene Ther*, 10:201-213.

Luchsinger, E., Strobbe, R., Dekegel, D. and Wellemans, G., "Use of B-IV zonal rotor centrifugation as a simple tool for the separation of adeno-associated X 7 virus (AAVX 7 ) from helper adenoviruses," 1971, *Arch Gesamte Virusforsch*, 33:251-258.

Luchsinger, E., Strobbe, R., Wellemans, G., Dekegel, D. And Sprecher-Goldberger, S., "Haemagglutinating adeno-associated virus (AAV) in association with bovine adenovirus type 1," 1970, *Brief report. Arch Gesamte Virusforsch*, 31:390-392.

Luebke, A. E., J. D. Steiger, et al., "A modified adenovirus can transfect cochlear hair cells in vivo without compromising cochlear function," 2001, *Gene Ther*, 8(10):789-794.

(56) References Cited

OTHER PUBLICATIONS

Luebke, A. E., P. K. Foster, et al., "Cochlear function and transgene expression in the guinea pig cochlea, using adenovirus- and adeno-associated virus-directed gene transfer," 2001, *Hum Gene Ther*, 12:773-781.

Maeda Y, Ikeda U, Ogasawara Y, Urabe M, Takizawa T, Saito T, Colosi P, Kurtzman G, Shimada K, Ozawa K, "Gene transfer into vascular cells using adeno-associated virus (AAV) vectors," 1997, *Cardiovasc Res*, 35(3):514-521, XP-002125030.

Mandel RJ, Rendahl KG, Spratt SK, Snyder RO, Cohen LK, Leff SE., "Characterization of intrastriatal recombinant adeno-associated virus-mediated gene transfer of human tyrosine hydroxylase and human GTP-cyclohydrolase I in a rat model of Parkinson's disease," 1998, *J Neurosci*, 18(11):4271-4284.

McCarty, D.M., J. Pereira, I. Zolotukhin, X. Zhou, J.H. Ryan, and N. Muzyczka, "Identification of linear DNA sequences that specifically bind the adeno-associated virus Rep protein," 1994, *J. Virol.*, 68:4988-4997.

McCown TJ, Xiao X, Li J, Breese GR, Samulski RJ, "Differential and Persistent Expression Patterns of CNS Gene Transfer by an Adeno-Associated Virus (AAV) Vector," 1996, *Brain Res*, 713:99-107.

McPherson, R. A., L. J. Rosenthal, and J. A. Rose, "Human cytomegalovirus completely helps adeno-associated virus replication," 1985, *Virology*, 147:217-222.

Mendelson, E., J.P. Trempe, and B.J. Carter "Identification of the trans-acting Rep proteins of adeno-associated virus by antibodies to a synthetic oligopeptide," 1986, *J. Virol.*, 60:823-832.

Meyers, C., Mane, M., Kokorina, N., Alam, S. and Hermonat, P.L., "Ubiquitous human adeno-associated virus type 2 autonomously replicates in differentiating keratinocytes of a normal skin model," 2000, *Virology*, 272:338-346.

Mitrani E, Ziv T, Thomsen G, Shimoni Y, Melton Da, Bril A, "Activin can induce the formation of axial structures and is expressed in the hypoblast of the chick," 1990, *Cell3.*, 63(3):495-501.

Mizukami, H., n. S. Young, and K.E. Brown, "Adeno-associated virus type 2 binds to a 150-kilodalton cell membrane glycoprotein," 1996, *Virology*, 217:124-130.

Mori, S., L. Wang, T. Takeuchi, and T. Kanda, "Two novel adeno-associated viruses from cynomolgus monkey: pseudotyping characterization of capsid protein," 2004, *Virology*, 330:375-383.

Mouw, M.B. And Pintel, D.J', "Adeno-associated virus RNAs appear in a temporal order and their splicing is, stimulated during coinfection with adenovirus," 2000, *J Virol*, 74:9878-9888.

Muramatsu S-I, et al., "Nucleotide Sequencing and Generation of an Infectious Clone of Adeno-Associated Virus 3," 1996, *Virology*, 221:208-217, XP000608965.

Muster et al., "Physical Mapping of Adeno-Associated Virus Serotype 4 DNA" 1980, *J. Virol.*, 35(3):653-661; XP002058632.

Muzyczka, N, "Use of adeno-associated virus as a general transduction vector for mammalian cells," 1992, *Curr Top Microbiol Immunol*, 158:97-129.

Myrup, A.C., Mohanty, S.B. and Hetrick, F.M., "Isolation and characterization of adeno-associated viruses from bovine adenovirus types 1 and 2," 1976, *Am J Vet Res*, 37(8):907-910.

Naz, S., Griffi,th A.J., Riazuddin, S., Hampton, L.L., Battey, J.F. Jr, Khan, S.N., Riazuddin, S., Wilcox, E.R., Friedman, T.B., "Mutations of *ESPN* cause autosomal recessive deafness and vestibular dysfunction," 2004, *J Med Genet*, 41(8):591-595.

No D, Yao TP, Evans RM., "Ecdysone-inducible gene expression in mammalian cells and transgenic mice," 1996, *Proc Natl Aced Sci USA*, 93(8):3346-3351.

Ogston, P., K. Raj, and P. Beard, "Productive replication of adeno-associated virus can occur in human papillomavirus type 16 (HPV-16) episome containing keratinocytes and is augmented by the HPV-16 E2 protein," 2000, *J Virol*, 74:3494-3504.

Opie et al., "Identification of amino acid residues in the capsid proteins of adeno-associated virus type 2 that contribute to heparan sulfate proteoglycan binding," 2003, *J Virol*, 77:6995-7006.

O'Riordan et al., "Scaleable Chromatographic Purification Process for Recombinant Adeno-Associated Virus (rAAV)," 2000, *J Gene Med*, 2:444-454.

Parks, W.P., J.L. Melnick, R. Rongey, and H.D. Mayor, "Physical assay and growth cycle studies of a defective adeno-satellite virus," 1967, *J. Virol.*, 1:171-180.

Podsakoff, G., K.K. Jr Wong, and S. Chatterjee, "Efficient gene transfer into nondividing cells by adeno-associated virus-based vectors," 1994, *J. Virol.*, 68:5656-5666.

Polishchuk R, Di Pentima A, Lippincott-Schwartz J, "Delivery of raft-associated, GPI-anchored proteins to the apical surface of polarized MDCK cells by a transcytotic pathway," 2004, *Nat Cell Biol*, 6(4):297-307.

Prasad KM, Zhou C, Trempe JP, "Characterization of the Rep78/adeno-associated virus complex," 1997, *Virology*, 229(1):183-192, XP-002125033.

Qing K, Mah C, Hansen J, Zhou S, Dwarki V, Srivastava A., "Human fibroblast growth factor receptor 1 is a co-receptor for infection by adeno-associated virus 2," 1999, *Nat Med*, 5(1):71-77.

Qiu J, Brown KE., "Integrin alphaVbeta5 is not involved in adeno-associated virus type 2 (AAV2) infection," 1999, *Virology*, 264(2):436-440.

Rabinowitz et al., "Cross-Packaging of a Single Adeno-Associated Virus (AAV) Type 2 Vector Genome into Multiple AAV Serotypes Enables Transduction with Broad Specificity," 2002, *J Virol*, 76(2):791-801, XP002247245.

Rabinowitz JE, Bowles DE, Faust SM, Ledford JG, Cunningham SE, Samulski RJ., "Cross-dressing the virion: the transcapsidation of adeno-associated virus serotypes functionally defines subgroups," 2004, *J Virol*, 78(9):4421-4432.

Reddy, V. S., P. Natarajan, B. Okerberg, K. Li, K. V. Damodaran, R. T. Morton, C. L. Brooks, 3rd, and J. E. Johnson, "Virus Particle Explorer (VIPER), a website for virus capsid structures and their computational analyses," 2001, *J Virol*, 75:11943-11947.

Rich DP, Couture LA, Cardoza LM, Guiggio LM, Armentano D., Espino PC, Hehir K., Welsh MJ, Smith AE, and Gregory RJ, "Development and analysis of recombinant adenoviruses for gene therapy of cystic fibrosis," 1993, *Hum.Gene Ther.*, 4:461-476.

Richardson, W. D., and H. Westphal, "Requirement for either early region 1a or early region 1b adenovirus gene products in the helper effect for adeno-associated virus," 1984, *J Virol*, 51:404-410.

Rose, J.A., M.D. Hoggan, F. Koczot, and A.J. Shatkin, "Genetic relatedness studies with adenovirus-associated viruses," 1968, *J. Virol.*, 2:999-1005.

Rosenfeld et al., "Adeno-associated viral vector gene transfer into leptomeningeal xenografts," 1997, *J Neuro-Oncology*, 34(2):139-144.

Russell et al., "Adeno-Associated Virus Vectors Preferentially Transduce Cells in S Phase," 1994, *Proc. Natl. Acad. Sci. USA*, 91:8915-8919.

Rutledge EA, Halbert CL, and Russell DW, "Infectious Clones and Vectors Derived from Adeno-Associated Virus (AAV) Serotypes other Than AAV Type 2," 1998, *J. Virol.*, 72(1):309-319.

Ryan, J.H., S. Zolotukhin, and N. Muzyczka, "Sequence requirements for binding of Rep68 to the adeno-associated virus terminal repeats," 1996, *J. Virol.*, 70:1542-1553.

Rzadzinska, A. K., M. E. Schneider, et al., "An actin molecular treadmill and myosins maintain stereocilia functional architecture and self-renewal," 2004, *J Cell Biol*, 164(6):887-897.

Saffer, L. D., R. Gu, et al., "An RT-PCR analysis of mRNA for growth factor receptors in damaged and control sensory epithelia of rat utricles," 1996, *Hear Res*, 94(1-2):14-23.

Salo R. and Mayor H., "Structural Polypeptides of Parvoviruses," 1977, *Virology*, 78:340-345; XP002058634.

Samulski RJ, Chang LS, Shenk T, "Helper-free stocks of recombinant adeno-associated viruses: normal integration does not require viral gene expression," 1989, *J Virol.*, 63(9):3822-3828, XP000283071.

Samulski, R. J., and T. Shenk, "Adenovirus E1B 55-$M_r$ polypeptide facilitates timely cytoplasmic accumulation of adeno-associated virus mRNAs," 1988, *J Virol*, 62:206-210.

(56) References Cited

OTHER PUBLICATIONS

Samulski, R.J., K.I. Berns, M. Tan, and N. Muzyczka, "Cloning of adeno-associated virus into pBR322: rescue of intact virus from the recombinant plasmid in human cells," 1982, *Proc Natl Acad Sci USA*, 79:2077-2081.
Sanes JR, JLR Rubenstein, and JF Nicolas, "Use of a recombinant retrovirus to study post-implantation cell lineage in mouse embryos," 1986, *EMBO J*, 5:3133-3142.
Sanlioglu, S., Benson, P.K., Yang, J., Atkinson, E.M., Reynolds, T. And Engelhardt, J.F., "Endocytosis and nuclear trafficking of adeno-associated virus type 2 are controlled by rac1 and phosphatidylinositol-3 kinase activation," 2000, *J Virol*, 74:9184-9196.
Schinkel AH, "P-Glycoprotein, a gatekeeper in the blood-brain barrier,"1999, *Adv Drug Deliv Rev*, 36:179-194.
Schlehofer JR, Heilbronn R, Georg-Fries B, zur Hausen H, "Inhibition of initiator-induced SV40 gene amplification in SV40-transformed Chinese hamster cells by infection with a defective parvovirus," 1983, *Int J Cancer*, 32(5):591-595, XP009010321.
Schlehofer, J. R., M. Ehrbar, and H. zur Hausen, "Vaccinia virus, herpes simplex virus, and carcinogens induce DNA amplification in a human cell line and support replication of a helpervirus dependent parvovirus," 1986, *Virology*, 152:110-117.
Schmidt M, Grot E, Cervenka P, Wainer S, Buck C, Chiorini JA, "Identification and characterization of novel adeno-associated virus isolates in AtCC virus stocks," 2006, *J Virol*, 80(10):5082-5085.
Schmidt et al., "Cloning and characterization of a bovine adeno-associated virus," 2004, *Journal of Virology*, 78(12):6509-6516, XP00233552.
Schneider, M. E., I. A. Belyantseva, et al., "Rapid renewal of auditory hair bundles," 2002, *Nature*, 418(6900):837-838.
Schwede, T., J. Kopp, N. Guex, and M. C. Peitsch, "Swiss-Model: An automated protein homology-modeling server," 2003, *Nucleic Acids Res*, 31:3381-3385.
Seiler MP, Miller AD, Zabner J, Halbert CL, "Adeno-associated virus types 5 and 6 use distinct receptors for cell entry," 2006, *Hum Gene Ther*, 17:10-19.
Seiler, M. P., C. L. Halbert, J. A. Chiorini, A. D. Miller, and J. Zabner, "AAV5 and AAV6 Mediate Gene Transfer to Human Airway Epthelia Via Different Receptors," 2002, *Mol Ther*, 5:S40.
Senapathy, P., J.D. Tratschin, and B.J. Carter, "Replication of adeno-associated virus DNA. Complementation of naturally occurring rep-mutants by a wild-type genome or an ori- mutant and correction of terminal palindrome deletions," 1984, *J Mol Biol*, 179:1-20.
Shou, J., J. L. Zheng, et al., "Robust generation of new hair cells in the mature mammalian inner ear by adenoviral expression of Hath1," 2003, *Mol Cell Neurosci*, 23(2):169-179.
Smith, R. H., S. A. Afione, et al , "Transposase-mediated construction of an integrated adeno-associated ' ' virus type 5 helper plasmid," 2002, *Biotechniques*, 33(1):204-206,208,210-211.
Snyder RO, Miao CH, Patijn GA, Spratt SK, Danos O., Nagy D., Gown Am, Winther B., Meuse L., Cohen LK, Thompson AR, and Kay MA, "Persistent and therapeutic concentrations of human factor IX in mice after hepatic gene transfer of recombinant AAV vectors," 1997, *Nat.Genet.*, 16:270-276.
Sobkowicz, H. M., J. M. Loftus, et al., "Tissue culture of the organ of Corti," 1993, *Acta Otolatyngol Suppl*, 502:3-36.
Srivastava et al., "Nucleotide Sequence and Organization of the Adeno-Associated Virus 2 Genome," 1983, *J. Virol.*, 45(2):555-564; XP002058633.
Staecker H, Li D, O'Malley BW Jr, Van De Water TR., "Gene expression in the mammalian cochlea: a study of multiple vector systems," 2001, *Acta Otolatyngol*, 121(2):157-163.
Stracker, T. H., G. D. Cassell, P. Ward, Y. M. Loo, B. van Breukelen, S. D. Carrington-Lawrence, R. K. Hamatake, P. C. van der Vliet, S. K. Weller, T. Melendy, and M. D. Weitzman, "The Rep protein of adeno-associated virus type 2 interacts with single-stranded DNA-binding proteins that enhance viral replication," 2004, *J Virol*, 78:441-453.
Summerford C, Bartlett JS, Samulski RJ , "*AlphaVbeta5* integrin: a co-receptor for adeno-associated virus type 2 infection," 1999, *Nat Med*, 5(1):78-82.
Summerford, C. and R. J. Samulski, "Membrane-associated heparan sulfate proteoglycan is a receptor for adeno-associated virus type 2 virions," 1998, *J Virol*, 72(2):1438-1445.
Superti, F., M. L. Marziano, A. Tinari, and G. Donelli, "Effect of polyions on the infectivity of SA-11 rotavirus in LCC-MK2 cells," 1993, *Comp Immunol Microbiol Infect Dis*, 16:55-62.
Suzuki, H., Y. Katori, et al., "Carbohydrate distribution in the living utricular macula of the guinea pig detected by lectins," 1995, *Hear Res*, 87(1-2):32-40.
Teramoto, S., Bartlett JS, McCarty DXX, Samulski RJ, and Boucher RC, "Factors influencing adeno-associated virus-mediated gene transfer to human cystic fibrosis airway epithelial cells: comparison with adenovirus vectors," 1998, *J Virol*, 72:8904-8912.
Thomas CE, Storm TA, Huang Z, Kay MA, "Rapid uncoating of vector genomes is the key to efficient liver transduction with pseudotyped adeno-associated virus vectors," 2004, *J Virol*, 78(6):3110-3122.
Tratschin, J. D., M. H. West, T. Sandbank, and B. J. Carter, "A human parvovirus, adeno-associated virus, as a eucaryotic vector: transient expression and encapsidation of the procaryotic gene for chloramphenicol acetyltransferase," 1984, *Mol Cell Biol*, 4:2072-2081.
Tratschin, J.D., I.L. Miller, and B.J. Carter, "Genetic analysis of adeno-associated virus: properties of deletion mutants constructed in vitro and evidence for an adeno-associated virus replication function," 1984, *J. Virol.*, 51:611-619.
Trempe, J.P. and B.J. Carter, "Regulation of adeno-associated virus gene expression in 293 cells: control of mRNA abundance and translation," 1988, *J. Virol.*, 62:68-74.
Trempe, J.P., E. Mendelson, and B.J. Carter, "Characterization of adeno-associated virus rep proteins in human cells by antibodies raised against rep expressed in *Escherichia coli*," 1987, *Virology*, 161:18-28.
Tuma PL and Hubbard AL, "Transcytosis: crossing cellular barriers," 2003, *Physiol Rev*, 83(3):871-932.
Voutetakis A, Kok MR, Zheng C, Bossis I, Wang J, Cotrim Ap, Marracino N, Goldsmith CM, Chiorini JA, Loh YP, Nieman LK, Baum Bj, "Reengineered salivary glands are stable endogenous bioreactors for systemic gene therapeutics," 2004, *Proc Nati Acad Sci USA*, 101(9):3053-3058.
Walsh, C.E., J.M. Liu, X. Xiao, N. S. Young, a.W. Nienhuis, and R.J. Samulski, "Regulated high level expression of a human gamma-globin gene introduced into erythroid cells by an adeno-associated virus vector," 1992, *Proc Natl Acad Sci USA*, 89:7257-7261.
Walters, R.W., Yi, S.M., Keshavjee, S., Brown, K.E., Welsh, M.J., Chiorini, J.A. And Zabner, J., "Binding of adeno-associated virus type 5 to 2,3-linked sialic acid is required for gene transfer," 2001, *J Biol Chem*, 276:20610-20616.
Walters, RW, Duan D., Engelhardt JF, and Welsh MJ., "Incorporation of adeno-associated virus in a calcium phosphate coprecipitate improves gene transfer to airway epithelia in vitro and in vivo," 2000, *J. Virol.*, 74:535-540.
Walters, RW, Grunst T., Bergelson JM, Finberg RW, Welsh MJ, and Zabner J., "Basolateral localization of fiber receptors limits adenovirus infection from the apical surface of airway epithelia," 1999, *J. Biol. Chem.*, 274:10219-10226.
Walz, C., A. Deprez, T. Dupressoir, M. Durst, M. Rabreau, and J. R. Schlehofer, "Interaction of human papillomavirus type 16 and adeno associated virus type 2 co-infecting human cervical epithelium," 1997, *J Gen Virol*, 78(Pt 6):1441-1452.
Wang G., Davidson BL, Melchert P., Slepushkin VA, van Es HH, Bodner M., Jolly DJ, and McCray PBJr., "Influence of cell polarity on retrovirus-mediated gene transfer to differentiated human airway epithelia," 1998, *Journal of Virology*, 72:9818-9826.
Wang X S, and A Srivastava, "Rescue and autonomous replication of adeno-associated virus type 2 genomes containing Rep-binding site mutations in the viral p5 promoter," 1998, *J Virol*, 72:4811-4818.
Ward, P., F. B. Dean, M. E. O'Donnell, and K. I. Berns, "Role of the adenovirus DNA-binding protein in in vitro adeno-associated virus DNA replication," 1998, *J Virol*, 72:420-427.

(56) References Cited

OTHER PUBLICATIONS

Weindler, F. W., and R. Heilbronn, "A subset of herpes simplex virus replication genes provides helper functions for productive adeno-associated virus replication," 1991, *J Virol*, 65:2476-2483.

Winocour, E., M.F. Callaham, and E. Huberman, "Perturbation of the cell cycle by adeno-associated virus," 1988, *Virology*, 167:393-399.

Xiao, W., N. Chirmule, S. C. Berta, B. McCullough, G. Gao, and J. M. Wilson, "Gene therapy vectors based on adeno-associated virus type 1," 1999, *J Virol*, 73:3994-4003.

Xiao et al., "Efficient Long-Term Gene Transfer into Muscle Tissue of Immunocompetent Mice by Adeno-Associated Virus Vector," 1996, *J. Virol.*, 70(11):8098-8108.

Xiao Xm Li J, Samulski Rj, "Production of High-Titer Recombinant Adeno-Associated Virus Vectors in the Absence of Helper Adenovirus," 1997, *J Virol*, 72(3):2224-2232.

Xie Q. and Chapman MS, "Canine parvovirus capsid structure, analyzed at 2.9 Å resolution," 1996, *J Mol Biol*, 264:497-520.

Yalkinoglu, A.O., Heilbronn, R., Burkle, A., Schlehofer, J.R. and zur Hausen, H., "DNA amplification of adeno-associated virus as a response to cellular genotoxic stress," 1988, *Cancer Res*, 48:3123-3129.

Yakobson, B., Hrynko, T.A., Peak, M.J. and Winocour, E., "Replication of adeno-associated virus in cells irradiated with UV light at 254 nm," 1989, *J Virol*, 63:1023-1030.

Yamano, S., Huang, L.Y., Ding, C., Chiorini, J.A., Goldsmith, C.M., Wellner, R.B., Golding, B., Kotin, R.M., Scott, D.E. And Baum, B.J., "Recombinant adeno-associated virus serotype 2 vectors mediate stable interleukin 10 secretion from salivary glands into the bloodstream," 2002, *Hum Gene Ther*, 13:287-298.

Yamaya, M., Finkbeiner WE, Chun SY, and Widdicombe JH, "Differentiated structure and function of cultures from human tracheal epithelium," 1992, *Am.J.Physiol*, 262:L713-L724.

Zabner J, Seiler M, Walters R, Kotin RM, Fulgeras W, Davidson BL, Chiorini JA, "Adeno-associated virus type 5 (AAV5) but not AAV2 binds to the apical surfaces of airway epithelia and facilitates gene transfer," 2000, *J Virol.*, 74(8):3852-3858, XP002197205.

Zabner, J., Zeiher BG, Friedman E, and Welsh MJ, "Adenovirus-mediated gene transfer to ciliated airway epithelia requires prolonged incubation time," 1996, *J.Virol.*, 70:6994-7003.

Zhang JR, Mostov KE, Lamm ME, Nanno M, Shimida S, Ohwaki M, Tuomanen E, "The polymeric immunoglobulin receptor translocates pneumococci across human nasopharyngeal epithelial cells," 2000, *Cell*, 102(6):827-837.

Zhu ZB, Makhija Sk, Lu B, Wang M, Rivera AA, Preuss M, Zhou F, Siegal GP, Alvarez RD, Curiel DT, "Transport across a polarized monolayer of Caco-2 cells by transferrin receptor-mediated adenovirus transcytosis," 2004, *Virol*, 325:116-128.

Zolotukhin et al., "Recombinant Adeno-Associated Virus Purification using Novel Methods Improves Infectious Titer and Yield," 1999, *Gene Ther*, 6:973-985.

\* cited by examiner

SEQUENCE LISTING

```
<160> NUMBER OF SEQ ID NOS: 55

<210> SEQ ID NO 1
<211> LENGTH: 4694
<212> TYPE: DNA
<213> ORGANISM: Artificial Sequence
<220> FEATURE:
<223> OTHER INFORMATION: Description of Artificial Sequence:  note =
      synthetic construct

<400> SEQUENCE: 1
tggccagttt  ccaagacagg  ctcgctcgct  cactcgggcc  ggggccccaa  aggggcccct        60
agcgaccgct  tcgcggtcgc  ggcccgagtg  agcgagcgag  cctgtcttgg  aaactggcca       120
gcactccggt  gaggtaatgc  cgtcacgtgg  tcgggaatgg  gaacgggaaa  tctcgcgaga       180
acgtaaacaa  atataagacg  gcgccacacg  gcgctgcgtc  atacgcgcgc  gcgcaccggc       240
```

```
gagatgaggt cgtactacga ggtcatcgtt cagctgccca acgacgtcga gagtcaggta      300
cctggaatct ccgattcgtt cgtcaactgg attacgtcgc gagaatggac gttgcctgag      360
gacgccgatt gggatttgga ccaggtcgat caagttcaac tgacgctcgg cgacaaaatc      420
caacgggaga ttcgaactca ttgggggacg atggccaaag aaccggactt tcactatttt      480
atccaactgg aacaaggtga ggtgttcttt catttacacg tcctgctgga aacgtgttcc      540
gtaaagccga tggtactcgg aagatatatc cgacatattc aacaaaaaat tgtgagtaaa      600
gtctactgcg ccacgagcct acgatggaag gatggatgcg tggtgaccaa gaccaaaaat      660
ttcgggggcg cgaacaaggt ccgggccgag tcgtatattc ccgcctacct gatcccgaaa      720
cagcaaccgg aagtgcagtg ggcgtggact aacgtgcccg agtatataaa agcgtgcttg      780
caccgagaac tgcgtgccag tctcgcgcga cttcacttcg aggaggcggg cgtctcgcaa      840
tccaaggaaa atctcgcgag aactgcagac ggcgctcccg tgatgccgac ccgcgtcagc      900
aaacgctaca tggagctcgt ggattggctc gtggagaagg ggatcaccac cgagaaggaa      960
tggctgctgg aaaacagaga aagctttcgg agctttcagg cctcgagcaa ctcggcgcgt     1020
cagatcaaga cggccctgca aggcgccatt caggagatgc ttctgaccaa gacggcggag     1080
gactacctcg tcggaaagga tcccgtctcg gacgacgaca tccgtcagaa ccgcatctac     1140
aagattctgg aactgaacca ctacgaccca gcgtacgtgg ggagtatttt ggtcgggtgg     1200
tgccagaaga aatggggcaa gcgaaacacg ctgtggctgt tcggacatgc gaccaccggc     1260
aagaccaaca tcgcggaggc tattgcccat gctgtgccgt tctatggatg cgttaactgg     1320
accaacgaga actttccgtt caacgactgc gtcgaaaaaa tgattatctg gtgggaggag     1380
ggcaaaatga ccgccaaagt ggtggaaaca gccaaggcga ttctgggagg atctcgggtg     1440
agagtggacc aaaaatgcaa agcttcggtt ccgatcgaac cgacgccggt cattattacc     1500
agtaacacca acatgtgtta tgtcatcgac gggaacacga ccacgttcga gcataagcag     1560
ccgttggagg acaggatgtt taagctcgaa ttgctgactc ggttgcctga tgactttggt     1620
aaggtgacca acaggaggt gcgtcaattc ttcaggtggt ctcaggatca cctgaccect     1680 gtgatcccag aattcctagt gcggaaggcg gagtctcgca aaagacccgc ccttccgggg     1740
gaaggctata taagcccgac aaagcggccc gcgctcgcag agcagcagca ggcgtcggag     1800
agcgcggacc cggttccac caggtatcgt atcaaatgct cgaaacattg cggtatggat     1860
aaaatgttgt tccttgcca aatttgtgaa tcgatgaaca gagatattaa tatttgtgct     1920
attcataaaa cgaccgactg taaagagtgt tccccgact acgggataa agatgatgta     1980 gaactacccc cctgtacaga acacaacgtg tctcgttgtt atcaatgtca ttcgggcgaa     2040
ttgtatcgcg tgacttcgga ctctgacgag aaacctgccc ccgagagtga tgaaggcacc     2100
gagccatcct atgctcccctg cacgattcac cacctgatgg gcaagagtca cgggttagtc     2160
acttgcgcgg cgtgtcggtt gaaaaatagt acgttgcatg atgacttgga tgacggtgat     2220
ctcgaacaat aaatgattga aatgtagcca tgtctctcat ttctgatgcg attccagatt     2280
ggttggagcg gttggtcaaa aagggagtga atgctgcagc tgatttctac catttggaaa     2340
gcggtcctcc tcgtcctaag gcaaatcagc aaactcaaga atctcttgaa aaggacgatt     2400
cgagaggtct cgtgttccca ggctacaatt atctaggccc tttcaacggt ctagataaag     2460
gagaacccgt caacgaggca gacgctgccg ccttagaaca cgacaaggct tacgacctcg     2520
aaatcaagga cgggcacaac ccgtactttg agtacaacga ggccgacaga cgtttccagg     2580
aacgtctcaa agacgatacc tcctttggag gcaatttagg taaagccatc ttccaggcca     2640
```

```
aaaagagggt tctcgaaccc tttggtctgg tggaagactc aaagacggct ccgaccggag    2700
acaagcggaa aggcgaagac gaacctcgtt tgcccgacac ttcttcacag actcccaaga    2760
aaaacaagaa gcctcgcaag gaaagacctt ccggcggggc agaagatccg ggcgaaggca    2820
cctcttccaa cgctggagca gcagcacccg cctctagtgt gggatcatct atcatggctg    2880
aaggaggtgg cggcccagtg ggcgatgcag gccagggtgc cgatggagtg ggcaattcct    2940
ccggaaattg gcattgcgat tcccaatggc tggaaaacgg agtcgtcact cgaaccaccc    3000
gaacctgggt cttgcccagc tacaacaacc acctgtacaa cgaatccaa ggacccagcg    3060 gaggcgacaa caacaacaaa ttctttggat tcagcacccc ctggggatac tttgactaca    3120
atcgattcca ctgccacttt tccccgcgag actggcaacg actcatcaac aacaactggg    3180
gcatccgtcc caaagcgatg cgctttagac tctttaacat ccaggttaaa gaggtcacgg    3240
tccaagactt caacaccacc atcggcaaca acctcaccag tacggtccag gtctttgcgg    3300
acaaggacta ccaactgccg tacgtcctcg gatcggctac cgaaggcacc ttcccgccgt    3360
tcccagcgga tatctacacg atcccgcagt acgggtactg cacgctaaac tacaacaacg    3420
aggcggtgga tcgttcggcc ttctactgtc tggactactt tccctcagac atgctgcgga    3480
caggaaataa ctttgagttt acttacacct tcgaggacgt tcctttccat agcatgtttg    3540
cccacaacca gacgctagac cggctgatga atcccctcgt ggatcagtac ctctgggctt    3600
tcagctccgt cagccaagca ggctcatctg gacgagctct tcattactcg cgggcgacta    3660
aaaccaacat ggcggctcaa tataggaact ggttacctgg gcctttcttc cgtgatcagc    3720
aaatctttac gggcgctagc aacatcacta aaaataacgt ctttagcgtt tgggaaaaag    3780
gcaagcaatg ggaactcgac aatcggacca acctaatgca gcccggtcct gcggcagcga    3840 ccaccttttag cggagaacct gaccgtcaag ccatgcaaaa cacgctggct tttagcagga    3900
ccgtctacga tcaaacgacc gccacgaccg atcgtaacca gatactcatc accaacgaag    3960
acgaaatcag acccaccaac tcggtcggta tcgacgcgtg gggagcagtt cccaccaaca    4020
accagtcgat cgtgaccccc ggcactcgcg cggccgtcaa caatcaaggg gcgcttcccg    4080
ggatggtgtg gcaaaacaga gacatttacc ctacagggac ccatttggcc aaaattcccg    4140
acactgacaa tcacttccat ccgtccccgc ttattgggcg gtttggctgc aagcatcccc    4200
ctccccagat tttcattaaa aacacacccg tccctgccaa cccttcggaa acgttccaga    4260
cggccaaagt ggcctccttc atcaaccagt actcgaccgg acagtgcacc gtcgaaatct    4320
tttgggaact caagaaggaa acctccaagc gctggaaccc cgaaatccag ttcacctcca    4380
actttggcaa cgcggccgac atccagtttg ccgtctccga cacgggatcc tattccgaac    4440
ctcgtcccat cggtacccgt taccttacca aacctctgta aattaaaccc ttcaataaac    4500
cgtttatgcg taactgtatt tccgtctcct gtcgttattc agtcacatga tgcggcatta    4560
cctcaccgga gtgctggcca gtttccaaga caggctcgct cgctcactcg ggccggggcc    4620 ccaaagggc ccctagcgac cgcttcgcgg tcgcggcccg agtgagcgag cgagcctgtc    4680
ttggaaactg gcca                                                      4694
```

<210> SEQ ID NO 2
<211> LENGTH: 1989
<212> TYPE: DNA
<213> ORGANISM: Artificial Sequence
<220> FEATURE:
<223> OTHER INFORMATION: Description of Artificial Sequence: note = synthetic construct

<400> SEQUENCE: 2

```
atgaggtcgt actacgaggt catcgttcag ctgcccaacg acgtcgagag tcaggtacct        60
ggaatctccg attcgttcgt caactggatt acgtcgcgag aatggacgtt gcctgaggac       120
gccgattggg atttggacca ggtcgatcaa gttcaactga cgctcggcga caaaatccaa       180
cgggagattc gaactcattg ggggacgatg ccaaagaac cggactttca ctattttatc        240
caactggaac aaggtgaggt gttctttcat ttacacgtcc tgctggaaac gtgttccgta       300
aagccgatgg tactcggaag atatatccga catattcaac aaaaaattgt gagtaaagtc       360
tactgcgcca cgagcctacg atggaaggat ggatgcgtgg tgaccaagac caaaaatttc       420
gggggcgcga acaaggtccg ggccgagtcg tatattcccg cctacctgat cccgaaacag       480
caaccggaag tgcagtgggc gtggactaac gtgcccgagt atataaaagc gtgcttgcac       540
cgagaactgc gtgccagtct cgcgcgactt cacttcgagg aggcgggcgt ctcgcaatcc       600
aaggaaaatc tcgcgagaac tgcagacggc gctcccgtga tgccgacccg cgtcagcaaa       660
cgctacatgg agctcgtgga ttggctcgtg gagaagggga tcaccaccga aaggaatgg        720
ctgctggaaa acagagaaag ctttcggagc tttcaggcct cgagcaactc ggcgcgtcag       780
atcaagacgg ccctgcaagg cgccattcag gagatgcttc tgaccaagac ggcggaggac       840
tacctcgtcg gaaaggatcc cgtctcggac gacgacatcc gtcagaaccg catctacaag       900
attctggaac tgaaccacta cgacccagcg tacgtgggga gtattttggt cgggtggtgc       960
cagaagaaat ggggcaagcg aaacacgctg tggctgttcg acatgcgac caccggcaag       1020
accaacatcg cggaggctat tgcccatgct gtgccgttct atggatgcgt taactggacc       1080
aacgagaact ttccgttcaa cgactgcgtc gaaaaaatga ttatctggtg ggaggagggc       1140
aaaatgaccg ccaaagtggt ggaaacagcc aaggcgattc tgggaggatc tcgggtgaga       1200
gtggaccaaa aatgcaaagc ttcggttccg atcgaaccga cgccggtcat tattaccagt       1260
aacaccaaca tgtgttatgt catcgacggg aacacgacca cgttcgagca taagcagccg       1320
ttggaggaca ggatgtttaa gctcgaattg ctgactcggt tgcctgatga ctttggtaag       1380
gtgaccaaac aggaggtgcg tcaattcttc aggtggtctc aggatcacct gaccctgtg       1440
atcccagaat tcctagtgcg gaaggcggag tctcgcaaaa gacccgcccc ttccggggaa       1500
ggctatataa gcccgacaaa gcggcccgcg ctcgcagagc agcagcaggc gtcggagagc       1560
gcggacccgg ttcccaccag gtatcgtatc aaatgctcga acattgcgg tatggataaa       1620
atgttgtttc cttgccaaat ttgtgaatcg atgaacagag atattaatat ttgtgctatt       1680
cataaaacga ccgactgtaa agagtgtttc cccgactacg gggataaaga tgatgtagaa       1740
ctaccccct gtacagaaca caacgtgtct cgttgttatc aatgtcattc gggcgaattg       1800
tatcgcgtga cttcggactc tgacgagaaa cctgcccccg agagtgatga aggcaccgag       1860
ccatcctatg ctccctgcac gattcaccac ctgatgggca agagtcacgg gttagtcact       1920
tgcgcggcgt gtcggttgaa aaatagtacg ttgcatgatg acttggatga cggtgatctc       1980
gaacaataa                                                              1989
```

<210> SEQ ID NO 3
<211> LENGTH: 662
<212> TYPE: PRT
<213> ORGANISM: Artificial Sequence
<220> FEATURE:
<223> OTHER INFORMATION: Description of Artificial Sequence: note = synthetic construct

<400> SEQUENCE: 3

| | | | | | | | | | | | | | | |
|---|---|---|---|---|---|---|---|---|---|---|---|---|---|---|
|Met|Arg|Ser|Tyr|Tyr|Glu|Val|Ile|Val|Gln|Leu|Pro|Asn|Asp|Val|Glu|
|1| | | |5| | | | |10| | | | |15|

Ser Gln Val Pro Gly Ile Ser Asp Ser Phe Val Asn Trp Ile Thr Ser
               20              25              30

Arg Glu Trp Thr Leu Pro Glu Asp Ala Asp Trp Asp Leu Asp Gln Val
    35                   40               45

Asp Gln Val Gln Leu Thr Leu Gly Asp Lys Ile Gln Arg Glu Ile Arg
50                 55               60

Thr His Trp Gly Thr Met Ala Lys Glu Pro Asp Phe His Tyr Phe Ile
65                 70              75              80

Gln Leu Glu Gln Gly Glu Val Phe Phe His Leu His Val Leu Leu Glu
               85              90              95

Thr Cys Ser Val Lys Pro Met Val Leu Gly Arg Tyr Ile Arg His Ile
          100              105             110

Gln Gln Lys Ile Val Ser Lys Val Tyr Cys Ala Thr Ser Leu Arg Trp
        115            120             125

Lys Asp Gly Cys Val Val Thr Lys Thr Lys Asn Phe Gly Gly Ala Asn
130               135              140

Lys Val Arg Ala Glu Ser Tyr Ile Pro Ala Tyr Leu Ile Pro Lys Gln
145               150              155             160

Gln Pro Glu Val Gln Trp Ala Trp Thr Asn Val Pro Glu Tyr Ile Lys
              165            170             175

Ala Cys Leu His Arg Glu Leu Arg Ala Ser Leu Ala Arg Leu His Phe
        180            185             190

Glu Glu Ala Gly Val Ser Gln Ser Lys Glu Asn Leu Ala Arg Thr Ala
    195                 200              205

Asp Gly Ala Pro Val Met Pro Thr Arg Val Ser Lys Arg Tyr Met Glu
210               215              220

Leu Val Asp Trp Leu Val Glu Lys Gly Ile Thr Thr Glu Lys Glu Trp
225               230              235             240

Leu Leu Glu Asn Arg Glu Ser Phe Arg Ser Phe Gln Ala Ser Ser Asn
              245            250             255

Ser Ala Arg Gln Ile Lys Thr Ala Leu Gln Gly Ala Ile Gln Glu Met
        260            265             270

Leu Leu Thr Lys Thr Ala Glu Asp Tyr Leu Val Gly Lys Asp Pro Val
    275                 280              285

Ser Asp Asp Asp Ile Arg Gln Asn Arg Ile Tyr Lys Ile Leu Glu Leu
290               295              300

Asn His Tyr Asp Pro Ala Tyr Val Gly Ser Ile Leu Val Gly Trp Cys
305               310              315             320

Gln Lys Lys Trp Gly Lys Arg Asn Thr Leu Trp Leu Phe Gly His Ala
              325            330             335

Thr Thr Gly Lys Thr Asn Ile Ala Glu Ala Ile Ala His Ala Val Pro
        340            345             350

Phe Tyr Gly Cys Val Asn Trp Thr Asn Glu Asn Phe Pro Phe Asn Asp
    355                 360              365

Cys Val Glu Lys Met Ile Ile Trp Trp Glu Glu Gly Lys Met Thr Ala
370               375              380

Lys Val Val Glu Thr Ala Lys Ala Ile Leu Gly Gly Ser Arg Val Arg
385               390              395             400

Val Asp Gln Lys Cys Lys Ala Ser Val Pro Ile Glu Pro Thr Pro Val

```
            405                 410                 415
Ile Ile Thr Ser Asn Thr Asn Met Cys Tyr Val Ile Asp Gly Asn Thr
            420                 425                 430

Thr Thr Phe Glu His Lys Gln Pro Leu Glu Asp Arg Met Phe Lys Leu
        435                 440                 445

Glu Leu Leu Thr Arg Leu Pro Asp Asp Phe Gly Lys Val Thr Lys Gln
    450                 455                 460

Glu Val Arg Gln Phe Phe Arg Trp Ser Gln Asp His Leu Thr Pro Val
465                 470                 475                 480

Ile Pro Glu Phe Leu Val Arg Lys Ala Glu Ser Arg Lys Arg Pro Ala
                485                 490                 495

Pro Ser Gly Glu Gly Tyr Ile Ser Pro Thr Lys Arg Pro Ala Leu Ala
            500                 505                 510

Glu Gln Gln Gln Ala Ser Glu Ser Ala Asp Pro Val Pro Thr Arg Tyr
        515                 520                 525

Arg Ile Lys Cys Ser Lys His Cys Gly Met Asp Lys Met Leu Phe Pro
    530                 535                 540

Cys Gln Ile Cys Glu Ser Met Asn Arg Asp Ile Asn Ile Cys Ala Ile
545                 550                 555                 560

His Lys Thr Thr Asp Cys Lys Glu Cys Phe Pro Asp Tyr Gly Asp Lys
                565                 570                 575

Asp Asp Val Glu Leu Pro Pro Cys Thr Glu His Asn Val Ser Arg Cys
            580                 585                 590

Tyr Gln Cys His Ser Gly Glu Leu Tyr Arg Val Thr Ser Asp Ser Asp
        595                 600                 605

Glu Lys Pro Ala Pro Glu Ser Asp Glu Gly Thr Glu Pro Ser Tyr Ala
    610                 615                 620

Pro Cys Thr Ile His His Leu Met Gly Lys Ser His Gly Leu Val Thr
625                 630                 635                 640

Cys Ala Ala Cys Arg Leu Lys Asn Ser Thr Leu His Asp Asp Leu Asp
                645                 650                 655

Asp Gly Asp Leu Glu Gln
            660

<210> SEQ ID NO 4
<211> LENGTH: 1323
<212> TYPE: DNA
<213> ORGANISM: Artificial Sequence
<220> FEATURE:
<223> OTHER INFORMATION: Description of Artificial Sequence:  note =
      synthetic construct

<400> SEQUENCE: 4
atggagctcg tggattggct cgtggagaag gggatcacca ccgagaagga atggctgctg      60 gaaacagag aaagctttcg gagctttcag gcctcgagca actcggcgcg tcagatcaag     120
acggccctgc aaggcgccat tcaggagatg cttctgacca agacggcgga ggactacctc     180
gtcggaaagg atcccgtctc ggacgacgac atccgtcaga accgcatcta caagattctg     240
gaactgaacc actacgaccc agcgtacgtg gggagtattt tggtcgggtg gtgccagaag     300
aaatggggca agcgaaacac gctgtggctg ttcggacatg cgaccaccgg caagaccaac     360
atcgcggagg ctattgccca tgctgtgccg ttctatggat gcgttaactg gaccaacgag     420
aactttccgt tcaacgactg cgtcgaaaaa atgattatct ggtgggagga gggcaaaatg     480
accgccaaag tggtggaaac agccaaggcg attctgggag gatctcgggt gagagtggac     540
```

```
                                                -continued caaaaatgca aagcttcggt tccgatcgaa ccgacgccgg tcattattac cagtaacacc      600
aacatgtgtt atgtcatcga cgggaacacg accacgttcg agcataagca gccgttggag      660
gacaggatgt ttaagctcga attgctgact cggttgcctg atgactttgg taaggtgacc      720
aaacaggagg tgcgtcaatt cttcaggtgg tctcaggatc acctgacccc tgtgatccca      780
gaattcctag tgcggaaggc ggagtctcgc aaaagacccg cccttccgg ggaaggctat       840 ataagcccga caaagcggcc cgcgctcgca gagcagcagc aggcgtcgga gagcgcggac      900
ccggttccca ccaggtatcg tatcaaatgc tcgaaacatt gcggtatgga taaaatgttg      960
tttccttgcc aaatttgtga atcgatgaac agagatatta atatttgtgc tattcataaa     1020
acgaccgact gtaaagagtg tttccccgac tacggggata aagatgatgt agaactaccc     1080
ccctgtacag aacacaacgt gtctcgttgt tatcaatgtc attcgggcga attgtatcgc     1140
gtgacttcgg actctgacga gaaacctgcc ccgagagtg atgaaggcac cgagccatcc      1200
tatgctccct gcacgattca ccacctgatg ggcaagagtc acgggttagt cacttgcgcg     1260
gcgtgtcggt tgaaaaatag tacgttgcat gatgacttgg atgacggtga tctcgaacaa     1320
taa                                                                    1323
```

<210> SEQ ID NO 5
<211> LENGTH: 440
<212> TYPE: PRT
<213> ORGANISM: Artificial Sequence
<220> FEATURE:
<223> OTHER INFORMATION: Description of Artificial Sequence:   note =
      synthetic construct

<400> SEQUENCE: 5

```
Met Glu Leu Val Asp Trp Leu Val Glu Lys Gly Ile Thr Thr Glu Lys
  1               5                  10                  15

Glu Trp Leu Leu Glu Asn Arg Glu Ser Phe Arg Ser Phe Gln Ala Ser
             20                  25                  30

Ser Asn Ser Ala Arg Gln Ile Lys Thr Ala Leu Gln Gly Ala Ile Gln
         35                  40                  45

Glu Met Leu Leu Thr Lys Thr Ala Glu Asp Tyr Leu Val Gly Lys Asp
     50                  55                  60

Pro Val Ser Asp Asp Ile Arg Gln Asn Arg Ile Tyr Lys Ile Leu
 65                  70                  75                  80

Glu Leu Asn His Tyr Asp Pro Ala Tyr Val Gly Ser Ile Leu Val Gly
                 85                  90                  95

Trp Cys Gln Lys Lys Trp Gly Leu Arg Asn Thr Leu Trp Leu Phe Gly
            100                 105                 110

His Ala Thr Thr Gly Lys Thr Asn Ile Ala Glu Ala Ile Ala His Ala
        115                 120                 125

Val Pro Phe Tyr Gly Cys Val Asn Trp Thr Asn Glu Asn Phe Pro Phe
    130                 135                 140

Asn Asp Cys Val Glu Lys Met Ile Ile Trp Trp Glu Glu Gly Lys Met
145                 150                 155                 160

Thr Ala Lys Val Val Glu Thr Ala Lys Ala Ile Leu Gly Gly Ser Arg
                165                 170                 175

Val Arg Val Asp Gln Lys Cys Lys Ala Ser Val Pro Ile Glu Pro Thr
            180                 185                 190

Pro Val Ile Ile Thr Ser Asn Thr Asn Met Cys Tyr Val Ile Asp Gly
        195                 200                 205

Asn Thr Thr Thr Phe Glu His Lys Gln Pro Leu Glu Asp Arg Met Phe
```

|     |     |     |     | 210 |     |     |     |     | 215 |     |     |     |     | 220 |     |
| --- | --- | --- | --- | --- | --- | --- | --- | --- | --- | --- | --- | --- | --- | --- | --- |

Lys Leu Glu Leu Leu Thr Arg Leu Pro Asp Asp Phe Gly Lys Val Thr
225                 230                 235                 240

Lys Gln Glu Val Arg Gln Phe Phe Arg Trp Ser Gln Asp His Leu Thr
            245                 250                 255

Pro Val Ile Pro Glu Phe Leu Val Arg Lys Ala Glu Ser Arg Lys Arg
            260                 265                 270

Pro Ala Pro Ser Gly Glu Gly Tyr Ile Ser Pro Thr Lys Arg Pro Ala
            275                 280                 285

Leu Ala Glu Gln Gln Gln Ala Ser Glu Ser Ala Asp Pro Val Pro Thr
            290                 295                 300

Arg Tyr Arg Ile Lys Cys Ser Lys His Cys Gly Met Asp Lys Met Leu
305                 310                 315                 320

Phe Pro Cys Gln Ile Cys Glu Ser Met Asn Arg Asp Ile Asn Ile Cys
            325                 330                 335

Ala Ile His Lys Thr Thr Asp Cys Lys Glu Cys Phe Pro Asp Tyr Gly
            340                 345                 350

Asp Lys Asp Asp Val Glu Leu Pro Pro Cys Thr Glu His Asn Val Ser
            355                 360                 365

Arg Cys Tyr Gln Cys His Ser Gly Glu Leu Tyr Arg Val Thr Ser Asp
            370                 375                 380

Ser Asp Glu Lys Pro Ala Pro Glu Ser Asp Glu Gly Thr Glu Pro Ser
385                 390                 395                 400

Tyr Ala Pro Cys Thr Ile His His Leu Met Gly Lys Ser His Gly Leu
            405                 410                 415

Val Thr Cys Ala Ala Cys Arg Leu Lys Asn Ser Thr Leu His Asp Asp
            420                 425                 430

Leu Asp Asp Gly Asp Leu Glu Gln
            435                 440

<210> SEQ ID NO 6
<211> LENGTH: 1626
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 6

```
atgaggtcgt actacgaggt catcgttcag ctgcccaacg acgtcgagag tcaggtacct      60
ggaatctccg attcgttcgt caactggatt acgtcgcgag aatggacgtt gcctgaggac     120
gccgattggg atttggacca ggtcgatcaa gttcaactga cgctcggcga caaaatccaa     180
cgggagattc gaactcattg ggggacgatg gccaagaaac cggactttca ctattttatc     240
caactggaac aaggtgaggt gttctttcat ttacacgtcc tgctggaaac gtgttccgta     300
aagccgatgg tactcggaag atatatccga catattcaac aaaaaattgt gagtaaagtc     360
tactgcgcca cgagcctacg atggaaggat ggatgcgtgg tgaccaagac caaaaatttc     420
gggggcgcga acaaggtccg ggccgagtcg tatattcccg cctacctgat cccgaaacag     480
caaccggaag tgcagtgggc gtggactaac gtgcccgagt atataaaagc gtgcttgcac     540
cgagaactgc gtgccagtct cgcgcgactt cacttcgagg aggcgggcgt ctcgcaatcc     600
aaggaaaatc tcgcgagaac tgcagacggc gctcccgtga tgccgacccg cgtcagcaaa     660
cgctacatgg agctcgtgga ttggctcgtg gagaagggga tcaccaccga aaggaatgg     720
```

```
ctgctggaaa acagagaaag ctttcggagc tttcaggcct cgagcaactc ggcgcgtcag   780
atcaagacgg ccctgcaagg cgccattcag gagatgcttc tgaccaagac ggcggaggac   840
tacctcgtcg gaaaggatcc cgtctcggac gacgacatcc gtcagaaccg catctacaag   900
attctggaac tgaaccacta cgacccagcg tacgtgggga gtattttggt cgggtggtgc   960
cagaagaaat ggggcaagcg aaacacgctg tggctgttcg acatgcgac caccggcaag   1020 accaacatcg cggaggctat tgcccatgct gtgccgttct atggatgcgt taactggacc   1080
aacgagaact tccgttcaa cgactgcgtc gaaaaaatga ttatctggtg ggaggagggc   1140
aaaatgaccg ccaaagtggt ggaaacagcc aaggcgattc tgggaggatc tcgggtgaga   1200
gtggaccaaa aatgcaaagc ttcggttccg atcgaaccga cgccggtcat tattaccagt   1260
aacaccaaca tgtgttatgt catcgacggg aacacgacca cgttcgagca taagcagccg   1320
ttggaggaca ggatgtttaa gctcgaattg ctgactcggt tgcctgatga ctttggtaag   1380
gtgaccaaac aggaggtgcg tcaattcttc aggtggtctc aggatcacct gaccctgtg   1440 atcccagaat tcctagtgcg gaaggcggag tctcgcaaaa gacccgcccc ttccggggaa   1500
ggctatataa gcccgacaaa gcggcccgcg ctcgcagagc agcagcaggc gtcggagagc   1560
gcggacccgg ttcccaccag attggttgga gcggttggtc aaaaagggag tgaatgctgc   1620
agctga                                                              1626
```

<210> SEQ ID NO 7
<211> LENGTH: 541
<212> TYPE: PRT
<213> ORGANISM: Artificial Sequence
<220> FEATURE:
<223> OTHER INFORMATION: Description of Artificial Sequence: note = synthetic construct

<400> SEQUENCE: 7

```
Met Arg Ser Tyr Tyr Glu Val Ile Val Gln Leu Pro Asn Asp Val Glu
 1               5                  10                  15

Ser Gln Val Pro Gly Ile Ser Asp Ser Phe Val Asn Trp Ile Thr Ser
            20                  25                  30

Arg Glu Trp Thr Leu Pro Glu Asp Ala Asp Trp Asp Leu Asp Gln Val
        35                  40                  45

Asp Gln Val Gln Leu Thr Leu Gly Asp Lys Ile Gln Arg Glu Ile Arg
    50                  55                  60

Thr His Trp Gly Thr Met Ala Lys Glu Pro Asp Phe His Tyr Phe Ile
65                  70                  75                  80

Gln Leu Glu Gln Gly Glu Val Phe Phe His Leu Val Leu Leu Glu
            85                  90                  95

Thr Cys Ser Val Lys Pro Met Val Leu Gly Arg Tyr Ile Arg His Ile
            100                 105                 110

Gln Gln Lys Ile Val Ser Lys Val Tyr Cys Ala Thr Ser Leu Arg Trp
        115                 120                 125

Lys Asp Gly Cys Val Val Thr Lys Thr Lys Asn Phe Gly Gly Ala Asn
    130                 135                 140

Lys Val Arg Ala Glu Ser Tyr Ile Pro Ala Tyr Leu Ile Pro Lys Gln
145                 150                 155                 160

Gln Pro Glu Val Gln Trp Ala Trp Thr Asn Val Pro Glu Tyr Ile Lys
                165                 170                 175

Ala Cys Leu His Arg Glu Leu Arg Ala Ser Leu Ala Arg Leu His Phe
            180                 185                 190
```

-continued

```
Glu Glu Ala Gly Val Ser Gln Ser Lys Glu Asn Leu Ala Arg Thr Ala
            195                 200                 205

Asp Gly Ala Pro Val Met Pro Thr Arg Val Ser Lys Arg Tyr Met Glu
        210                 215                 220

Leu Val Asp Trp Leu Val Glu Lys Gly Ile Thr Thr Glu Lys Glu Trp
225                 230                 235                 240

Leu Leu Glu Asn Arg Glu Ser Phe Arg Ser Phe Gln Ala Ser Ser Asn
                245                 250                 255

Ser Ala Arg Gln Ile Lys Thr Ala Leu Gln Gly Ala Ile Gln Glu Met
            260                 265                 270

Leu Leu Thr Lys Thr Ala Glu Asp Tyr Leu Val Gly Lys Asp Pro Val
        275                 280                 285

Ser Asp Asp Ile Arg Gln Asn Arg Ile Tyr Lys Ile Leu Glu Leu
290                 295                 300

Asn His Tyr Asp Pro Ala Tyr Val Gly Ser Ile Leu Val Gly Trp Cys
305                 310                 315                 320

Gln Lys Lys Trp Gly Lys Arg Asn Thr Leu Trp Leu Phe Gly His Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Glu Lys Met Ile Ile Trp Trp Glu Glu Gly Lys Met Thr Ala
370                 375                 380

Lys Val Val Glu Thr Ala Lys Ala Ile Leu Gly Gly Ser Arg Val Arg
385                 390                 395                 400

Val Asp Gln Lys Cys Lys Ala Ser Val Pro Ile Glu Pro Thr Pro Val
                405                 410                 415

Ile Ile Thr Ser Asn Thr Asn Met Cys Tyr Val Ile Asp Gly Asn Thr
            420                 425                 430

Thr Thr Phe Glu His Lys Gln Pro Leu Glu Asp Arg Met Phe Lys Leu
        435                 440                 445

Glu Leu Leu Thr Arg Leu Pro Asp Asp Phe Gly Lys Val Thr Lys Gln
450                 455                 460

Glu Val Arg Gln Phe Phe Arg Trp Ser Gln Asp His Leu Thr Pro Val
465                 470                 475                 480

Ile Pro Glu Phe Leu Val Arg Lys Ala Glu Ser Arg Lys Arg Pro Ala
                485                 490                 495

Pro Ser Gly Glu Gly Tyr Ile Ser Pro Thr Lys Arg Pro Ala Leu Ala
            500                 505                 510

Glu Gln Gln Gln Ala Ser Glu Ser Ala Asp Pro Val Pro Thr Arg Leu
        515                 520                 525

Val Gly Ala Val Gly Gln Lys Gly Ser Glu Cys Cys Ser
530                 535                 540

<210> SEQ ID NO 8
<211> LENGTH: 960
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 8
atggagctcg tggattggct cgtggagaag gggatcacca ccgagaagga atggctgctg      60
```

-continued

```
gaaaacagag aaagctttcg gagctttcag gcctcgagca actcggcgcg tcagatcaag    120
acggccctgc aaggcgccat tcaggagatg cttctgacca agacggcgga ggactacctc    180
gtcggaaagg atcccgtctc ggacgacgac atccgtcaga accgcatcta aagattctg     240
gaactgaacc actacgaccc agcgtacgtg gggagtattt tggtcgggtg gtgccagaag    300
aaatggggca agcgaaacac gctgtggctg ttcggacatg cgaccaccgg caagaccaac    360
atcgcggagg ctattgccca tgctgtgccg ttctatggat gcgttaactg gaccaacgag    420
aactttccgt tcaacgactg cgtcgaaaaa atgattatct ggtgggagga gggcaaaatg    480
accgccaaag tggtggaaac agccaaggcg attctgggag atctcgggt gagagtggac     540
caaaaatgca aagcttcggt tccgatcgaa ccgacgccgg tcattattac cagtaacacc    600
aacatgtgtt atgtcatcga cgggaacacg accacgttcg agcataagca gccgttggag    660
gacaggatgt ttaagctcga attgctgact cggttgcctg atgactttgg taaggtgacc    720
aaacaggagg tgcgtcaatt cttcaggtgg tctcaggatc acctgacccc tgtgatccca    780
gaattcctag tgcggaaggc ggagtctcgc aaaagacccg cccccttccgg ggaaggctat   840
ataagcccga caaagcggcc cgcgctcgca gagcagcagc aggcgtcgga gagcgcggac    900
ccggttccca ccagattggt tggagcggtt ggtcaaaaag ggagtgaatg ctgcagctga    960
```

<210> SEQ ID NO 9
<211> LENGTH: 319
<212> TYPE: PRT
<213> ORGANISM: Artificial Sequence
<220> FEATURE:
<223> OTHER INFORMATION: Description of Artificial Sequence: note = synthetic construct

<400> SEQUENCE: 9

```
Met Glu Leu Val Asp Trp Leu Val Glu Lys Gly Ile Thr Thr Glu Lys
  1               5                  10                  15

Glu Trp Leu Leu Glu Asn Arg Glu Ser Phe Arg Ser Phe Gln Ala Ser
             20                  25                  30

Ser Asn Ser Ala Arg Gln Ile Lys Thr Ala Leu Gln Gly Ala Ile Gln
         35                  40                  45

Glu Met Leu Leu Thr Lys Thr Ala Glu Asp Tyr Leu Val Gly Lys Asp
     50                  55                  60

Pro Val Ser Asp Asp Ile Arg Gln Asn Arg Ile Tyr Lys Ile Leu
 65                  70                  75                  80

Glu Leu Asn His Tyr Asp Pro Ala Tyr Val Gly Ser Ile Leu Val Gly
             85                  90                  95

Trp Cys Gln Lys Lys Trp Gly Lys Arg Asn Thr Leu Trp Leu Phe Gly
            100                 105                 110

His Ala Thr Thr Gly Lys Thr Asn Ile Ala Glu Ala Ile Ala His Ala
        115                 120                 125

Val Pro Phe Tyr Gly Cys Val Asn Trp Thr Asn Glu Asn Phe Pro Phe
    130                 135                 140

Asn Asp Cys Val Glu Lys Met Ile Ile Trp Trp Glu Glu Gly Lys Met
145                 150                 155                 160

Thr Ala Lys Val Val Glu Thr Ala Lys Ala Ile Leu Gly Gly Ser Arg
                165                 170                 175

Val Arg Val Asp Gln Lys Cys Lys Ala Ser Val Pro Ile Glu Pro Thr
            180                 185                 190

Pro Val Ile Ile Thr Ser Asn Thr Asn Met Cys Tyr Val Ile Asp Gly
        195                 200                 205
```

```
Asn Thr Thr Thr Phe Glu His Lys Gln Pro Leu Glu Asp Arg Met Phe
            210                 215                 220
Lys Leu Glu Leu Leu Thr Arg Leu Pro Asp Asp Phe Gly Lys Val Thr
225                 230                 235                 240
Lys Gln Glu Val Arg Gln Phe Phe Arg Trp Ser Gln Asp His Leu Thr
                245                 250                 255
Pro Val Ile Pro Glu Phe Leu Val Arg Lys Ala Glu Ser Arg Lys Arg
            260                 265                 270
Pro Ala Pro Ser Gly Glu Gly Tyr Ile Ser Pro Thr Lys Arg Pro Ala
        275                 280                 285
Leu Ala Glu Gln Gln Gln Ala Ser Glu Ser Ala Asp Pro Val Pro Thr
    290                 295                 300
Arg Leu Val Gly Ala Val Gly Gln Lys Gly Ser Glu Cys Cys Ser
305                 310                 315
```

<210> SEQ ID NO 10
<211> LENGTH: 2232
<212> TYPE: DNA
<213> ORGANISM: Artificial Sequence
<220> FEATURE:
<223> OTHER INFORMATION: Description of Artificial Sequence: note = synthetic construct

<400> SEQUENCE: 10

| | | |
|---|---|---|
| atgtctctca tttctgatgc gattccagat tggttggagc ggttggtcaa aagggagtg | 60 |
| aatgctgcag ctgatttcta ccatttggaa agcggtcctc ctcgtcctaa ggcaaatcag | 120 |
| caaactcaag aatctcttga aaaggacgat tcgagaggtc tcgtgttccc aggctacaat | 180 |
| tatctaggcc ctttcaacgg tctagataaa ggagaacccg tcaacgaggc agacgctgcc | 240 |
| gccttagaac acgacaaggc ttacgacctc gaaatcaagg acgggcacaa cccgtacttt | 300 |
| gagtacaacg aggccgacag acgtttccag gaacgtctca agacgatac ctcctttgga | 360 |
| ggcaatttag gtaaagccat cttccaggcc aaaagaggg ttctcgaacc ctttggtctg | 420 |
| gtggaagact caaagacggc tccgaccgga gacaagcgga aagcgaaga cgaacctcgt | 480 |
| ttgcccgaca cttcttcaca gactcccaag aaaaacaaga agcctcgcaa ggaaagacct | 540 |
| tccggcgggg cagaagatcc gggcgaaggc acctcttcca acgctggagc agcagcaccc | 600 |
| gcctctagtg tgggatcatc tatcatggct gaaggaggtg gcggcccagt gggcgatgca | 660 |
| ggccagggtg ccgatggagt gggcaattcc tccggaaatt ggcattgcga ttcccaatgg | 720 |
| ctggaaaacg gagtcgtcac tcgaaccacc cgaacctggg tcttgcccag ctacaacaac | 780 |
| cacctgtaca acgaatccaa ggacccagc ggaggcgaca acaacaacaa attctttgga | 840 |
| ttcagcaccc cctggggata ctttgactac aatcgattcc actgccactt ttccccgcga | 900 |
| gactggcaac gactcatcaa caacaactgg ggcatccgtc caaagcgat gcgctttaga | 960 |
| ctctttaaca tccaggttaa agaggtcacg gtccaagact tcaacaccac catcggcaac | 1020 |
| aacctcacca gtacggtcca ggtctttgcg gacaaggact accaactgcc gtacgtcctc | 1080 |
| ggatcggcta ccgaaggcac cttcccgccg ttcccagcgg atatctacac gatcccgcag | 1140 |
| tacgggtact cgacgctaaa ctacaacaac gaggcggtgg atcgttcggc cttctactgt | 1200 |
| ctggactact ttccctcaga catgctgcgg acaggaaata actttgagtt acttacacc | 1260 |
| ttcgaggacg ttcctttcca tagcatgttt gcccacaacc agacgctaga ccggctgatg | 1320 |
| aatcccctcg tggatcagta cctctggggct ttcagctccg tcagccaagc aggctcatct | 1380 |

-continued

```
ggacgagctc ttcattactc gcgggcgact aaaaccaaca tggcggctca atataggaac    1440
tggttacctg ggccttttctt ccgtgatcag caaatcttta cgggcgctag caacatcact    1500
aaaaataacg tctttagcgt ttgggaaaaa ggcaagcaat gggaactcga caatcggacc    1560
aacctaatgc agcccggtcc tgcggcagcg accaccttta gcggagaacc tgaccgtcaa    1620
gccatgcaaa acacgctggc ttttagcagg accgtctacg atcaaacgac cgccacgacc    1680
gatcgtaacc agatactcat caccaacgaa gacgaaatca gacccaccaa ctcggtcggt    1740
atcgacgcgt ggggagcagt tcccaccaac aaccagtcga tcgtgacccc cggcactcgc    1800
gcggccgtca acaatcaagg ggcgcttccc gggatggtgt ggcaaaacag agacatttac    1860
cctacaggga cccatttggc caaaattccc gacactgaca atcacttcca tccgtccccg    1920
cttattgggc ggtttggctg caagcatccc cctccccaga ttttcattaa aaacacaccc    1980
gtccctgcca acccttcgga aacgttccag acggccaaag tggcctcctt catcaaccag    2040
tactcgaccg gacagtgcac cgtcgaaatc ttttgggaac tcaagaagga aacctccaag    2100
cgctggaacc ccgaaatcca gttcacctcc aactttggca acgcggccga catccagttt    2160
gccgtctccg acacgggatc ctattccgaa cctcgtccca tcggtacccg ttaccttacc    2220
aaacctctgt aa                                                         2232
```

<210> SEQ ID NO 11
<211> LENGTH: 743
<212> TYPE: PRT
<213> ORGANISM: Artificial Sequence
<220> FEATURE:
<223> OTHER INFORMATION: Description of Artificial Sequence: note = synthetic construct

<400> SEQUENCE: 11

```
Met Ser Leu Ile Ser Asp Ala Ile Pro Asp Trp Leu Glu Arg Leu Val
  1               5                  10                  15

Lys Lys Gly Val Asn Ala Ala Ala Asp Phe Tyr His Leu Glu Ser Gly
             20                  25                  30

Pro Pro Arg Pro Lys Ala Asn Gln Gln Thr Gln Glu Ser Leu Glu Lys
         35                  40                  45

Asp Asp Ser Arg Gly Leu Val Phe Pro Gly Tyr Asn Tyr Leu Gly Pro
     50                  55                  60

Phe Asn Gly Leu Asp Lys Gly Glu Pro Val Asn Glu Ala Asp Ala Ala
 65                  70                  75                  80

Ala Leu Glu His Asp Lys Ala Tyr Asp Leu Glu Ile Lys Asp Gly His
                 85                  90                  95

Asn Pro Tyr Phe Glu Tyr Asn Glu Ala Asp Arg Arg Phe Gln Glu Arg
            100                 105                 110

Leu Lys Asp Asp Thr Ser Phe Gly Gly Asn Leu Gly Lys Ala Ile Phe
        115                 120                 125

Gln Ala Lys Lys Arg Val Leu Glu Pro Phe Gly Leu Val Glu Asp Ser
    130                 135                 140

Lys Thr Ala Pro Thr Gly Asp Lys Arg Lys Gly Glu Asp Glu Pro Arg
145                 150                 155                 160

Leu Pro Asp Thr Ser Ser Gln Thr Pro Lys Lys Asn Lys Lys Pro Arg
                165                 170                 175

Lys Glu Arg Pro Ser Gly Gly Ala Glu Asp Pro Gly Glu Gly Thr Ser
            180                 185                 190

Ser Asn Ala Gly Ala Ala Ala Pro Ala Ser Ser Val Gly Ser Ser Ile
        195                 200                 205
```

```
Met Ala Glu Gly Gly Gly Pro Val Gly Asp Ala Gly Gln Gly Ala
    210             215                 220

Asp Gly Val Gly Asn Ser Ser Gly Asn Trp His Cys Asp Ser Gln Trp
225             230                 235                 240

Leu Glu Asn Gly Val Val Thr Arg Thr Arg Thr Trp Val Leu Pro
            245                 250                 255

Ser Tyr Asn Asn His Leu Tyr Lys Arg Ile Gln Gly Pro Ser Gly Gly
            260                 265                 270

Asp Asn Asn Lys Phe Phe Gly Phe Ser Thr Pro Trp Gly Tyr Phe
            275                 280                 285

Asp Tyr Asn Arg Phe His Cys His Phe Ser Pro Arg Asp Trp Gln Arg
290                 295                 300

Leu Ile Asn Asn Asn Trp Gly Ile Arg Pro Lys Ala Met Arg Phe Arg
305                 310                 315                 320

Leu Phe Asn Ile Gln Val Lys Glu Val Thr Val Gln Asp Phe Asn Thr
                325                 330                 335

Thr Ile Gly Asn Asn Leu Thr Ser Thr Val Gln Val Phe Ala Asp Lys
                340                 345                 350

Asp Tyr Gln Leu Pro Tyr Val Leu Gly Ser Ala Thr Glu Gly Thr Phe
            355                 360                 365

Pro Pro Phe Pro Ala Asp Ile Tyr Thr Ile Pro Gln Tyr Gly Tyr Cys
370                 375                 380

Thr Leu Asn Tyr Asn Asn Glu Ala Val Asp Arg Ser Ala Phe Tyr Cys
385                 390                 395                 400

Leu Asp Tyr Phe Pro Ser Asp Met Leu Arg Thr Gly Asn Asn Phe Glu
                405                 410                 415

Phe Thr Tyr Thr Phe Glu Asp Val Pro Phe His Ser Met Phe Ala His
            420                 425                 430

Asn Gln Thr Leu Asp Arg Leu Met Asn Pro Leu Val Asp Gln Tyr Leu
            435                 440                 445

Trp Ala Phe Ser Ser Val Ser Gln Ala Gly Ser Ser Gly Arg Ala Leu
450                 455                 460

His Tyr Ser Arg Ala Thr Lys Thr Asn Met Ala Ala Gln Tyr Arg Asn
465                 470                 475                 480

Trp Leu Pro Gly Pro Phe Phe Arg Asp Gln Gln Ile Phe Thr Gly Ala
                485                 490                 495

Ser Asn Ile Thr Lys Asn Asn Val Phe Ser Val Trp Glu Lys Gly Lys
            500                 505                 510

Gln Trp Glu Leu Asp Asn Arg Thr Asn Leu Met Gln Pro Gly Pro Ala
            515                 520                 525

Ala Ala Thr Thr Phe Ser Gly Glu Pro Asp Arg Gln Ala Met Gln Asn
530                 535                 540

Thr Leu Ala Phe Ser Arg Thr Val Tyr Asp Gln Thr Ala Thr Thr
545                 550                 555                 560

Asp Arg Asn Gln Ile Leu Ile Thr Asn Glu Asp Ile Arg Pro Thr
                565                 570                 575

Asn Ser Val Gly Ile Asp Ala Trp Gly Ala Val Pro Thr Asn Asn Gln
            580                 585                 590

Ser Ile Val Thr Pro Gly Thr Arg Ala Ala Val Asn Asn Gln Gly Ala
                595                 600                 605

Leu Pro Gly Met Val Trp Gln Asn Arg Asp Ile Tyr Pro Thr Gly Thr
610                 615                 620
```

```
His Leu Ala Lys Ile Pro Asp Thr Asp Asn His Phe His Pro Ser Pro
625                 630                 635                 640

Leu Ile Gly Arg Phe Gly Cys Lys His Pro Pro Gln Ile Phe Ile
            645                 650                 655

Lys Asn Thr Pro Val Pro Ala Asn Pro Ser Glu Thr Phe Gln Thr Ala
                660                 665                 670

Lys Val Ala Ser Phe Ile Asn Gln Tyr Ser Thr Gly Gln Cys Thr Val
            675                 680                 685

Glu Ile Phe Trp Glu Leu Lys Lys Glu Thr Ser Lys Arg Trp Asn Pro
690                 695                 700

Glu Ile Gln Phe Thr Ser Asn Phe Gly Asn Ala Ala Asp Ile Gln Phe
705                 710                 715                 720

Ala Val Ser Asp Thr Gly Ser Tyr Ser Glu Pro Arg Pro Ile Gly Thr
                725                 730                 735

Arg Tyr Leu Thr Lys Pro Leu
            740
```

<210> SEQ ID NO 12
<211> LENGTH: 1797
<212> TYPE: DNA
<213> ORGANISM: Artificial Sequence
<220> FEATURE:
<223> OTHER INFORMATION: Description of Artificial Sequence: note = synthetic construct

<400> SEQUENCE: 12

```
acggctccga ccggagacaa gcggaaaggc gaagacgaac ctcgtttgcc cgacacttct    60
tcacagactc ccaagaaaaa caagaagcct cgcaaggaaa gaccttccgg cggggcagaa   120
gatccgggcg aaggcacctc ttccaacgct ggagcagcag cacccgcctc tagtgtggga   180
tcatctatca tggctgaagg aggtggcggc ccagtgggcg atgcaggcca gggtgccgat   240
ggagtgggca attcctccgg aaattggcat tgcgattccc aatggctgga aaacggagtc   300
gtcactcgaa ccacccgaac ctgggtcttg cccagctaca caaccacct gtacaaacga   360
atccaaggac ccagcggagg cgacaacaac aacaaattct ttggattcag caccccctgg   420
ggatactttg actacaatcg attccactgc cacttttccc cgcgagactg gcaacgactc   480
atcaacaaca actggggcat ccgtcccaaa gcgatgcgct ttagactctt aacatccag   540
gttaaagagg tcacggtcca agacttcaac accaccatcg gcaacaacct caccagtacg   600
gtccaggtct ttgcggacaa ggactaccaa ctgccgtacg tcctcggatc ggctaccgaa   660
ggcaccttcc cgccgttccc agcggatatc tacacgatcc cgcagtacgg gtactgcacg   720
ctaaactaca caacgaggc ggtggatcgt tcggccttct actgtctgga ctactttccc   780
tcagacatgc tgcggacagg aaataacttt gagtttactt acaccttcga ggacgttcct   840
ttccatagca tgtttgccca caaccagacg ctagaccggc tgatgaatcc cctcgtggat   900
cagtacctct gggctttcag ctccgtcagc aagcaggct catctggacg agctcttcat   960
tactcgcggg cgactaaaac caacatggcg gctcaatata ggaactggtt acctgggcct  1020
ttcttccgtg atcagcaaat ctttacgggc gctagcaaca tcactaaaaa taacgtcttt  1080
agcgtttggg aaaaaggcaa gcaatgggaa ctcgacaatc ggaccaacct aatgcagccc  1140
ggtcctgcgg cagcgaccac ctttagcgga gaacctgacc gtcaagccat gcaaaacacg  1200
ctggcttttta gcaggaccgt ctacgatcaa acgaccgcca cgaccgatcg taaccagata  1260
ctcatcacca cgaagacga aatcagaccc accaactcgg tcggtatcga cgcgtgggga  1320
```

```
gcagttccca ccaacaacca gtcgatcgtg acccccggca ctcgcgcggc cgtcaacaat    1380 caagggcgc ttcccgggat ggtgtggcaa aacagagaca tttaccctac agggacccat    1440
ttggccaaaa ttcccgacac tgacaatcac ttccatccgt ccccgcttat tgggcggttt    1500
ggctgcaagc atcccctcc ccagatttc attaaaaaca cacccgtccc tgccaaccct    1560
tcggaaacgt tccagacggc caaagtggcc tccttcatca accagtactc gaccggacag    1620
tgcaccgtcg aaatcttttg ggaactcaag aaggaaacct ccaagcgctg aaccccgaa     1680 atccagttca cctccaactt tggcaacgcg gccgacatcc agtttgccgt ctccgacacg    1740
ggatcctatt ccgaacctcg tcccatcggt acccgttacc ttaccaaacc tctgtaa      1797
```

```
<210> SEQ ID NO 13
<211> LENGTH: 598
<212> TYPE: PRT
<213> ORGANISM: Artificial Sequence
<220> FEATURE:
<223> OTHER INFORMATION: Description of Artificial Sequence:  note =
      synthetic construct

<400> SEQUENCE: 13
```

```
Thr Ala Pro Thr Gly Asp Lys Arg Lys Gly Glu Asp Glu Pro Arg Leu
 1               5                  10                  15

Pro Asp Thr Ser Ser Gln Thr Pro Lys Lys Asn Lys Lys Pro Arg Lys
             20                  25                  30

Glu Arg Pro Ser Gly Gly Ala Glu Asp Pro Gly Glu Gly Thr Ser Ser
         35                  40                  45

Asn Ala Gly Ala Ala Pro Ala Ser Ser Val Gly Ser Ser Ile Met
 50                  55                  60

Ala Glu Gly Gly Gly Gly Pro Val Gly Asp Ala Gly Gln Gly Ala Asp
 65                  70                  75                  80

Gly Val Gly Asn Ser Ser Gly Asn Trp His Cys Asp Ser Gln Trp Leu
                 85                  90                  95

Glu Asn Gly Val Val Thr Arg Thr Thr Arg Thr Trp Val Leu Pro Ser
            100                 105                 110

Tyr Asn Asn His Leu Tyr Lys Arg Ile Gln Gly Pro Ser Gly Gly Asp
        115                 120                 125

Asn Asn Asn Lys Phe Phe Gly Phe Ser Thr Pro Trp Gly Tyr Phe Asp
    130                 135                 140

Tyr Asn Arg Phe His Cys His Phe Ser Pro Arg Asp Trp Gln Arg Leu
145                 150                 155                 160

Ile Asn Asn Asn Trp Gly Ile Arg Pro Lys Ala Met Arg Phe Arg Leu
                165                 170                 175

Phe Asn Ile Gln Val Lys Glu Val Thr Val Gln Asp Phe Asn Thr Thr
            180                 185                 190

Ile Gly Asn Asn Leu Thr Ser Thr Val Gln Val Phe Ala Asp Lys Asp
        195                 200                 205

Tyr Gln Leu Pro Tyr Val Leu Gly Ser Ala Thr Glu Gly Thr Phe Pro
    210                 215                 220

Pro Phe Pro Ala Asp Ile Tyr Thr Ile Pro Gln Tyr Gly Tyr Cys Thr
225                 230                 235                 240

Leu Asn Tyr Asn Asn Glu Ala Val Asp Arg Ser Ala Phe Tyr Cys Leu
                245                 250                 255

Asp Tyr Phe Pro Ser Asp Met Leu Arg Thr Gly Asn Asn Phe Glu Phe
            260                 265                 270

Thr Tyr Thr Phe Glu Asp Val Pro Phe His Ser Met Phe Ala His Asn
```

```
                275                 280                 285
Gln Thr Leu Asp Arg Leu Met Asn Pro Leu Val Asp Gln Tyr Leu Trp
        290                 295                 300
Ala Phe Ser Ser Val Ser Gln Ala Gly Ser Ser Gly Arg Ala Leu His
305                 310                 315                 320
Tyr Ser Arg Ala Thr Lys Thr Asn Met Ala Ala Gln Tyr Arg Asn Trp
                325                 330                 335
Leu Pro Gly Pro Phe Phe Arg Asp Gln Gln Ile Phe Thr Gly Ala Ser
            340                 345                 350
Asn Ile Thr Lys Asn Asn Val Phe Ser Val Trp Glu Lys Gly Lys Gln
                355                 360                 365
Trp Glu Leu Asp Asn Arg Thr Asn Leu Met Gln Pro Gly Pro Ala Ala
        370                 375                 380
Ala Thr Thr Phe Ser Gly Glu Pro Asp Arg Gln Ala Met Gln Asn Thr
385                 390                 395                 400
Leu Ala Phe Ser Arg Thr Val Tyr Asp Gln Thr Thr Ala Thr Thr Asp
                405                 410                 415
Arg Asn Gln Ile Leu Ile Thr Asn Glu Asp Glu Ile Arg Pro Thr Asn
            420                 425                 430
Ser Val Gly Ile Asp Ala Trp Gly Ala Val Pro Thr Asn Asn Gln Ser
                435                 440                 445
Ile Val Thr Pro Gly Thr Arg Ala Ala Val Asn Asn Gln Gly Ala Leu
        450                 455                 460
Pro Gly Met Val Trp Gln Asn Arg Asp Ile Tyr Pro Thr Gly Thr His
465                 470                 475                 480
Leu Ala Lys Ile Pro Asp Thr Asp Asn His Phe His Pro Ser Pro Leu
                485                 490                 495
Ile Gly Arg Phe Gly Cys Lys His Pro Pro Gln Ile Phe Ile Lys
            500                 505                 510
Asn Thr Pro Val Pro Ala Asn Pro Ser Glu Thr Phe Gln Thr Ala Lys
                515                 520                 525
Val Ala Ser Phe Ile Asn Gln Tyr Ser Thr Gly Gln Cys Thr Val Glu
        530                 535                 540
Ile Phe Trp Glu Leu Lys Lys Glu Thr Ser Lys Arg Trp Asn Pro Glu
545                 550                 555                 560
Ile Gln Phe Thr Ser Asn Phe Gly Asn Ala Ala Asp Ile Gln Phe Ala
                565                 570                 575
Val Ser Asp Thr Gly Ser Tyr Ser Glu Pro Arg Pro Ile Gly Thr Arg
            580                 585                 590
Tyr Leu Thr Lys Pro Leu
            595

<210> SEQ ID NO 14
<211> LENGTH: 1608
<212> TYPE: DNA
<213> ORGANISM: Artificial Sequence
<220> FEATURE:
<223> OTHER INFORMATION: Description of Artificial Sequence:  note =
      synthetic construct

<400> SEQUENCE: 14
atggctgaag gaggtggcgg cccagtgggc gatgcaggcc agggtgccga tggagtgggc      60
aattcctccg gaaattggca ttgcgattcc caatggctgg aaaacggagt cgtcactcga     120
accacccgaa cctgggtctt gcccagctac aacaaccacc tgtacaaacg aatccaagga     180
```

```
cccagcggag gcgacaacaa caacaaattc tttggattca gcaccccctg gggatacttt    240
gactacaatc gattccactg ccacttttcc ccgcgagact ggcaacgact catcaacaac    300
aactggggca tccgtcccaa agcgatgcgc tttagactct taacatcca ggttaaagag    360
gtcacggtcc aagacttcaa caccaccatc ggcaacaacc tcaccagtac ggtccaggtc    420
tttgcggaca aggactacca actgccgtac gtcctcggat cggctaccga aggcaccttc    480
ccgccgttcc cagcggatat ctacacgatc ccgcagtacg ggtactgcac gctaaactac    540
aacaacgagg cggtggatcg ttcggccttc tactgtctgg actactttcc ctcagacatg    600
ctgcggacag gaataacttt gagtttact tacaccttcg aggacgttcc tttccatagc     660
atgtttgccc acaaccagac gctagaccgg ctgatgaatc ccctcgtgga tcagtacctc    720
tgggctttca gctccgtcag ccaagcaggc tcatctggac gagctcttca ttactcgcgg    780
gcgactaaaa ccaacatggc ggctcaatat aggaactggt tacctgggcc tttcttccgt    840
gatcagcaaa tctttacggg cgctagcaac atcactaaaa ataacgtctt tagcgtttgg    900
gaaaaaggca agcaatggga actcgacaat cggaccaacc taatgcagcc cggtcctgcg    960
gcagcgacca cctttagcgg agaacctgac cgtcaagcca tgcaaaacac gctggctttt    1020
agcaggaccg tctacgatca aacgaccgcc acgaccgatc gtaaccagat actcatcacc    1080
aacgaagacg aaatcagacc caccaactcg gtcggtatcg acgcgtgggg agcagttccc    1140
accaacaacc agtcgatcgt gaccccccggc actcgcgcgg ccgtcaacaa tcaaggggcg    1200
cttcccggga tggtgtggca aaacagagac atttacccta cagggaccca tttggccaaa    1260
attcccgaca ctgacaatca cttccatccg tccccgctta ttgggcggtt tggctgcaag    1320
catcccccctc cccagatttt cattaaaaac acaccccgtcc ctgccaaccc ttcggaaacg    1380
ttccagacgg ccaaagtggc ctccttcatc aaccagtact cgaccggaca gtgcaccgtc    1440
gaaatctttt gggaactcaa gaaggaaacc tccaagcgct ggaaccccga aatccagttc    1500
acctccaact ttggcaacgc ggccgacatc cagtttgccg tctccgacac gggatcctat    1560
tccgaacctc gtcccatcgg tacccgttac cttaccaaac ctctgtaa                1608
```

<210> SEQ ID NO 15
<211> LENGTH: 535
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 15

```
Met Ala Glu Gly Gly Gly Pro Val Gly Asp Ala Gly Gln Gly Ala
 1               5                  10                  15

Asp Gly Val Gly Asn Ser Ser Gly Asn Trp His Cys Asp Ser Gln Trp
             20                  25                  30

Leu Glu Asn Gly Val Val Thr Arg Thr Thr Arg Thr Trp Val Leu Pro
         35                  40                  45

Ser Tyr Asn Asn His Leu Tyr Lys Arg Ile Gln Gly Pro Ser Gly Gly
     50                  55                  60

Asp Asn Asn Asn Lys Phe Phe Gly Phe Ser Thr Pro Trp Gly Tyr Phe
 65                  70                  75                  80

Asp Tyr Asn Arg Phe His Cys His Ser Pro Arg Asp Trp Gln Arg
                 85                  90                  95

Leu Ile Asn Asn Asn Trp Gly Ile Arg Pro Lys Ala Met Arg Phe Arg
            100                 105                 110
```

```
Leu Phe Asn Ile Gln Val Lys Glu Val Thr Val Gln Asp Phe Asn Thr
            115                 120                 125
Thr Ile Gly Asn Asn Leu Thr Ser Thr Val Gln Val Phe Ala Asp Lys
        130                 135                 140
Asp Tyr Gln Leu Pro Tyr Val Leu Gly Ser Ala Thr Glu Gly Thr Phe
145                 150                 155                 160
Pro Pro Phe Pro Ala Asp Ile Tyr Thr Ile Pro Gln Tyr Gly Tyr Cys
                165                 170                 175
Thr Leu Asn Tyr Asn Asn Glu Ala Val Asp Arg Ser Ala Phe Tyr Cys
                180                 185                 190
Leu Asp Tyr Phe Pro Ser Asp Met Leu Arg Thr Gly Asn Asn Phe Glu
            195                 200                 205
Phe Thr Tyr Thr Phe Glu Asp Val Pro Phe His Ser Met Phe Ala His
        210                 215                 220
Asn Gln Thr Leu Asp Arg Leu Met Asn Pro Leu Val Asp Gln Tyr Leu
225                 230                 235                 240
Trp Ala Phe Ser Ser Val Ser Gln Ala Gly Ser Ser Gly Arg Ala Leu
                245                 250                 255
His Tyr Ser Arg Ala Thr Lys Thr Asn Met Ala Ala Gln Tyr Arg Asn
                260                 265                 270
Trp Leu Pro Gly Pro Phe Phe Arg Asp Gln Gln Ile Phe Thr Gly Ala
            275                 280                 285
Ser Asn Ile Thr Lys Asn Asn Val Phe Ser Val Trp Glu Lys Gly Lys
        290                 295                 300
Gln Trp Glu Leu Asp Asn Arg Thr Asn Leu Met Gln Pro Gly Pro Ala
305                 310                 315                 320
Ala Ala Thr Thr Phe Ser Gly Glu Pro Asp Arg Gln Ala Met Gln Asn
                325                 330                 335
Thr Leu Ala Phe Ser Arg Thr Val Tyr Asp Gln Thr Thr Ala Thr Thr
                340                 345                 350
Asp Arg Asn Gln Ile Leu Ile Thr Asn Glu Asp Glu Ile Arg Pro Thr
            355                 360                 365
Asn Ser Val Gly Ile Asp Ala Trp Gly Ala Val Pro Thr Asn Asn Gln
        370                 375                 380
Ser Ile Val Thr Pro Gly Thr Arg Ala Ala Val Asn Asn Gln Gly Ala
385                 390                 395                 400
Leu Pro Gly Met Val Trp Gln Asn Arg Asp Ile Tyr Pro Thr Gly Thr
                405                 410                 415
His Leu Ala Lys Ile Pro Asp Thr Asp Asn His Phe His Pro Ser Pro
                420                 425                 430
Leu Ile Gly Arg Phe Gly Cys Lys His Pro Pro Gln Ile Phe Ile
            435                 440                 445
Lys Asn Thr Pro Val Pro Ala Asn Pro Ser Glu Thr Phe Gln Thr Ala
        450                 455                 460
Lys Val Ala Ser Phe Ile Asn Gln Tyr Ser Thr Gly Gln Cys Thr Val
465                 470                 475                 480
Glu Ile Phe Trp Glu Leu Lys Lys Glu Thr Ser Lys Arg Trp Asn Pro
                485                 490                 495
Glu Ile Gln Phe Thr Ser Asn Phe Gly Asn Ala Ala Asp Ile Gln Phe
                500                 505                 510
Ala Val Ser Asp Thr Gly Ser Tyr Ser Glu Pro Arg Pro Ile Gly Thr
            515                 520                 525
```

```
Arg Tyr Leu Thr Lys Pro Leu
    530             535
```

<210> SEQ ID NO 16
<211> LENGTH: 120
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 16
tggccagttt ccaagacagg ctcgctcgct cactcgggcc ggggcccccaa aggggcccct    60 agcgaccgct tcgcggtcgc ggcccgagtg agcgagcgag cctgtcttgg aaactggcca   120

<210> SEQ ID NO 17
<211> LENGTH: 120
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 17
accggtcaaa ggttctgtcc gagcgagcga gtgagcccgg ccccggcgtt tccccgggga    60
tcgctgggga agcgccagcg ccgggctcac tcgctcgctc ggacagaacc tttgaccggt   120

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 18
gcactccggt gaggtaatgc cg                                              22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 19
cggcattacc tcaccggagt gc                                              22

<210> SEQ ID NO 20
<211> LENGTH: 7
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 20 ccggtcg                                                                7

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: note = synthetic construct

<400> SEQUENCE: 21
cgagtgagcg agcgag                                                         16

<210> SEQ ID NO 22
<211> LENGTH: 101
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 22
tcacgtggtc gggaatggga acgggaaatc tcgcgagaac gtaaacaaat ataagacggc          60
gccacacggc gctgcgtcat acgcgcgcgc gcaccggcga g                            101

<210> SEQ ID NO 23
<211> LENGTH: 252
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 23
aatttcgggg gcgcgaacaa ggtccgggcc gagtcgtata ttcccgccta cctgatcccg          60
aaacagcaac cggaagtgca gtgggcgtgg actaacgtgc ccgagtatat aaaagcgtgc         120
ttgcaccgag aactgcgtgc cagtctcgcg cgacttcact tcgaggaggc gggcgtctcg         180
caatccaagg aaaatctcgc gagaactgca gacggcgctc ccgtgatgcc gacccgcgtc         240
agcaaacgct ac                                                            252

<210> SEQ ID NO 24
<211> LENGTH: 196
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 24
gtaaggtgac caaacaggag gtgcgtcaat tcttcaggtg gtctcaggat cacctgaccc          60
ctgtgatccc agaattccta gtgcggaagg cggagtctcg caaaagaccc gccccttccg         120
gggaaggcta tataagcccg acaaagcggc ccgcgctcgc agagcagcag caggcgtcgg         180
agagcgcgga cccggt                                                        196

<210> SEQ ID NO 25
<211> LENGTH: 164
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 25
cggcattacc tcaccggagt gctggccagt ttccaagaca ggctcgctcg ctcactcggg          60
ccggggcccc aaaggggccc ctagcgaccg cttcgcggtc gcggcccgag tgagcgagcg         120
agcctgtctt ggaaactggc cagcactccg gtgaggtaat gccg                         164

<210> SEQ ID NO 26
<211> LENGTH: 4675
<212> TYPE: DNA
<213> ORGANISM: Artificial Sequence
<220> FEATURE:
<223> OTHER INFORMATION: Description of Artificial Sequence: note = synthetic construct

<400> SEQUENCE: 26

| | | | | | |
|---|---|---|---|---|---|
| ttggccactc | cctctctgcg | cgctcgctcg | ctcactgagg | ccgggcgacc | aaaggtcgcc | 60 |
| cgacgcccgg | gctttgcccg | gcggcctca | gtgagcgagc | gagcgcgcag | agagggagtg | 120 |
| gccaactcca | tcactagggg | ttcctggagg | ggtggagtcg | tgacgtgaat | tacgtcatag | 180 |
| ggttagggag | gtcctgtatt | agaggtcacg | tgagtgtttt | gcgacatttt | gcgacaccat | 240 |
| gtggtcacgc | tgggtattta | agcccgagtg | agcacgcagg | gtctccattt | tgaagcggga | 300 |
| ggtttgaacg | cgcagccgcc | atgccggggt | tttacgagat | tgtgattaag | gtccccagcg | 360 |
| accttgacgg | gcatctgccc | ggcatttctg | acagctttgt | gaactgggtg | ccgagaagg | 420 |
| aatgggagtt | gccgccagat | tctgacatgg | atctgaatct | gattgagcag | gcaccctga | 480 |
| ccgtggccga | aagctgcag | cgcgactttc | tgacggaatg | gcgccgtgtg | agtaaggccc | 540 |
| cggaggccct | tttctttgtg | caatttgaga | agggagagag | ctacttccac | atgcacgtgc | 600 |
| tcgtggaaac | caccggggtg | aaatccatgg | ttttgggacg | tttcctgagt | cagattcgcg | 660 |
| aaaaactgat | tcagagaatt | taccgcggga | tcgagccgac | tttgccaaac | tggttcgcgg | 720 |
| tcacaaagac | cagaaatggc | gccggaggcg | ggaacaaggt | ggtggatgag | tgctacatcc | 780 |
| ccaattactt | gctccccaaa | acccagcctg | agctccagtg | ggcgtggact | aatatggaac | 840 |
| agtatttaag | cgcctgtttg | aatctcacgg | agcgtaaacg | gttggtggcg | cagcatctga | 900 |
| cgcacgtgtc | gcagacgcag | gagcagaaca | aagagaatca | gaatcccaat | tctgatgcgc | 960 |
| cggtgatcag | atcaaaaact | tcagccaggt | acatggagct | ggtcgggtgg | ctcgtggaca | 1020 |
| aggggattac | ctcggagaag | cagtggatcc | aggaggacca | ggcctcatac | atctccttca | 1080 |
| atgcggcctc | caactcgcgg | tcccaaatca | aggctgcctt | ggacaatgcg | ggaaagatta | 1140 |
| tgagcctgac | taaaaccgcc | cccgactacc | tggtgggcca | gcagcccgtg | gaggacattt | 1200 |
| ccagcaatcg | gatttataaa | attttggaac | taaacgggta | cgatcccaa | tatgcggctt | 1260 |
| ccgtctttct | gggatgggcc | acgaaaaagt | tcggcaagag | gaacaccatc | tggctgtttg | 1320 |
| ggcctgcaac | taccgggaag | accaacatcg | cggaggccat | agcccacact | gtgcccttct | 1380 |
| acgggtgcgt | aaactggacc | aatgagaact | ttcccttcaa | cgactgtgtc | gacaagatgg | 1440 |
| tgatctggtg | ggaggagggg | aagatgaccg | ccaaggtcgt | ggagtcggcc | aaagccattc | 1500 |
| tcggaggaag | caaggtgcgc | gtggaccaga | aatgcaagtc | ctcggcccag | atagacccga | 1560 |
| ctcccgtgat | cgtcacctcc | aacaccaaca | tgtgcgccgt | gattgacggg | aactcaacga | 1620 |
| ccttcgaaca | ccagcagccg | ttgcaagacc | ggatgttcaa | atttgaactc | acccgccgtc | 1680 |
| tggatcatga | ctttgggaag | gtcaccaagc | aggaagtcaa | agacttttc | cggtgggcaa | 1740 |
| aggatcacgt | ggttgaggtg | gagcatgaat | tctacgtcaa | aaagggtgga | gccaagaaaa | 1800 |
| gacccgcccc | cagtgacgca | gatataagtg | agcccaaacg | ggtgcgcgag | tcagttgcgc | 1860 |
| agccatcgac | gtcagacgcg | gaagcttcga | tcaactacgc | agacaggtac | caaaacaaat | 1920 |
| gttctcgtca | cgtgggcatg | aatctgatgc | tgtttcctg | cagacaatgc | gagagaatga | 1980 |
| atcagagaatc | aaatatctgc | ttcactcacg | gacagaaaga | ctgtttagag | tgctttcccg | 2040 |
| tgtcagaatc | tcaacccgtt | tctgtcgtca | aaaaggcgta | tcagaaactg | tgctacattc | 2100 |

```
atcatatcat gggaaaggtg ccagacgctt gcactgcctg cgatctggtc aatgtggatt   2160
tggatgactg catctttgaa caataaatga tttaaatcag gtatggctgc cgatggttat   2220
cttccagatt ggctcgagga cactctctct gaaggaataa gacagtggtg gaagctcaaa   2280
cctggcccac caccaccaaa gcccgcagag cggcataagg acgacagcag gggtcttgtg   2340
cttcctgggt acaagtacct cggacccttc aacggactcg acaagggaga gccggtcaac   2400
gaggcagacg ccgcggccct cgagcacgta caaagcctac gaccggcagc tcgacagcgg   2460
agacaacccg tacctcaagt acaaccacgc cgacgcggag tttcaggagc gccttaaaga   2520
agatacgtct tttgggggca acctcggacg agcagtcttc caggcgaaaa agagggttct   2580
tgaacctctg ggcctggttg aggaacctgt taagacggct ccgggaaaaa agaggccggt   2640
agagcactct cctgtggagc cagactcctc ctcgggaacc ggaaaggcgg ccagcagcc   2700
tgcaagaaaa agattgaatt ttggtcagac tggagacgca gactcagtac ctgacccca   2760
gcctctcgga cagccaccag cagcccctc tggtctggga actaatacga tggctacagg   2820
cagtggcgca ccaatggcag acaataacga gggcgccgac ggagtgggta attcctccgg   2880
aaattggcat tgcgattcca catggatggg cgacagagtc atcaccacca gcacccgaac   2940
ctgggccctg cccacctaca caaccacct ctacaaacaa atttccagcc aatcaggagc   3000
ctcgaacgac aatcactact ttggctacag cacccttgg gggtattttg acttcaacag   3060
attccactgc cacttttcac cacgtgactg gcaaagactc atcaacaaca actggggatt   3120
ccgacccaag agactcaact tcaagctctt taacattcaa gtcaaagagg tcacgcagaa   3180
tgacggtacg acgacgattg ccaataacct taccagcacg gttcaggtgt ttactgactc   3240
ggagtaccag ctcccgtacg tcctcggctc ggcgcatcaa ggatgcctcc cgccgttccc   3300
agcagacgtc ttcatggtgc cacagtatgg atacctcacc ctgaacaacg ggagtcaggc   3360
agtaggacgc tcttcatttt actgcctgga gtactttcct tctcagatgc tgcgtaccgg   3420
aaacaacttt accttcagct acacttttga ggacgttcct ttccacagca gctacgctca   3480
cagccagagt ctggaccgtc tcatgaatcc tctcatcgac cagtacctgt attacttgag   3540
cagaacaaac actccaagtg gaaccaccac gcagtcaagg cttcagtttt ctcaggccgg   3600
agcgagtgac attcgggacc agtctaggaa ctggcttcct ggaccctgtt accgccagca   3660
gcgagtatca aagacatctg cggataacaa caacagtgaa tactcgtgga ctggagctac   3720
caagtaccac ctcaatggca gagactctct ggtgaatccg gccatggcaa gccacaagga   3780
cgatgaagaa aagttttttc ctcagagcgg ggttctcatc tttgggaagc aaggctcaga   3840
gaaacaaat gtgaacattg aaaaggtcat gattacagac gaagaggaaa tcggaacaac   3900
caatccgtg gctacggagc agtatggttc tgtatctacc aacctccaga gaggcaacag   3960
acaagcagct accgcagatg tcaacacaca aggcgttctt ccaggcatgg tctggcagga   4020
cagagatgtg taccttcagg ggcccatctg ggcaaagatt ccacacacgg acggacattt   4080
tcacccctct cccctcatgg gtggattcgg acttaaacac cctcctccac agattctcat   4140
caagaacacc ccggtacctg cgaatccttc gaccaccttc agtgcggcaa agtttgcttc   4200
cttcatcaca cagtactcca cgggacacgg tcagcgtgga gatcgagtgg gagctgcaga   4260
aggaaaacag caaacgctgg aatcccgaaa ttcagtacac ttccaactac aacaagtctg   4320
ttaatcgtgg acttaccgtg gatactaatg gcgtgtattc agagcctcgc cccattggca   4380
ccagatacct gactcgtaat ctgtaattgc ttgttaatca ataaaccgtt taattcgttt   4440
```

```
cagttgaact ttggtctctg cgtatttctt tcttatctag tttccatggc tacgtagata    4500
agtagcatgg cgggttaatc attaactaca aggaacccct agtgatgagg ttggccactc    4560
cctctctgcg cgctcgctcg ctcactgagg ccgggcgacc aaaggtcgcc cgacgcccgg    4620
gctttgcccg ggcggcctca gtgagcgagc gagcgcgcag agagggagtg gccaa         4675

<210> SEQ ID NO 27
<211> LENGTH: 4767
<212> TYPE: DNA
<213> ORGANISM: Artificial Sequence
<220> FEATURE:
<223> OTHER INFORMATION: Description of Artificial Sequence:  note =
      synthetic construct
<220> FEATURE:
<221> NAME/KEY: misc_feature
<222> LOCATION: 3009
<223> OTHER INFORMATION: n = a, c, t or g

<400> SEQUENCE: 27
ttggccactc cctctatgcg cgctcgctca ctcactcggc cctggagacc aaaggtctcc      60
agactgccgg cctctggccg gcagggccga gtgagtgagc gagcgcgcat agagggagtg     120
gccaactcca tcatctaggt ttgcccactg acgtcaatgt gacgtcctag ggttagggag     180
gtccctgtat tagcagtcac gtgagtgtcg tatttcgcgg agcgtagcgg agcgcatacc     240
aagctgccac gtcacagcca cgtggtccgt ttgcgacagt ttgcgacacc atgtggtcag     300
gagggtatat aaccgcgagt gagccagcga ggagctccat tttgcccgcg aattttgaac     360
gagcagcagc catgccgggg ttctacgaga tcgtgctgaa ggtgcccagc gacctggacg     420
agcacctgcc cggcatttct gactcttttg tgagctgggg ggccgagaag gaatgggagc     480
tgccgccgga ttctgacatg gacttgaatc tgattgagca ggcaccctg accgtggccg      540 aaaagctgca acgcgagttc ctggtcgagt ggcgccgcgt gagtaaggcc ccggaggccc     600
tcttctttgt ccagttcgag aaggggggaca gctacttcca cctgcacatc ctggtggaga     660
ccgtgggcgt caaatccatg gtggtgggcc gctacgtgag ccagattaaa gagaagctgg     720
tgacccgcat ctaccgcggg gtcgagccgc agcttcgaa ctggttcgcg gtgaccaaga      780
cgcgtaatgg cgccggaggc gggaacaagg tggtggacga ctgctacatc cccaactacc     840
tgctccccaa gacccagccc gagctccagt gggcgtggac taacatggac cagtatataa     900
gcgcctgttt gaatctcgcg gagcgtaaac ggctggtggc gcagcatctg acgcacgtgt     960
cgcagacgca ggagcagaac aaggaaaacc agaaccccaa ttctgacgcg ccggtcatca    1020
ggtcaaaaac ctccgccagg tacatggagc tggtcgggtg gctggtggac cgcgggatca    1080
cgtcagaaaa gcaatggatc caggaggacc aggcgtccta catctccttc aacgccgcct    1140
ccaactcgcg gtcacaaatc aaggccgcgc tggacaatgc ctccaaaatc atgagcctga    1200
caaagacggc tccggactac ctggtgggcc agaacccgcc ggaggacatt tccagcaacc    1260
gcatctaccg aatcctcgag atgaacgggt acgatccgca gtacgcgcc tccgtcttcc     1320 tgggctgggc gcaaaagaag ttcgggaaga ggaacaccat ctggctcttt gggccggcca    1380
cgacgggtaa aaccaacatc gcggaagcca tcgcccacgc cgtgcccttc tacggctgcg    1440
tgaactggac caatgagaac tttccgttca acgattgcgt cgacaagatg gtgatctggt    1500
gggaggaggg caagatgacg gccaaggtcg tagagagcgc caaggccatc ctgggcggaa    1560
gcaaggtgcg cgtggaccaa aagtgcaagt catcggccca gatcgaccca actcccgtga    1620
tcgtcacctc caacaccaac atgtgcgcgg tcatcgacgg aaactcgacc accttcgagc    1680
```

```
accaacaacc actccaggac cggatgttca agttcgagct caccaagcgc ctggagcacg   1740
actttggcaa ggtcaccaag caggaagtca aagactttt ccggtgggcg tcagatcacg    1800
tgaccgaggt gactcacgag ttttacgtca gaaagggtgg agctagaaag aggcccgccc   1860
ccaatgacgc agatataagt gagcccaagc gggcctgtcc gtcagttgcg cagccatcga   1920
cgtcagacgc ggaagctccg gtggactacg cggacaggta ccaaaacaaa tgttctcgtc   1980
acgtgggtat gaatctgatg ctttttccct gccggcaatg cgagagaatg aatcagaatg   2040
tggacatttg cttcacgcac ggggtcatgg actgtgccga gtgcttcccc gtgtcagaat   2100
ctcaacccgt gtctgtcgtc agaaagcgga cgtatcagaa actgtgtccg attcatcaca   2160
tcatggggag ggcgcccgag gtggcctgct cggcctgcga actggccaat gtggacttgg   2220
atgactgtga catggaacaa taaatgactc aaaccagata tgactgacgg ttaccttcca   2280
gattggctag aggacaacct ctctgaaggc gttcgagagt ggtgggcgct gcaacctgga   2340 gccctaaac ccaaggcaaa tcaacaacat caggacaacg ctcggggtct tgtgcttccg    2400
ggttacaaat acctcggacc cggcaacgga ctcgacaagg ggaacccgt caacgcagcg     2460 gacgcggcag ccctcgagca cgacaaggcc tacgaccagc agctcaaggc cggtgacaac   2520
ccctacctca gtacaaccca cgccgacgcg gagttccagc agcggcttca gggcgacaca   2580
ccgtttgggg gcaacctcgg cagagcagtc ttccaggcca aaagagggt tcttgaacct    2640 cttggtctgg ttgagcaagc gggtgagacg gctcctggaa agaagagacc gttgattgaa   2700
tccccccagc agcccgactc ctccacgggt atcggcaaaa aaggcaagca gccggctaaa   2760
aagaagctcg ttttcgaaga cgaaactgga gcaggcgacg gacccctga gggatcaact    2820 tccggagcca tgtctgatga cagtgagatg cgtgcagcag ctggcggagc tgcagtcgag   2880
ggsggacaag gtgccgatgg agtgggtaat gcctcgggtg attggcattg cgattccacc   2940
tggtctgagg gccacgtcac gaccaccagc accagaacct gggtcttgcc cacctacaac   3000
aaccacctnt acaagcgact cggagagagc ctgcagtcca acacctacaa cggattctcc   3060
accccctggg gatactttga cttcaaccgc ttccactgcc acttctcacc acgtgactgg   3120
cagcgactca tcaacaacaa ctggggcatg cgacccaaag ccatgcgggt caaaatcttc   3180
aacatccagg tcaaggaggt cacgacgtcg aacggcgaga caacggtggc taataacctt   3240
accagcacgg ttcagatctt tgcggactcg tcgtacgaac tgccgtacgt gatggatgcg   3300
ggtcaagagg gcagcctgcc tccttttccc aacgacgtct ttatggtgcc ccagtacggc   3360
tactgtggac tggtgaccgg caacacttcg cagcaacaga ctgacagaaa tgccttctac   3420
tgcctggagt acttccttc gcagatgctg cggactggca acaactttga aattacgtac   3480
agttttgaga aggtgccttt ccactcgatg tacgcgcaca gccagagcct ggaccggctg   3540
atgaaccctc tcatcgacca gtacctgtgg ggactgcaat cgaccaccac cggaaccacc   3600
ctgaatgccg ggactgccac caccaacttt accaagctgc ggcctaccaa cttttccaac   3660
tttaaaaaga actggctgcc cgggccttca atcaagcagc agggcttctc aaagactgcc   3720
aatcaaaact acaagatccc tgccaccggg tcagacagtc tcatcaaata cgagacgcac   3780
agcactctgg acgaagatg gagtgccctg acccccggac ctccaatggc cacggctgga   3840
cctgcggaca gcaagttcag caacagccag ctcatctttg cggggcctaa acagaacggc   3900
aacacggcca ccgtacccgg gactctgatc ttcacctctg aggaggagct ggcagccacc   3960
aacgccaccg atacggacat gtgggcaac ctacctggcg gtgaccagag caacagcaac    4020
ctgccgaccg tggacagact gacagccttg ggagccgtgc ctggaatggt ctggcaaaac   4080
```

-continued

```
agagacattt actaccaggg tcccatttgg gccaagattc ctcataccga tggacacttt    4140 caccccctcac cgctgattgg tgggtttggg ctgaaacacc cgcctcctca aattttatc    4200 aagaacaccc cggtacctgc gaatcctgca acgaccttca gctctactcc ggtaaactcc    4260
ttcattactc agtacagcac tggccaggtg tcggtgcaga ttgactggga gatccagaag    4320
gagcggtcca aacgctggaa ccccgaggtc cagtttacct ccaactacgg acagcaaaac    4380
tctctgttgt gggctcccga tgcggctggg aaatacactg agcctagggc tatcggtacc    4440
cgctacctca cccaccacct gtaataacct gttaatcaat aaaccggttt attcgtttca    4500
gttgaacttt ggtctccgtg tccttcttat cttatctcgt ttccatggct actgcgtaca    4560
taagcagcgg cctgcggcgc ttgcgcttcg cggtttacaa ctgccggtta atcagtaact    4620
tctggcaaac cagatgatgg agttggccac attagctatg cgcgctcgct cactcactcg    4680
gccctggaga ccaaaggtct ccagactgcc ggcctctggc cggcagggcc gagtgagtga    4740
gcgagcgcgc atagagggag tggccaa                                       4767
```

<210> SEQ ID NO 28
<211> LENGTH: 4652
<212> TYPE: DNA
<213> ORGANISM: Artificial Sequence
<220> FEATURE:
<223> OTHER INFORMATION: Description of Artificial Sequence: note = synthetic construct

<400> SEQUENCE: 28

```
tggcactctc ccccctgtcg cgttcgctcg ctcgctggct cgtttggggg ggtggcagct      60
caaagagctg ccagacgacg gccctctggc cgtcgccccc ccaaacgagc cagcgagcga     120
gcgaacgcga caggggggag agtgccacac tctcaagcaa gggggttttg taagcagtga     180
tgtcataatg atgtaatgct tattgtcacg cgatagttaa tgattaacag tcatgtgatg     240
tgttttatcc aataggaaga aagcgcgcgt atgagttctc gcgagacttc cggggtataa     300
aagaccgagt gaacgagccc gccgccattc tttgctctgg actgctagag gaccctcgct     360
gccatggcta ccttctatga agtcattgtt cgcgtcccat ttgacgtgga ggaacatctg     420
cctggaattt ctgacagctt tgtggactgg gtaactggtc aaatttggga gctgcctcca     480
gagtcagatt taaatttgac tctggttgaa cagcctcagt tgacggtggc tgatagaatt     540
cgccgcgtgt tcctgtacga gtggaacaaa ttttccaagc aggagtccaa attctttgtg     600
cagtttgaaa agggatctga atattttcat ctgcacacgc ttgtggagac ctccggcatc     660
tcttccatgg tcctcggccg ctacgtgagt cagattcgcg cccagctggt gaaagtggtc     720
ttccagggaa ttgaacccca gatcaacgac tgggtcgcca tcaccaaggt aaagaagggc     780
ggagccaata aggtggtgga ttctgggtat attcccgcct acctgctgcc gaaggtccaa     840
ccggagcttc agtgggcgtg gacaaacctg gacgagtata aattggccgc cctgaatctg     900
gaggagcgca acggctcgt cgcgcagttt ctggcagaat cctcgcagcg ctcgcaggag     960
gcggcttcgc agcgtgagtt ctcggctgac ccggtcatca aaagcaagac ttcccagaaa    1020
tacatgcgcg tcgtcaactg gctcgtggag cacggcatca cttccgagaa gcagtggatc    1080
caggaaaatc aggagagcta cctctccttc aactccaccg gcaactctcg gagccagatc    1140
aaggccgcgc tcgacaacgc gaccaaaatt atgagtctga caaaaagcgc ggtggactac    1200
ctcgtgggga gctccgttcc cgaggacatt tcaaaaaaca gaatctggca aattttttgag    1260 atgaatggct acgacccggc ctacgcggga tccatcctct acgctggtg tcagcgctcc    1320
```

```
ttcaacaaga ggaacaccgt ctggctctac ggacccgcca cgaccggcaa gaccaacatc    1380
gcggaggcca tcgcccacac tgtgcccttt tacggctgcg tgaactggac caatgaaaac    1440 tttccctta atgactgtgt ggacaaaatg ctcatttggt gggaggaggg aaagatgacc     1500
aacaaggtgg ttgaatccgc caaggccatc ctgggggct caaaggtgcg ggtcgatcag     1560
aaatgtaaat cctctgttca aattgattct accccctgtca ttgtaacttc aatacaaac   1620 atgtgtgtgg tggtggatgg gaattccacg acctttgaac accagcagcc gctgaggac    1680 cgcatgttca aatttgaact gactaagcgg ctcccgccag attttggcaa gattactaag    1740
caggaagtca aggactttt tgcttgggca aaggtcaatc aggtgccggt gactcacgag     1800
tttaaagttc ccagggaatt ggcgggaact aaaggggcgg agaaatctct aaaacgccca    1860
ctgggtgacg tcaccaatac tagctataaa agtctggaga gcgggccag gctctcattt     1920 gttcccgaga cgcctcgcag ttcagacgtg actgttgatc ccgctcctct gcgaccgctc    1980
aattggaatt caaggtatga ttgcaaatgt gactatcatg ctcaatttga caacatttct    2040
aacaaatgtg atgaatgtga atatttgaat cggggcaaaa atggatgtat ctgtcacaat    2100
gtaactcact gtcaaatttg tcatgggatt ccccccctggg aaaaggaaaa cttgtcagat   2160
tttggggatt ttgacgatgc caataaagaa cagtaaataa agcgagtagt catgtctttt    2220
gttgatcacc ctccagattg gttggaagaa gttggtgaag gtcttcgcga gtttttgggc    2280
cttgaagcgg gccaccgaa accaaaaccc aatcagcagc atcaagatca agcccgtggt     2340
cttgtgctgc ctggttataa ctatctcgga cccggaaacg gtctcgatcg aggagagcct    2400
gtcaacaggg cagacgaggt cgcgcgagag cacgacatct cgtacaacga gcagcttgag    2460
gcgggagaca ccccctacct caagtacaac cacgcggacg ccgagtttca ggagaagctc    2520
gccgacgaca catccttcgg gggaaacctc ggaaaggcag tctttcaggc caagaaaagg    2580
gttctcgaac cttttggcct ggttgaagag ggtgctaaga cggcccctac cggaaagcgg    2640
atagacgacc actttccaaa aagaaagaag gctcggaccg aagaggactc caagccttcc    2700
acctcgtcag acgccgaagc tggacccagc ggatcccagc agctgcaaat cccagcccaa    2760
ccagcctcaa gtttgggagc tgatacaatg tctgcgggag gtggcggccc attgggcgac    2820
aataaccaag gtgccgatgg agtgggcaat gcctcgggag attggcattg cgattccacg    2880
tggatggggg acagagtcgt caccaagtcc acccgaacct gggtgctgcc cagctacaac    2940
aaccaccagt accgagagat caaaagcggc tccgtcgacg aagcaacgc caacgcctac    3000 tttggataca gcacccccctg ggggtacttt gactttaacc gcttccacag ccactggagc   3060
ccccgagact ggcaaagact catcaacaac tactggggct tcagaccccg gtccctcaga    3120
gtcaaaatct tcaacattca agtcaaagag gtcacggtgc aggactccac caccaccatc   3180
gccaacaacc tcacctccac cgtccaagtg tttacggacg acgactacca gctgccctac    3240
gtcgtcggca acgggaccga gggatgcctg ccggccttcc ctccgcaggt ctttacgctg    3300
ccgcagtacg gttacgcgac gctgaaccgc gacaacacag aaaatcccac cgagaggagc    3360
agcttcttct gcctagagta ctttcccagc aagatgctga acgggcaa caactttgag     3420 tttacctaca actttgagga ggtgcccttc cactccagct cgctcccag tcagaacctg    3480 ttcaagctgg ccaacccgct ggtggaccag tacttgtacc gcttcgtgag cacaaataac    3540
actggcggag tccagttcaa caagaacctg gcgggagat acgccaacac ctacaaaaac    3600
tggttcccgg ggcccatggg ccgaacccag ggctggaacc tgggctccgg ggtcaaccgc    3660
```

```
gccagtgtca gcgccttcgc cacgaccaat aggatggagc tcgagggcgc gagttaccag   3720
gtgcccccgc agccgaacgg catgaccaac aacctccagg gcagcaacac ctatgccctg   3780
gagaacacta tgatcttcaa cagccagccg gcgaacccgg gcaccaccgc cacgtacctc   3840
gagggcaaca tgctcatcac cagcgagagc gagacgcagc cggtgaaccg cgtggcgtac   3900
aacgtcggcg ggcagatggc caccaacaac cagagctcca ccactgcccc cgcgaccggc   3960
acgtacaacc tccaggaaat cgtgcccggc agcgtgtgga tggagaggga cgtgtacctc   4020
caaggaccca tctgggccaa gatcccagag acggggcgc actttcaccc ctctccggcc   4080
atgggcggat tcggactcaa acacccaccg cccatgatgc tcatcaagaa cacgcctgtg   4140
cccggaaata tcaccagctt ctcggacgtg cccgtcagca gcttcatcac ccagtacagc   4200
accgggcagg tcaccgtgga gatggagtgg gagctcaaga aggaaaactc caagaggtgg   4260
aacccagaga tccagtacac aaacaactac aacgaccccc agtttgtgga ctttgccccg   4320
gacagcaccg gggaatacag aaccaccaga cctatcggaa cccgatacct acccgaccc   4380 cttaacccca ttcatgtcgc ataccctcaa taaaccgtgt attcgtgtca gtaaaatact   4440
gcctcttgtg gtcattcaat gaataacagc ttacaacatc tacaaaacct ccttgcttga   4500
gagtgtggca ctctcccccc tgtcgcgttc gctcgctcgc tggctcgttt ggggggtgg   4560 cagctcaaag agctgccaga cgacggccct ctggccgtcg ccccccaaa cgagccagcg   4620 agcgagcgaa cgcgacaggg gggagagtgc ca                                4652
```

<210> SEQ ID NO 29
<211> LENGTH: 621
<212> TYPE: PRT
<213> ORGANISM: Artificial Sequence
<220> FEATURE:
<223> OTHER INFORMATION: Description of Artificial Sequence: note = synthetic construct

<400> SEQUENCE: 29

```
Met Pro Gly Phe Tyr Glu Ile Val Ile Lys Val Pro Ser Asp Leu Asp
  1               5                  10                  15

Gly His Leu Pro Gly Ile Ser Asp Ser Phe Val Asn Trp Val Ala Glu
             20                  25                  30

Lys Glu Trp Glu Leu Pro Pro Asp Ser Asp Met Asp Leu Asn Leu Ile
         35                  40                  45

Glu Gln Ala Pro Leu Thr Val Ala Glu Lys Leu Gln Arg Asp Phe Leu
     50                  55                  60

Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                 85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
```

```
                180                 185                 190
Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
            245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
            290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
            370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
            485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
            530                 535                 540

Phe Pro Val Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
            565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
            595                 600                 605
```

```
Leu Val Asn Val Asp Leu Asp Asp Cys Ile Phe Glu Gln
610                 615                 620
```

<210> SEQ ID NO 30
<211> LENGTH: 735
<212> TYPE: PRT
<213> ORGANISM: Artificial Sequence
<220> FEATURE:
<223> OTHER INFORMATION: Description of Artificial Sequence:  note = synthetic construct

<400> SEQUENCE: 30

```
Met Ala Ala Asp Gly Tyr Leu Pro Asp Trp Leu Glu Asp Thr Leu Ser
 1               5                  10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
```

```
                  340                 345                 350
Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 31
<211> LENGTH: 623
<212> TYPE: PRT
<213> ORGANISM: Artificial Sequence
```

<220> FEATURE:
<223> OTHER INFORMATION: Description of Artificial Sequence:  note = synthetic construct

<400> SEQUENCE: 31

```
Met Pro Gly Phe Tyr Glu Ile Val Leu Lys Val Pro Ser Asp Leu Asp
 1               5                  10                  15
Glu His Leu Pro Gly Ile Ser Asp Ser Phe Val Ser Trp Val Ala Glu
            20                  25                  30
Lys Glu Trp Glu Leu Pro Pro Asp Ser Asp Met Asp Leu Asn Leu Ile
        35                  40                  45
Glu Gln Ala Pro Leu Thr Val Ala Glu Lys Leu Gln Arg Glu Phe Leu
 50                  55                  60
Val Glu Trp Arg Arg Val Ser Lys Ala Pro Glu Ala Leu Phe Phe Val
 65                  70                  75                  80
Gln Phe Glu Lys Gly Asp Ser Tyr Phe His Leu His Ile Leu Val Glu
                85                  90                  95
Thr Val Gly Val Lys Ser Met Val Gly Arg Tyr Val Ser Gln Ile
            100                 105                 110
Lys Glu Lys Leu Val Thr Arg Ile Tyr Arg Gly Val Glu Pro Gln Leu
        115                 120                 125
Pro Asn Trp Phe Ala Val Thr Lys Thr Arg Asn Gly Ala Gly Gly Gly
130                 135                 140
Asn Lys Val Val Asp Asp Cys Tyr Ile Pro Asn Tyr Leu Leu Pro Lys
145                 150                 155                 160
Thr Gln Pro Glu Leu Gln Trp Ala Trp Thr Asn Met Asp Gln Tyr Ile
                165                 170                 175
Ser Ala Cys Leu Asn Leu Ala Glu Arg Lys Arg Leu Val Ala Gln His
            180                 185                 190
Leu Thr His Val Ser Gln Thr Gln Glu Gln Asn Lys Glu Asn Gln Asn
        195                 200                 205
Pro Asn Ser Asp Ala Pro Val Ile Arg Ser Lys Thr Ser Ala Arg Tyr
210                 215                 220
Met Glu Leu Val Gly Trp Leu Val Asp Arg Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Ser Lys
            260                 265                 270
Ile Met Ser Leu Thr Lys Thr Ala Pro Asp Tyr Leu Val Gly Gln Asn
        275                 280                 285
Pro Pro Glu Asp Ile Ser Ser Asn Arg Ile Tyr Arg Ile Leu Glu Met
290                 295                 300
Asn Gly Tyr Asp Pro Gln Tyr Ala Ala Ser Val Phe Leu Gly Trp Ala
305                 310                 315                 320
Gln Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Ala Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
370                 375                 380
Lys Val Val Glu Ser Ala Lys Ala Ile Leu Gly Gly Ser Lys Val Arg
```

```
                385                 390                 395                 400
Val Asp Gln Lys Cys Lys Ser Ser Ala Gln Ile Asp Pro Thr Pro Val
                    405                 410                 415

Ile Val Thr Ser Asn Thr Asn Met Cys Ala Val Ile Asp Gly Asn Ser
                    420                 425                 430

Thr Thr Phe Glu His Gln Gln Pro Leu Gln Asp Arg Met Phe Lys Phe
                    435                 440                 445

Glu Leu Thr Lys Arg Leu Glu His Asp Phe Gly Lys Val Thr Lys Gln
            450                 455                 460

Glu Val Lys Asp Phe Phe Arg Trp Ala Ser Asp His Val Thr Glu Val
465                 470                 475                 480

Thr His Glu Phe Tyr Val Arg Lys Gly Gly Ala Arg Lys Arg Pro Ala
                    485                 490                 495

Pro Asn Asp Ala Asp Ile Ser Glu Pro Lys Arg Ala Cys Pro Ser Val
                    500                 505                 510

Ala Gln Pro Ser Thr Ser Asp Ala Glu Ala Pro Val Asp Tyr Ala Asp
                    515                 520                 525

Arg Tyr Gln Asn Lys Cys Ser Arg His Val Gly Met Asn Leu Met Leu
            530                 535                 540

Phe Pro Cys Arg Gln Cys Glu Arg Met Asn Gln Asn Val Asp Ile Cys
545                 550                 555                 560

Phe Thr His Gly Val Met Asp Cys Ala Glu Cys Phe Pro Val Ser Glu
                    565                 570                 575

Ser Gln Pro Val Ser Val Val Arg Lys Arg Thr Tyr Gln Lys Leu Cys
                    580                 585                 590

Pro Ile His His Ile Met Gly Arg Ala Pro Glu Val Ala Cys Ser Ala
                    595                 600                 605

Cys Glu Leu Ala Asn Val Asp Leu Asp Asp Cys Asp Met Glu Gln
            610                 615                 620

<210> SEQ ID NO 32
<211> LENGTH: 734
<212> TYPE: PRT
<213> ORGANISM: Artificial Sequence
<220> FEATURE:
<223> OTHER INFORMATION: Description of Artificial Sequence:  note =
      synthetic construct

<400> SEQUENCE: 32

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
                20                  25                  30

Ala Asn Gln Gln His Gln Asp Asn Ala Arg Gly Leu Val Leu Pro Gly
            35                  40                  45

Tyr Lys Tyr Leu Gly Pro Gly Asn Gly Leu Asp Lys Gly Glu Pro Val
        50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125
```

-continued

```
Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Leu Val Phe Glu Asp Glu Thr
                165                 170                 175

Gly Ala Gly Asp Gly Pro Pro Glu Gly Ser Thr Ser Gly Ala Met Ser
                180                 185                 190

Asp Asp Ser Glu Met Arg Ala Ala Gly Gly Ala Ala Val Glu Gly
            195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
    275                 280                 285

Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
    355                 360                 365

Cys Gly Leu Val Thr Gly Asn Thr Ser Gln Gln Thr Asp Arg Asn
    370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
    435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
    515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
```

```
                        545                 550                 555                 560
                    Glu Glu Glu Leu Ala Ala Thr Asn Ala Thr Asp Thr Asp Met Trp Gly
                                        565                 570                 575

Asn Leu Pro Gly Gly Asp Gln Ser Asn Ser Asn Leu Pro Thr Val Asp
                                        580                 585                 590

Arg Leu Thr Ala Leu Gly Ala Val Pro Gly Met Val Trp Gln Asn Arg
                                        595                 600                 605

Asp Ile Tyr Tyr Gln Gly Pro Ile Trp Ala Lys Ile Pro His Thr Asp
                                        610                 615                 620

Gly His Phe His Pro Ser Pro Leu Ile Gly Gly Phe Gly Leu Lys His
                    625                 630                 635                 640

Pro Pro Pro Gln Ile Phe Ile Lys Asn Thr Pro Val Pro Ala Asn Pro
                                        645                 650                 655

Ala Thr Thr Phe Ser Ser Thr Pro Val Asn Ser Phe Ile Thr Gln Tyr
                                        660                 665                 670

Ser Thr Gly Gln Val Ser Val Gln Ile Asp Trp Glu Ile Gln Lys Glu
                                        675                 680                 685

Arg Ser Lys Arg Trp Asn Pro Glu Val Gln Phe Thr Ser Asn Tyr Gly
                                        690                 695                 700

Gln Gln Asn Ser Leu Leu Trp Ala Pro Asp Ala Ala Gly Lys Tyr Thr
                    705                 710                 715                 720

Glu Pro Arg Ala Ile Gly Thr Arg Tyr Leu Thr His His Leu
                                        725                 730

<210> SEQ ID NO 33
<211> LENGTH: 610
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 33

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
        50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
                100                 105                 110

Ala Gln Leu Val Lys Val Val Phe Gln Gly Ile Glu Pro Gln Ile Asn
            115                 120                 125

Asp Trp Val Ala Ile Thr Lys Val Lys Lys Gly Gly Ala Asn Lys Val
        130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175
```

```
Leu Asn Leu Glu Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
            195                 200                 205

Asp Pro Val Ile Lys Ser Lys Thr Ser Gln Lys Tyr Met Ala Leu Val
            210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
            245                 250                 255

Ser Gln Ile Lys Ala Ala Leu Asp Asn Ala Thr Lys Ile Met Ser Leu
            260                 265                 270

Thr Lys Ser Ala Val Asp Tyr Leu Val Gly Ser Ser Val Pro Glu Asp
            275                 280                 285

Ile Ser Lys Asn Arg Ile Trp Gln Ile Phe Glu Met Asn Gly Tyr Asp
            290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
            325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
            355                 360                 365

Met Leu Ile Trp Trp Glu Glu Gly Lys Met Thr Asn Lys Val Val Glu
            370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
            405                 410                 415

Asn Thr Asn Met Cys Val Val Asp Gly Asn Ser Thr Thr Phe Glu
            420                 425                 430

His Gln Gln Pro Leu Glu Asp Arg Met Phe Lys Phe Glu Leu Thr Lys
            435                 440                 445

Arg Leu Pro Pro Asp Phe Gly Lys Ile Thr Lys Gln Glu Val Lys Asp
450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
            485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
            515                 520                 525

Val Thr Val Asp Pro Ala Pro Leu Arg Pro Leu Asn Trp Asn Ser Arg
            530                 535                 540

Tyr Asp Cys Lys Cys Asp Tyr His Ala Gln Phe Asp Asn Ile Ser Asn
545                 550                 555                 560

Lys Cys Asp Glu Cys Glu Tyr Leu Asn Arg Gly Lys Asn Gly Cys Ile
            565                 570                 575

Cys His Asn Val Thr His Cys Gln Ile Cys His Gly Ile Pro Pro Trp
            580                 585                 590

Glu Lys Glu Asn Leu Ser Asp Phe Gly Asp Phe Asp Asp Ala Asn Lys
```

```
                    595                 600                 605

Glu Gln
    610

<210> SEQ ID NO 34
<211> LENGTH: 724
<212> TYPE: PRT
<213> ORGANISM: Artificial Sequence
<220> FEATURE:
<223> OTHER INFORMATION: Description of Artificial Sequence:  note =
      synthetic construct

<400> SEQUENCE: 34

Met Ser Phe Val Asp His Pro Pro Asp Trp Leu Glu Glu Val Gly Glu
 1               5                  10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335
```

```
Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
    355                 360                 365

Ala Thr Leu Asn Arg Asp Asn Thr Glu Asn Pro Thr Glu Arg Ser Ser
370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
            435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
            515                 520                 525

Phe Asn Ser Gln Pro Ala Asn Pro Gly Thr Thr Ala Thr Tyr Leu Glu
530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
    595                 600                 605

Ala Lys Ile Pro Glu Thr Gly Ala His Phe His Pro Ser Pro Ala Met
610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 35
<211> LENGTH: 627
<212> TYPE: PRT
<213> ORGANISM: Artificial Sequence
```

-continued

<220> FEATURE:
<223> OTHER INFORMATION: Description of Artificial Sequence: note = synthetic construct

<400> SEQUENCE: 35

```
Met Ala Leu Ser Arg Pro Leu Gln Ile Ser Ser Asp Lys Phe Tyr Glu
  1               5                  10                  15

Val Ile Ile Arg Leu Ser Ser Asp Ile Asp Gln Asp Val Pro Gly Leu
             20                  25                  30

Ser Leu Asn Phe Val Glu Trp Leu Ser Thr Gly Val Trp Glu Pro Thr
         35                  40                  45

Gly Ile Trp Asn Met Glu His Val Asn Leu Pro Met Val Thr Leu Ala
 50                  55                  60

Glu Lys Ile Lys Asn Ile Phe Ile Gln Arg Trp Asn Gln Phe Asn Gln
 65                  70                  75                  80

Asp Glu Thr Asp Phe Phe Gln Leu Glu Glu Gly Ser Glu Tyr Ile
                 85                  90                  95

His Leu His Cys Cys Ile Ala Gln Gly Asn Val Arg Ser Phe Val Leu
                100                 105                 110

Gly Arg Tyr Met Ser Gln Ile Lys Asp Ser Ile Ile Arg Asp Val Tyr
            115                 120                 125

Glu Gly Lys Gln Ile Lys Ile Pro Asp Trp Phe Ala Ile Thr Lys Thr
        130                 135                 140

Lys Arg Gly Gly Gln Asn Lys Thr Val Thr Ala Ala Tyr Ile Leu His
145                 150                 155                 160

Tyr Leu Ile Pro Lys Lys Gln Pro Glu Leu Gln Trp Ala Phe Thr Asn
                165                 170                 175

Met Pro Leu Phe Thr Ala Ala Leu Cys Leu Gln Lys Arg Gln Glu
                180                 185                 190

Leu Leu Asp Ala Phe Gln Glu Ser Asp Leu Ala Ala Pro Leu Pro Asp
            195                 200                 205

Pro Gln Ala Ser Thr Val Ala Pro Leu Ile Ser Asn Arg Ala Ala Lys
        210                 215                 220

Asn Tyr Ser Asn Leu Val Asp Trp Leu Ile Glu Met Gly Ile Thr Ser
225                 230                 235                 240

Glu Lys Gln Trp Leu Thr Glu Asn Arg Glu Ser Tyr Arg Ser Phe Gln
                245                 250                 255

Ala Thr Ser Ser Asn Asn Arg Gln Val Lys Ala Ala Leu Glu Asn Ala
            260                 265                 270

Arg Ala Glu Met Leu Leu Thr Lys Thr Ala Thr Asp Tyr Leu Ile Gly
        275                 280                 285

Lys Asp Pro Val Leu Asp Ile Thr Lys Asn Arg Val Tyr Gln Ile Leu
    290                 295                 300

Lys Met Asn Asn Tyr Asn Pro Gln Tyr Ile Gly Ser Ile Leu Cys Gly
305                 310                 315                 320

Trp Val Lys Arg Glu Phe Asn Lys Arg Asn Ala Ile Trp Leu Tyr Gly
                325                 330                 335

Pro Ala Thr Thr Gly Lys Thr Asn Ile Ala Glu Ala Ile Ala His Ala
            340                 345                 350

Val Pro Phe Tyr Gly Cys Val Asn Trp Thr Asn Glu Asn Phe Pro Phe
        355                 360                 365

Asn Asp Cys Val Asp Lys Met Leu Ile Trp Trp Glu Glu Gly Lys Met
    370                 375                 380

Thr Asn Lys Val Val Glu Ser Ala Lys Ala Ile Leu Gly Gly Ser Ala
```

```
            385                 390                 395                 400
Val Arg Val Asp Gln Lys Cys Lys Gly Ser Val Cys Ile Glu Pro Thr
                405                 410                 415

Pro Val Ile Ile Thr Ser Asn Thr Asp Met Cys Met Ile Val Asp Gly
                420                 425                 430

Asn Ser Thr Thr Met Glu His Arg Ile Pro Leu Glu Arg Met Phe
                435                 440                 445

Gln Ile Val Leu Ser His Lys Leu Gly Pro Ser Phe Gly Lys Ile Ser
        450                 455                 460

Lys Lys Glu Val Arg Glu Phe Phe Lys Trp Ala Asn Asp Asn Leu Val
465                 470                 475                 480

Pro Val Val Ser Glu Phe Lys Val Arg Thr Asn Gln Thr Asn Leu
                485                 490                 495

Pro Glu Pro Val Pro Glu Arg Ala Asn Glu Pro Glu Pro Pro Lys
                500                 505                 510

Ile Trp Ala Pro Pro Thr Arg Glu Glu Leu Glu Glu Leu Leu Arg Ala
                515                 520                 525

Ser Pro Glu Leu Phe Ser Ser Val Ala Pro Ile Pro Val Thr Pro Gln
        530                 535                 540

Asn Ser Pro Glu Pro Lys Arg Ser Arg Asn Asn Tyr Gln Val Arg Cys
545                 550                 555                 560

Ala Leu His Thr Tyr Asp Asn Ser Met Asp Val Phe Glu Cys Met Glu
                565                 570                 575

Cys Glu Lys Ala Asn Phe Pro Glu Phe Gln Pro Leu Gly Glu Asn Tyr
                580                 585                 590

Cys Asp Glu His Gly Trp Tyr Asp Cys Ala Ile Cys Lys Glu Leu Lys
                595                 600                 605

Asn Glu Leu Ala Glu Ile Glu His Val Phe Glu Leu Asp Asp Ala Glu
        610                 615                 620

Asn Glu Gln
625

<210> SEQ ID NO 36
<211> LENGTH: 732
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 36

Met Ser Thr Phe Leu Asp Ser Phe Glu Glu Trp Tyr Glu Thr Ala Ala
1               5                   10                  15

Ala Ser Trp Arg Asn Leu Lys Ala Gly Ala Pro Gln Pro Lys Pro Asn
                20                  25                  30

Gln Gln Ser Gln Ser Val Ser Pro Asp Arg Glu Pro Glu Arg Lys Asp
        35                  40                  45

Asn Asn Arg Gly Phe Val Leu Pro Gly Tyr Lys Tyr Leu Gly Pro Gly
50                  55                  60

Asn Gly Leu Asp Lys Gly Pro Pro Val Asn Lys Ala Asp Ser Val Ala
65                  70                  75                  80

Leu Glu His Asp Lys Ala Tyr Asp Gln Gln Leu Lys Ala Gly Asp Asn
                85                  90                  95

Pro Tyr Ile Lys Phe Asn His Ala Asp Gln Asp Phe Ile Asp Ser Leu
                100                 105                 110
```

Gln Asp Asp Gln Ser Phe Gly Gly Asn Leu Gly Lys Ala Val Phe Gln
            115                 120                 125

Ala Lys Lys Arg Ile Leu Glu Pro Phe Gly Leu Val Glu Asp Pro Val
            130                 135                 140

Asn Thr Ala Pro Ala Lys Lys Asn Thr Gly Lys Leu Thr Asp His Tyr
145                 150                 155                 160

Pro Val Val Lys Lys Pro Lys Leu Thr Glu Val Ser Ala Gly Gly
            165                 170                 175

Gly Ser Ser Ala Val Gln Asp Gly Gly Ala Thr Ala Glu Gly Thr Glu
            180                 185                 190

Pro Val Ala Ala Ser Glu Met Ala Glu Gly Gly Gly Ala Met Gly
            195                 200                 205

Asp Ser Ser Gly Gly Ala Asp Gly Val Gly Asn Ala Ser Gly Asn Trp
            210                 215                 220

His Cys Asp Ser Gln Trp Met Gly Asn Thr Val Ile Thr Lys Thr Thr
225                 230                 235                 240

Arg Thr Trp Val Leu Pro Ser Tyr Asn His Ile Tyr Lys Ala Ile
            245                 250                 255

Thr Ser Gly Thr Ser Gln Asp Ala Asn Val Gln Tyr Ala Gly Tyr Ser
            260                 265                 270

Thr Pro Trp Gly Tyr Phe Asp Phe Asn Arg Phe His Cys His Phe Ser
            275                 280                 285

Pro Arg Asp Trp Gln Arg Leu Ile Asn Asn His Trp Gly Ile Arg Pro
            290                 295                 300

Lys Ser Leu Lys Phe Lys Ile Phe Asn Val Gln Val Lys Glu Val Thr
305                 310                 315                 320

Thr Gln Asp Gln Thr Lys Thr Ile Ala Asn Asn Leu Thr Ser Thr Ile
            325                 330                 335

Gln Val Phe Thr Asp Asp Glu His Gln Leu Pro Tyr Val Leu Gly Ser
            340                 345                 350

Ala Thr Glu Gly Thr Met Pro Pro Phe Pro Ser Asp Val Tyr Ala Leu
            355                 360                 365

Pro Gln Tyr Gly Tyr Cys Thr Met His Thr Asn Gln Asn Gly Ala Arg
            370                 375                 380

Phe Asn Asp Arg Ser Ala Phe Tyr Cys Leu Glu Tyr Phe Pro Ser Gln
385                 390                 395                 400

Met Leu Arg Thr Gly Asn Asn Phe Glu Phe Thr Phe Asp Phe Glu Glu
            405                 410                 415

Val Pro Phe His Ser Met Phe Ala His Ser Gln Asp Leu Asp Arg Leu
            420                 425                 430

Met Asn Pro Leu Val Asp Gln Tyr Leu Trp Asn Phe Asn Glu Val Asp
            435                 440                 445

Ser Ser Arg Asn Ala Gln Phe Lys Lys Ala Val Lys Gly Ala Tyr Gly
            450                 455                 460

Thr Met Gly Arg Asn Trp Leu Pro Gly Pro Lys Phe Leu Asp Gln Arg
465                 470                 475                 480

Val Arg Ala Tyr Thr Gly Gly Thr Asp Asn Tyr Ala Asn Trp Asn Ile
            485                 490                 495

Trp Ser Asn Gly Asn Lys Val Asn Leu Lys Asp Arg Gln Tyr Leu Leu
            500                 505                 510

Gln Pro Gly Pro Val Ser Ala Thr Tyr Thr Glu Gly Glu Ala Ser Ser
            515                 520                 525

Leu Pro Ala Gln Asn Ile Leu Gly Ile Ala Lys Asp Pro Tyr Arg Ser

```
                530                 535                 540
Gly Ser Thr Thr Ala Gly Ile Ser Asp Ile Met Val Thr Glu Glu Gln
545                 550                 555                 560

Glu Val Ala Pro Thr Asn Gly Val Gly Trp Lys Pro Tyr Gly Arg Thr
                565                 570                 575

Val Thr Asn Glu Gln Asn Thr Thr Thr Ala Pro Thr Ser Ser Asp Leu
            580                 585                 590

Asp Val Leu Gly Ala Leu Pro Gly Met Val Trp Gln Asn Arg Asp Ile
        595                 600                 605

Tyr Leu Gln Gly Pro Ile Gly Ala Lys Ile Pro Lys Thr Asp Gly Lys
    610                 615                 620

Phe His Pro Ser Pro Asn Leu Gly Gly Phe Gly Leu His Asn Pro Pro
625                 630                 635                 640

Pro Gln Val Phe Ile Lys Asn Thr Pro Val Pro Ala Asp Pro Pro Val
                645                 650                 655

Glu Tyr Val His Gln Lys Trp Asn Ser Tyr Ile Thr Gln Tyr Ser Thr
            660                 665                 670

Gly Gln Cys Thr Val Glu Met Val Trp Glu Leu Arg Lys Glu Asn Ser
        675                 680                 685

Lys Arg Trp Asn Pro Glu Ile Gln Phe Thr Ser Asn Phe Ser Asn Arg
    690                 695                 700

Thr Ser Ile Met Phe Ala Pro Asn Glu Thr Gly Gly Tyr Val Glu Asp
705                 710                 715                 720

Arg Leu Ile Gly Thr Arg Tyr Leu Thr Gln Asn Leu
                725                 730

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence:  note =
      synthetic construct

<400> SEQUENCE: 37

Pro Ser Gly Gly Asp Asn Asn Asn Lys Phe
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:  note =
      synthetic construct

<400> SEQUENCE: 38

Gln Gly Pro Ser Gly Gly Asp
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence:  note =
      synthetic construct

<400> SEQUENCE: 39

Asn Asn Asn Lys Phe
1               5
```

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: note = synthetic construct

<400> SEQUENCE: 40

Val Ser Gln Ala Gly Ser Ser Gly Arg Ala
 1               5                  10

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: note = synthetic construct

<400> SEQUENCE: 41
cgtctttgag tcttccacca gaccaaag                                        28

<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence: note = synthetic construct

<400> SEQUENCE: 42
cactgcagca cctgctacta ccacaagagc gctccgaccg gagacaagcg                50

<210> SEQ ID NO 43
<211> LENGTH: 76
<212> TYPE: DNA
<213> ORGANISM: Artificial Sequence
<220> FEATURE:
<223> OTHER INFORMATION: Description of Artificial Sequence: note = synthetic construct

<400> SEQUENCE: 43
caaccacctg tacaaacgaa tccactgcag cacctgctac taccacaaga gcaacaacaa    60
caaattcttt ggattc                                                    76

<210> SEQ ID NO 44
<211> LENGTH: 76
<212> TYPE: DNA
<213> ORGANISM: Artificial Sequence
<220> FEATURE:
<223> OTHER INFORMATION: Description of Artificial Sequence: note = synthetic construct

<400> SEQUENCE: 44
gaatccaaag aatttgttgt tgttgctctt gtggtagtag caggtgctgc agtggattcg    60
tttgtacagg tggttg                                                    76

<210> SEQ ID NO 45
<211> LENGTH: 61
<212> TYPE: DNA
<213> ORGANISM: Artificial Sequence
<220> FEATURE:
<223> OTHER INFORMATION: Description of Artificial Sequence: note = synthetic construct -continued

<400> SEQUENCE: 45
caaacgaatc caaggacact gcagcacctg ctactaccac aagagctttg gattcagcac    60
c    61

<210> SEQ ID NO 46
<211> LENGTH: 61
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 46
ggtgctgaat ccaaagctct tgtggtagta gcaggtgctg cagtgtcctt ggattcgttt    60
g    61

<210> SEQ ID NO 47
<211> LENGTH: 71
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 47
tacctctggg ctttcagctc ccactgcagc acctgctact accacaagag ccttcattac    60
tcgcgggcga c    71

<210> SEQ ID NO 48
<211> LENGTH: 71
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 48
gtcgcccgcg agtaatgaag gctcttgtgg tagtagcagg tgctgcagtg ggagctgaaa    60
gcccagaggt a    71

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 49

Asn Gly Arg Ala His Ala
 1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 50

Ser Ile Gly Tyr Pro Leu Pro
 1               5

```
<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 51

Cys Gly Phe Glu Cys Val Arg Gln Cys Pro Glu Arg Cys
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 52

Ala Ser Ser Leu Asn Ile Ala
1               5

<210> SEQ ID NO 53
<211> LENGTH: 22
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 53

Asn Ile Ser Leu Asp Asn Pro Leu Glu Asn Pro Ser Ser Leu Phe Asp
1               5                   10                  15

Leu Val Ala Arg Ile Lys
            20

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 54

Lys Phe Asn Lys Pro Phe Val Phe Leu Ile
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 55

Arg Glu Thr Ala Asn Glu Phe
1               5
```

AVIAN ADENOASSOCIATED VIRUS AND USES THEREOF

The present application is a 35 U.S.C. §371 national phase application from, and claims priority to, international application PCT/US04/15534, filed May 18, 2004 (published under PCT Article 21(2) in English), which claims priority to U.S. provisional patent application Ser. No. 60/472,066, filed May 19, 2004, which applications are incorporated herein in their entirety by reference.

BACKGROUND OF THE INVENTION

1. Field of the Invention

The present invention provides avian adeno-associated virus (AAAV) and vectors derived therefrom. Thus, the present invention relates to AAAV vectors for and methods of delivering nucleic acids to cells of subjects.

2. Background Art

To date, eight AAV isolates ($AAVR_{1-8}$) have been, characterized and sequenced (2, 4, 19, 20, 25, 32, 51, 56) with AAV2 being the most extensively studied. AAV virions are approximately 20-25 nm in diameter and are composed of a mixture of assembled proteins (VPs) that encapsidate a linear ~4.7 kb single stranded DNA of plus or minus polarity (7, 43). The genome of AAVs is flanked by inverted terminal repeats (ITRs), which in the case of AAV2 are 145 nucleotides. The ITR is organized as three interrupted palindromes that can fold in an energetically favored T-shaped hairpin structure, which can exist in two orientations, termed flip and flop (42). The ITRs serve as origin of replication and contain cis acting elements required for rescue, integration, excision from cloning vectors and packaging (41, 42, 49 and 58).

The genetic map of the AAVs has been derived primarily from studies of AAV2 but is conserved in all serotypes (26, 27, 29, 36, 42, 45, 46, 58, 60, and 64). Two major open reading frames (rep and cap ORFs) and three transcriptional active promoters ($P_5$, $P_{19}$, $P_{40}$) have been identified in the genome of AAV2. The $P_5$ and $P_{19}$ promoters encode for the nonstructural replication proteins Rep78 and Rep 68 and Rep 52 and Rep 40, respectively. Due to differential splicing, Rep78 and Rep52 have different C termini from Rep68 and Rep40. Transcription initiation from two promoters results in Rep78 and Rep68 having different N termini from Rep52 and Rep 40. The $P_{40}$ promoter transcribes two alternatively spliced mRNAs. The major mRNA species encodes for the major capsid protein VP3 from a conventional AUG codon and the minor capsid protein VP2 from an upstream in frame ACG codon. The minor mRNA species encodes the entire cap ORF to produce the minor capsid protein VP1 (47). VP1, VP2 and VP3 are found in a ratio of 1:1:10, respectively, and this stoichiometry is generated by the high abundance of one of the mRNA species and the low translation efficiency from an ACG codon in the case of VP2 (14, 47, 55). Previous studies have indicated that VP2 and VP3 are sufficient for particle formation and accumulation of encapsidated ssDNA progeny, while VP1 is required for assembly of highly infectious particles (63, 64).

All four Rep proteins possess NTP binding activity, DNA helicase activity and nuclear localization sequences, however only Rep78/68 possess DNA binding ability (33, 34, 66). Mutant AAV defective for the synthesis of the small Rep proteins (Rep52/40) are able to replicate DNA but no ssDNA progeny is encapsidated (16). The ability of Rep78/68 to bind and nick DNA in a sequence and strand specific manner inside the ITR is essential in every phase of the AAV life cycle, namely DNA replication, AAV gene expression, rescue from the integrated state and self-excision from cloning vectors (29, 35, 44). Nicking of the DNA within the ITR at the terminal resolution site (trs) requires binding of Rep78/68 proteins to a motif composed of tandem repeats of GAGY.

Among AAV serotypes, AAV1, 4, 7 and 8 are believed to be of simian origin while AAV2, 3 and 5 are from humans. AAV6 was found in a human adenovirus preparation and is very similar to AAV1. AAVs have also been reported in other mammalian species including canines, bovine, ovine and equine (8). An avian AAV was first isolated from the Olson strain of quail bronchitis adenovirus (68). It was later found that 50% of adenoviral field isolates from chickens in US and Ireland contained AAAVs serologically indistinguishable from the initial isolate (24). The AAAV was found to be 20 nm in diameter, serologically distinct from $AAV_{1-4}$, did not agglutinate erythrocytes from several species tested and required adenovirus or herpes virus for replication (5, 68). In addition, AAAV was found to inhibit replication of several avian adenovirus and herpes virus (5, 52, 53). Physicochemical studies revealed that the capsid of AAAV consists of three VP proteins similar to other AAVs. The buoyant density of AAAV in CsCl gradients (1.39-1.44 $g/cm^3$) is similar to what have been reported for all AAVs (6, 30, 68).

The ability of AAV vectors to infect dividing and non-dividing cells and establish long-term transgene expression and the lack of pathogenicity has made them attractive for use in gene therapy applications. Recent evidence has indicated lack of cross competition in binding experiments suggesting that each AAV serotype may have a distinct mechanism of cell entry. Comparison of the cap ORFs from different serotypes has identified blocks of conserved and divergent sequence, with most of the later residing on the exterior of the virion, thus explaining the altered tissue tropism among serotypes (19-21, 48, 56). Vectors based on new AAV serotypes may have different host range and different immunological properties, thus allowing for most efficient transduction in certain cell types. In addition, characterization of new serotypes will aid in identifying viral elements required for altered tissue tropism.

Serological studies have provided evidence of avian adeno-associated virus infection in humans (69). Six percent of an unselected adult population was found positive for antibody to AAAV by agar gel precipitation (AGP), and 15.6% was positive by virus neutralization (VN). Fourteen percent of poultry workers (industry or research) were positive for AAAV antibody by AGP and 66% were positive by VN. In the same studies, no cross reaction was noted by AGP when antiserum to AAAV was reacted against primate antigens of serotypes 1-4 or when antiserum to AAV serotypes 1-4 were reacted against AAAV antigen. In addition, antiserum prepared against primate AAV1-4 did not neutralize the avian AAV. These results show that AAAV is a distinct serotype and infections are not restricted to avian species but are found in the human adult population.

Based on the genome organization and sequence homology among insect densovirus, rodent parvovirus and human dependovirus, it has been previously proposed these virus may have diverged from a common ancestor and evolved strictly in their hosts (3). However, the high sequence homology between avian autonomous parvovirus and primate AAVs and the epidemiological documentation of AAAV transmission to humans provide evidence for host-independent evolution of at least some parvovirus genera. To better understand the relationship between the avian and the primate AAVs, the complete viral genome of AAAV was cloned and sequenced and used to generate recombinant viral particles.

The present invention provides the first complete genomic AAAV sequence. The genome of AAAV is 4,694 nucleotides in length and has similar organization with that of other AAVs. The entire genome of AAAV displays 56-65% identity at the nucleotide level with the other known AAVs. The AAAV genome has inverted terminal repeats of 142 nucleotides with the first 122 forming the characteristic T-shaped palindromic structure. The putative Rep-binding element (RBE) consists of a tandem $(GAGY)_4$ repeat, and the putative terminal resolution site (trs), CCGGT/CG, contains a single nucleotide substitution relative to the $AAV_2$ trs. Surprisingly and in contrast to AAV5, the AAAV ITR can be used as an origin or replication by either AAV5 or AAV2 Rep proteins for packaging. Thus the AAAV ITR can act as a universal ITR. The Rep ORF of AAAV displays 50-54% identity at the amino acid level with the other AAVs, with most of the diversity clustered at the carboxyl and amino termini. Comparison of the capsid proteins of AAAV and the primate dependoviruses indicate divergent regions are localized to surface exposed loops. Despite these sequence differences, recombinant AAAV particles were produced carrying a lacZ reporter gene by co-transfection in 293T cells and transduction efficiency was examined in both chicken primary cells and several cell lines. This unique tropism allows AAAV to be useful as a vector for the development of transgenic animals and also allows for the vaccination of eggs as well as the preparation of recombinant proteins in avian cultures. The exposed regions of AAAV are also sites for insertions of epitopes for the purpose of changing the tropism of the virus or antigen presentation. The present invention shows that AAAV is the most divergent adeno-associated virus described to date, but maintains all the characteristics unique to the genera of dependovirus.

The present invention provides a vector comprising the AAAV virus or a vector comprising subparts of the virus, as well as AAAV viral particles. While AAAV is similar to primate AAVs, the viruses are found herein to be physically and genetically distinct. These differences endow AAAV with some unique properties and advantages which better suit it as a vector for gene therapy or gene transfer applications. As shown herein, AAAV capsid protein, again surprisingly, is distinct from primate capsid protein and exhibits different tissue tropism, thus making AAAV capsid-containing particles suitable for transducing cell types for which primate AAVs are unsuited or less well-suited. AAAV is serologically distinct and thus, in a gene therapy application, AAAV would allow for transduction of a patient who already possesses neutralizing antibodies to primate isolates either as a result of natural immunological defense or from prior exposure to other vectors. AAAV is also useful for gene transfer to other species for the development of transgenic animals or the production of vaccines and recombinant proteins in eggs. Thus, the present invention, by providing these new recombinant vectors and particles based on AAAV, provides a new and highly useful series of vectors.

SUMMARY OF THE INVENTION

The present invention provides a nucleic acid vector comprising a pair of avian adeno-associated virus (AAAV) inverted terminal repeats and a promoter between the inverted terminal repeats.

The present invention further provides an AAAV particle containing a vector comprising a pair of AAAV inverted terminal repeats.

The present invention further provides an AAAV particle containing a vector comprising a pair of AAV2 inverted terminal repeats.

The present invention further provides an AAAV particle containing a vector comprising a pair of AAV5 inverted terminal repeats.

The present invention further provides an AAV1 particle containing a vector comprising a pair of AAAV inverted terminal repeats.

The present invention further provides an AAV2 particle containing a vector comprising a pair of AAAV inverted terminal repeats.

The present invention further provides an AAV3 particle containing a vector comprising a pair of AAAV inverted terminal repeats.

The present invention further provides an AAV4 particle containing a vector comprising a pair of AAAV inverted terminal repeats.

The present invention further provides an AAV5 particle containing a vector comprising a pair of AAAV inverted terminal repeats.

The present invention further provides an AAV6 particle containing a vector comprising a pair of AAAV inverted terminal repeats The present invention further provides an AAV7 particle containing a vector comprising a pair of AAAV inverted terminal repeats The present invention further provides an AAV8 particle containing a vector comprising a pair of AAAV inverted terminal repeats The present invention further provides a dependovirus particle containing a vector comprising a pair of AAAV inverted terminal repeats.

Additionally, the instant invention provides an isolated nucleic acid comprising the nucleotide sequence set forth in SEQ ID NO:1 (AAAV genome). Furthermore, the present invention provides an isolated nucleic acid consisting essentially of the nucleotide sequence set forth in SEQ ID NO:1 (AAAV genome).

The present invention provides an isolated nucleic acid encoding an AAAV Rep protein, for example, the nucleic acid as set forth in SEQ ID NO:2. Additionally provided is an isolated full-length AAAV Rep protein or a unique fragment thereof. Additionally provided is an isolated AAAV Rep 42 protein having the amino acid sequence set forth in SEQ ID NO:9, or a unique fragment thereof. Additionally provided is an isolated AAAV Rep 52 protein having the amino acid sequence set forth in SEQ D NO:5, or a unique fragment thereof. Additionally provided is an isolated AAAV Rep 68 protein, having the amino acid sequence set forth in SEQ ID NO:7 or a unique fragment thereof. Additionally provided is an isolated AAAV Rep 78 protein having the amino acid sequence set forth in SEQ ID NO:3, or a unique fragment thereof. The sequences for these proteins are provided below in the Sequence Listing and elsewhere in the application where the proteins are described.

The present invention further provides an isolated AAAV capsid protein, VP1, having the amino acid sequence set forth in SEQ ID NO:11, or a unique fragment thereof. Additionally provided is an isolated AAAV capsid protein, VP2, having the amino acid sequence set forth in SEQ ID NO:13, or a unique fragment thereof. Also provided is an isolated AAAV capsid protein, VP3, having the amino acid sequence set forth in SEQ ID NO:15, or a unique fragment thereof.

The present invention additionally provides an isolated nucleic acid encoding AAAV capsid protein, for example, the nucleic acid set forth in SEQ ID NO:10, or a unique fragment thereof.

The present invention further provides an AAAV particle comprising a capsid protein consisting essentially of the amino acid sequence set forth in SEQ ID NO:11, or a unique fragment thereof.

Additionally, provided by the present invention is an isolated nucleic acid comprising an AAAV p5 promoter having the nucleic acid sequence set forth in SEQ ID NO:22, or a unique fragment thereof.

The instant invention provides a method of screening a cell for infectivity by AAAV comprising contacting the cell with AAAV and detecting the presence of AAAV in the cells.

The present invention further provides a method of delivering a nucleic acid to a cell comprising administering to the cell an AAAV particle containing a vector comprising the nucleic acid inserted between a pair of AAV inverted terminal repeats, thereby delivering the nucleic acid to the cell.

The present invention also provides a method of delivering a nucleic acid to a subject comprising administering to a cell from the subject an AAAV particle comprising the nucleic acid inserted between a pair of AAV inverted terminal repeats, and returning the cell to the subject, thereby delivering the nucleic acid to the subject.

The present invention also provides a method of delivering a nucleic acid to a cell in a subject comprising administering to the subject an AAAV particle comprising the nucleic acid inserted between a pair of AAV inverted terminal repeats, thereby delivering the nucleic acid to a cell in the subject.

The instant invention further provides a method of delivering a nucleic acid to a cell in a subject having antibodies to other serotypes of AAV comprising administering to the subject an AAAV particle comprising the nucleic acid, thereby delivering the nucleic acid to a cell in the subject.

The present invention also provides a method of delivering a nucleic acid to a subject comprising administering to a cell from the subject an AAAV particle comprising the nucleic acid inserted between a pair of AAAV inverted terminal repeats, and returning the cell to the subject, thereby delivering the nucleic acid to the subject.

The present invention also provides a method of delivering a nucleic acid to a cell in a subject comprising administering to the subject an AAAV particle comprising the nucleic acid inserted between a pair of AAAV inverted terminal repeats, thereby delivering the nucleic acid to a cell in the subject.

The instant invention further provides a method of delivering a nucleic acid to a cell in a subject having antibodies to primate AAVs comprising administering to the subject an AAAV particle comprising the nucleic acid, thereby delivering the nucleic acid to a cell in the subject.

BRIEF DESCRIPTION OF THE DRAWINGS

FIGS. 4A and 4B illustrate comparisons of rep and cap ORFs. The rep and cap ORFs of AAAV, AAV2, AAV4, AAV5 and Goose autonomous parvovirus (GP) were aligned using Clustal W. Identical amino acids are indicated by a dot. Dashes indicate gaps in the sequence added by the alignment program. A) Shown are rep ORFs for AAAV (SEQ ID NO:3), AAV2 (SEQ ID NO:29), AAV4 (SEQ ID NO:31), AAV5 (SEQ ID NO:33), and GP (SEQ ID NO:35). Horizontal arrows indicate the initiator codon of the p5 and p19 Rep proteins. The Rep endonuclease site established by Tyr155 and the tetrahedrally coordinated Asp24, Glu83, His90 and His92 are presented in bold letters and are over lined by an asterisk. The region important for Rep multimerization, the ATP binding site and the basic amino acids of the nuclear localization signal are underlined. The zinc finger motifs in the carboxy terminus are underlined and the coordinating cystine and histidine residues are indicated by dots. B) Shown are cap ORFs for AAAV (SEQ ID NO:11), AAV2 (SEQ ID NO:30), AAV4 (SEQ ID NO:32), AAV5 (SEQ ID NO:34), and GP (SEQ ID NO:36). The theoretical initiator codons of VP2 and VP3 are indicated in bold letters. Regions that have been proposed to be on the surface of AAV2 are underlined and divergent regions are boxed. The heparin binding region in the capsid of AAV2 is also indicated.

DETAILED DESCRIPTION OF THE INVENTION

Figure 1A:
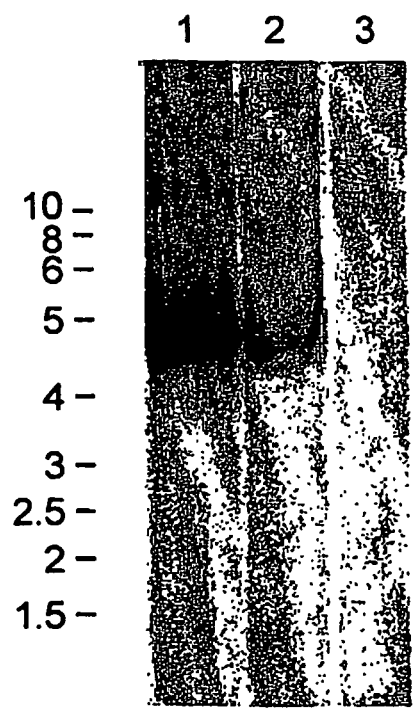
FIG. 1 shows a Southern blot analysis of AAAV nuclease resistant particles in 293T and LMH cells. A) 293T cells were transfected with pAAAV alone (lane 3), pAAAV plus pAd12 (lane 2) and pAAAV plus infection with wt Ad (lane 1). B) LMH cells were transfected with pAAAV alone (lane 2) or pAAAV plus infection with FAV1 (lane 1). Viral DNA was isolated as described in Materials and Methods and fractionated on agarose gel before southern blot analysis with a 32P-labeled pAAAV DNA.
Figure 1B:
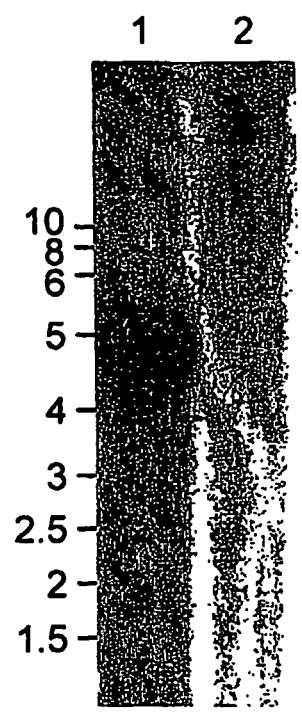
Figure 2:
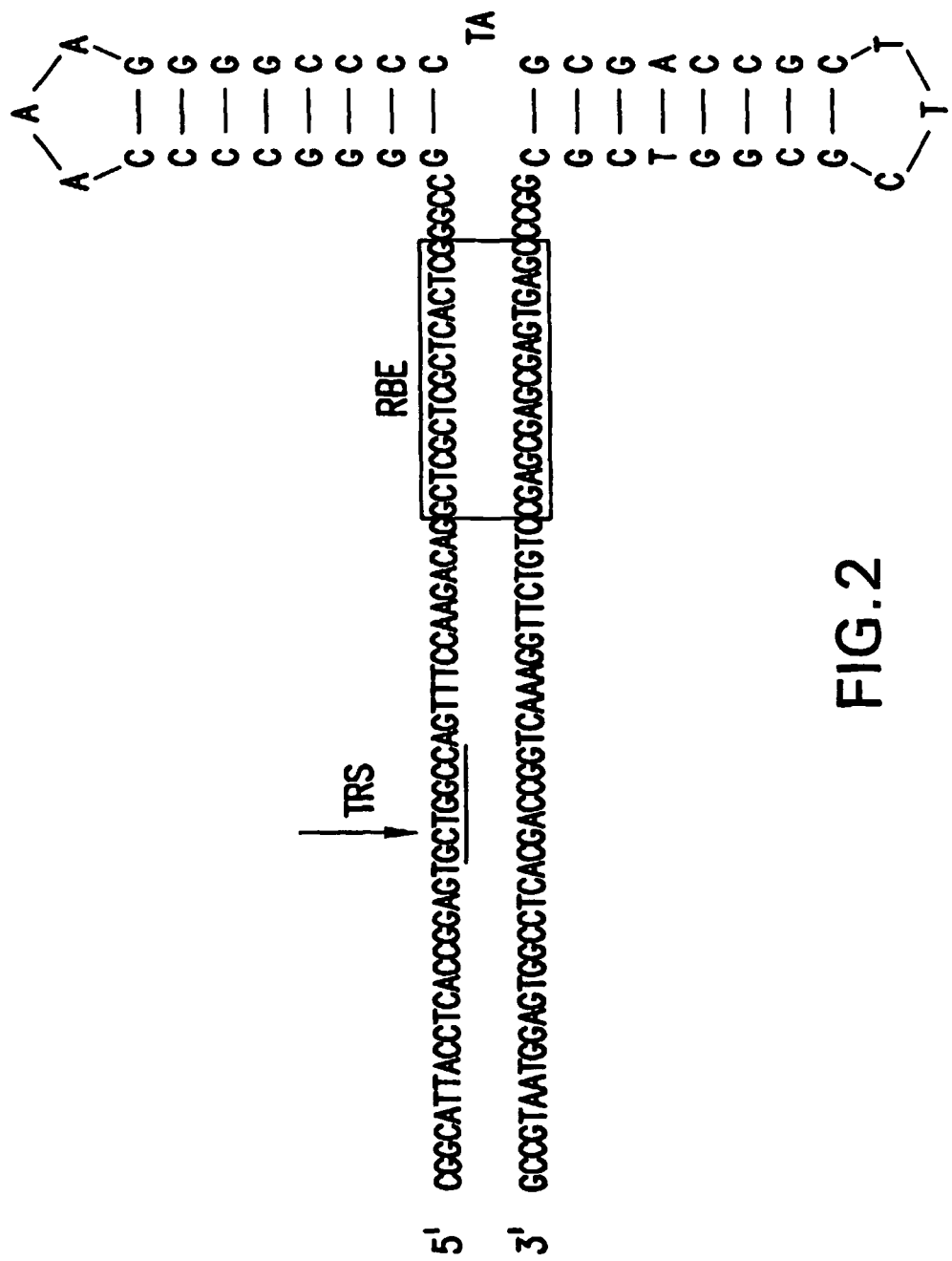
FIG. 2 shows the AAAV ITR. The sequence of the ITR (SEQ ID NO:25) is shown in the hairpin conformation. The putative Rep binding site is boxed, while the putative trs is underlined and the cleavage site is indicated by an arrow.

As used in the specification and in the claims, "a" can mean one or more, depending upon the context in which it is used. The terms "having" and "comprising" are used interchangeably herein, and signify open ended meaning.

The present application provides a recombinant avian adeno-associated virus (AAAV). This virus has one or more of the characteristics described below. The compositions of the present invention do not include wild-type AAAV. The methods of the present invention can use either wild-type AAAV or recombinant AAAV-based delivery.

The present invention provides novel AAAV particles, recombinant AAAV vectors, recombinant AAAV virions and novel AAAV nucleic acids and polypeptides. An AAAV particle is a viral particle comprising an AAAV capsid protein. A recombinant AAAV vector is a nucleic acid construct that comprises at least one unique nucleic acid of AAAV. A recombinant AAAV virion is a particle containing a recombinant AAAV vector, wherein the particle can be either an AAAV particle as described herein or a non-AAAV particle. Alternatively, the recombinant AAAV virion is an AAAV particle containing a recombinant vector, wherein the vector can be either an AAAV vector as described herein or a non-AAAV vector. These vectors, particles, virions, nucleic acids and polypeptides are described below.

The present invention provides the nucleotide sequence of the AAAV genome and vectors and particles derived therefrom. Specifically, the present invention provides a nucleic acid vector comprising a pair of AAAV inverted terminal repeats (ITRs) and a promoter between the inverted terminal repeats. The rep proteins of AAV2 and AAV5 or AAAV will bind to the AAAV ITR and the AAAV IRF can function as a universal origin or replication for packaging of recombinant AAV particles. The minimum sequence necessary for this activity is the TRS site (SEQ ID NO: 20) where Rep cleaves in order to replicate the virus. Minor modifications in an ITR are contemplated and are those that will not interfere with the hairpin structure formed by the ITR as described herein and known in the art. Furthermore, to be considered within the term e.g. it must retain the Rep binding site described herein. One of skill in the art would know how to modify an AAAV ITR such that the hairpin structure is maintained and the Rep binding site is present. One of skill in the art could contemplate any ITR that contains a Rep binding site (SEQ ID NO: 21) and a trs site (SEQ ID NO: 20). Such an ITR could be utilized in any of the vectors described herein.

The D region of the AAAV ITR, a single stranded region of the ITR, inboard of the TRS site, has been shown to bind a factor which depending on its phosphorylation state correlates with the conversion of the AAV from a single stranded genome to a transcriptionally active form that allows for expression of the viral DNA. This region is conserved between AAV2, 3, 4, and 6 but is divergent in AAV5 and AAAV. The D+ region (SEQ ID NO: 18) is the reverse complement of the D-region (SEQ ID NO: 19).

The promoter can be any desired promoter, selected by known considerations, such as the level of expression of a nucleic acid functionally linked to the promoter and the cell type in which the vector is to be used. That is, the promoter can be tissue/cell-specific. Promoters can be prokaryotic, eukaryotic, fungal, nuclear, mitochondrial, viral or plant promoters. Promoters can be exogenous or endogenous to the cell type being transduced by the vector. Promoters can include, for example, bacterial promoters, known strong promoters such as SV40 or the inducible metallothionein promoter, or an AAV promoter, such as an AAV p5 promoter. Additionally, chimeric regulatory promoters for targeted gene expression can be utilized. Examples of these regulatory systems, which are known in the art, include the tetracycline based regulatory system which utilizes the tet transactivator protein (tTA), a chimeric protein containing the VP16 activation domain fused to the tet repressor of *Escherichia coli*, the IPTG based regulatory system, the CID based regulatory system, and the Ecdysone based regulatory system (44). Other promoters include promoters derived from actin genes, immunoglobulin genes, cytomegalovirus (CMV), adenovirus, bovine papilloma virus, adenoviral promoters, such as the adenoviral major late promoter, an inducible heat shock promoter, respiratory syncytial virus, Rous sarcomas virus (RSV), etc.

Specifically, the promoter can be an AAV2 p5 promoter or an AAV5 p5 promoter or an AAAV p5 promoter. More specifically, the AAAV p5 promoter can be at about the same location in SEQ ID NO: 1 as the AAV2 p5 promoter, in the corresponding AAV2 published sequence. Additionally, the p5 promoter may be enhanced by nucleotides 1-142 of SEQ ID NO:1. Furthermore, smaller fragments of the p5 promoter that retain promoter activity can readily be determined by standard procedures including, for example, constructing a series of deletions in the p5 promoter, linking the deletion to a reporter gene, and determining whether the reporter gene is expressed, i.e., transcribed and/or translated. The promoter can be the promoter of any of the AAV serotypes, and can be the p19 promoter (SEQ ID NO: 23) or the p40 promoter set forth in the sequence listing as SEQ ID NO: 24.

It should be recognized that any errors in any of the nucleotide sequences disclosed herein can be corrected, for example, by using the hybridization procedure described below with various probes derived from the described sequences such that the coding sequence can be reisolated and resequenced. Rapid screening for point mutations can also be achieved with the use of polymerase chain reaction-single strand conformation polymorphism (PCR-SSCP) (43). The corresponding amino acid sequence can then be corrected accordingly.

The AAAV-derived vector of the invention can further comprise a heterologous nucleic acid functionally linked to the promoter. By "heterologous nucleic acid" is meant that any heterologous or exogenous nucleic acid, i.e. not normally found in wild-type AAAV can be inserted into the vector for transfer into a cell, tissue or organism. By "functionally linked" is meant that the promoter can promote expression of the heterologous nucleic acid, as is known in the art, and can include the appropriate orientation of the promoter relative to the heterologous nucleic acid. Furthermore, the heterologous nucleic acid preferably has all appropriate sequences for expression of the nucleic acid. The nucleic acid can include, for example, expression control sequences, such as an enhancer, and necessary information processing sites, such as ribosome binding sites, RNA splice sites, polyadenylation sites, and transcriptional terminator sequences.

The heterologous nucleic acid can encode beneficial proteins or polypeptides that replace missing or defective proteins required by the cell or subject into which the vector is transferred or can encode a cytotoxic polypeptide that can be directed, e.g., to cancer cells or other cells whose death would be beneficial to the subject. The heterologous nucleic acid can also encode antisense RNAs that can bind to, and thereby inactivate, mRNAs made by the subject that encode harmful proteins. The heterologous nucleic acid can also encode ribozymes that can effect the sequence-specific inhibition of gene expression by the cleavage of mRNAs. In one embodiment, antisense polynucleotides can be produced from a heterologous expression cassette in an AAAV vector construct where the expression cassette contains a sequence that promotes cell-type specific expression (Wirak et al., *EMBO* 10:289 (1991)). For general methods relating to antisense polynucleotides, see *Antisense RNA and DNA*, D. A. Melton, Ed., Cold Spring Harbor Laboratory, Cold Spring Harbor, N.Y. (1988).

Examples of heterologous nucleic acids which can be administered to a cell or subject as part of the present AAAV vector can include, but are not limited to the following: nucleic acids encoding secretory and non-secretory proteins, nucleic acids encoding therapeutic agents, such as tumor necrosis factors (TNF), such as TNF-α; interferons, such as interferon-α, interferon-β, and interferon-γ; interleukins, such as IL-1, IL-1β, and ILs-2 through -14; GM-CSF; adenosine deaminase; cellular growth factors, such as lymphokines; soluble CD4; Factor VIII; Factor IX; T-cell receptors; LDL receptor; ApoE; ApoC; alpha-1 antitrypsin; ornithine transcarbamylase (OTC); cystic fibrosis transmembrane receptor (CFTR); insulin; Fc receptors for antigen binding domains of antibodies, such as immunoglobulins; anti-HIV decoy tar elements; and antisense sequences which inhibit viral replication, such as antisense sequences which inhibit replication of hepatitis B or hepatitis non-A, non-B virus. The nucleic acid is chosen considering several factors, including the cell to be transfected. Where the target cell is a blood cell, for example, particularly useful nucleic acids to use are those which allow the blood cells to exert a therapeutic effect, such as a gene encoding a clotting factor for use in treatment of hemophilia. Another target cell is the lung airway cell, which can be used to administer nucleic acids, such as those coding for the cystic fibrosis transmembrane receptor, which could provide a gene therapeutic treatment for cystic fibrosis. Other target cells include muscle cells where useful nucleic acids, such as those encoding cytokines and growth factors, can be transduced and the protein the nucleic acid encodes can be expressed and secreted to exert its effects on other cells, tissues and organs, such as the liver. Furthermore, the nucleic acid can encode more than one gene product, limited only, if the nucleic acid is to be packaged in a capsid, by the size of nucleic acid that can be packaged.

Furthermore, suitable nucleic acids can include those that, when transferred into a primary cell, such as a blood cell, cause the transferred cell to target a site in the body where that cell's presence would be beneficial. For example, blood cells such as TIL cells can be modified, such as by transfer into the cell of a Fab portion of a monoclonal antibody, to recognize a selected antigen. Another example would be to introduce a nucleic acid that would target a therapeutic blood cell to tumor cells. Nucleic acids useful in treating cancer cells include those encoding chemotactic factors which cause an inflammatory response at a specific site, thereby having a therapeutic effect.

Cells, particularly blood cells, muscle cells, airway epithelial cells, brain cells and endothelial cells having such nucleic acids transferred into them can be useful in a variety of diseases, syndromes and conditions. For example, suitable nucleic acids include nucleic acids encoding soluble CD4, used in the treatment of AIDS and α-antitrypsin, used in the treatment of emphysema caused by α-antitrypsin deficiency. Other diseases, syndromes and conditions in which such cells can be useful include, for example, adenosine deaminase deficiency, sickle cell deficiency, brain disorders such as Alzheimer's disease, thalassemia, hemophilia, diabetes, phenylketonuria, growth disorders and heart diseases, such as those caused by alterations in cholesterol metabolism, and defects of the immune system.

As another example, hepatocytes can be transfected with the present vectors having useful nucleic acids to treat liver disease. For example, a nucleic acid encoding OTC can be used to transfect hepatocytes (ex vivo and returned to the liver or in vivo) to treat congenital hyperammonemia, caused by an inherited deficiency in OTC. Another example is to use a nucleic acid encoding LDL to target hepatocytes ex vivo or in vivo to treat inherited LDL receptor deficiency. Such transfected hepatocytes can also be used to treat acquired infectious diseases, such as diseases resulting from a viral infection. For example, transduced hepatocyte precursors can be used to treat viral hepatitis, such as hepatitis B and non-A, non-B hepatitis, for example by transducing the hepatocyte precursor with a nucleic acid encoding an antisense RNA that inhibits viral replication. Another example includes transferring a vector of the present invention having a nucleic acid encoding a protein, such as α-interferon, which can confer resistance to the hepatitis virus.

For a procedure using transfected hepatocytes or hepatocyte precursors, hepatocyte precursors having a vector of the present invention transferred in can be grown in tissue culture, removed from the tissue culture vessel, and introduced to the body, such as by a surgical method. In this example, the tissue would be placed directly into the liver, or into the body cavity in proximity to the liver, as in a transplant or graft. Alternatively, the cells can simply be directly injected into the liver, into the portal circulatory system, or into the spleen, from which the cells can be transported to the liver via the circulatory system. Furthermore, the cells can be attached to a support, such as microcarrier beads, which can then be introduced, such as by injection, into the peritoneal cavity. Once the cells are in the liver, by whatever means, the cells can then express the nucleic acid and/or differentiate into mature hepatocytes which can express the nucleic acid.

The AAAV-derived vector can include any normally occurring AAAV sequences in addition to an ITR and promoter. Examples of vector constructs are provided below.

The present vector or AAAV particle or recombinant AAAV virion can utilize any unique fragment of these present AAAV nucleic acids, including the AAAV nucleic acids set forth in SEQ ID NOS: 1, 2, 4, 6, 8, 10, 12, 14, and 16-24. To be unique, the fragment must be of sufficient size to distinguish it from other known sequences, most readily determined by comparing any nucleic acid fragment to the nucleotide sequences of nucleic acids in computer databases, such as GenBank. Such comparative searches are standard in the art. In particular, one of skill in the art will know how to distinguish an AAAV sequence from other AAV sequences. Therefore, the present invention provides AAAV nucleic acid sequences that are not found in other AAV sequences.

For example, one of skill in the art could perform alignments with an alignment program such as ClustalW or Blast2 where the parameters would be GAPOPEN or OPENGAP or OPEN GAP PENALTY: Penalty for the first residue in a gap (e.g., fasta defaults: −12 by with proteins, −16 for DNA). GAPEXT or EXTENDGAP or EXTEND GAP PENALTY: Penalty for additional residues in a gap (e.g. fasta defaults: −2 with proteins, −4 for DNA). Thus, if would be routine for one of skill in the art to utilize such alignment programs for identification of unique sequences as well as sequences that are 50%, 60%, 70%, 80%, 90%, 95% and 100% identical to the nucleic acid sequences described herein, as well as sequences that are 50%, 60%, 70%, 80%, 90%, 95% and 100% identical to the protein sequences described herein.

Typically, a unique fragment useful as a primer or probe will be at least about 8 or 10, preferable at least 20 or 25 nucleotides in length, depending upon the specific nucleotide content of the sequence. Additionally, fragments can be, for example, at least about 30, 40, 50, 60, 70, 80, 90, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675 or 700 nucleotides in length and can encode polypeptides or be probes. The nucleic acid can be single or double stranded, depending upon the purpose for which it is intended. Where desired, the nucleic acid can be RNA.

The present invention further provides an AAAV capsid protein to contain the vector. In particular, the present invention provides not only a polypeptide comprising all three AAAV coat proteins, i.e., VP1, VP2 and VP3, but also a polypeptide comprising each AAAV coat protein individually, SEQ ID NOS: 11, 13, and 15, respectively. Thus an AAAV particle comprising an AAAV capsid protein comprises at least one AAAV coat protein VP1, VP2 or VP3. The present invention also provides particles comprising fragments of VP1, VP2 or VP3 that allow the particle to maintain AAAV functionality and tropism. An AAAV particle comprising an AAAV capsid protein can be utilized to deliver a nucleic acid vector to a cell, tissue or subject. For example, the herein described AAAV vectors can be encapsidated in an AAV5 capsid-derived particle and utilized in a gene delivery method. Furthermore, other viral nucleic acids can be encapsidated in the AAAV particle and utilized in such delivery methods. For example, an AAV1-8 vector (e.g. a vector comprising an AAV1, AAV2, AAV3, AAV4, AAV5, AAV6, AAV7 or an AAV8 ITR and a nucleic acid of interest) can be encapsidated in an AAAV particle and administered. Furthermore, an AAAV chimeric capsid incorporating both AAV2 capsid and AAAV capsid sequences can be generated, by standard cloning methods, selecting regions from the known sequences of each protein as desired. For example, particularly antigenic regions of the AAAV capsid protein can be replaced with the corresponding region of the AAV2 capsid protein. In addition to chimeric capsids incorporating AAV2 capsid sequences, chimeric capsids incorporating AAV1, AAV3-8, and/or AAV5 capsid sequences can be generated, by standard cloning methods, selecting regions from the known sequences of each protein as desired. Alternatively a chimeric capsid can be made by the addition of a plasmid that expresses AAV1-8 capsid proteins at a ratio with the AAAV capsid expression plasmid that allows only a few capsid proteins to be incorporated into the AAAV particle. Thus, for example, a chimeric particle may be constructed that contains 6 AAV2 capsid proteins and 54 AAAV capsid proteins if the complete capsid contains 60 capsid proteins.

The AAAV capsid proteins can also be modified to alter their specific tropism by genetically modifying the capsid to comprise a specific ligand that binds to a cell surface receptor. Alternatively, the capsid can be chemically modified by conjugating a ligand to a cell surface receptor. By genetically or chemically altering the capsids, the tropism can be modified to direct AAAV to a particular cell or population of cells. The capsids can also be altered immunologically by conjugating the capsid to an antibody that recognizes a specific protein on the target cell or population of cells.

It has been recently reported that insertion of foreign epitopes (RGD motif, LH receptor targeting epitope) in certain regions of AAV2 capsid can redirect viral tropism. However, AAV2 naturally infects a wide variety of cell types and complete retargeting of rAAV2 would be difficult to achieve. For example, removal of the heparin binding activity, which is a major determinant of aav2 transduction in vitro, still results in AAV2 transduction of heart tissue in vivo. rAAAV displays a more restrict tropism with preferential transduction of avian cells. Therefore AAAV could be more easily engineered to specifically target certain cell types. Based on cryo-electron microscopy imaging of AAV2, 4 and 5, molecular modeling, and sequence alignments, we have identified regions in the capsid of AAAV that are on the virus surface and could tolerate substitution. Two of these regions are aa 269-278 (PSGGDNNNKF; SEQ ID NO:37), and for some uses, more preferably aa 267-274 (QGPSGGD; SEQ ID NO:38). There is evidence that the variable loop comprises QGPSGGD (SEQ ID NO:38) and that NNNKF (SEQ ID NO:39) may be conserved and may be important in structure. A substitution into PSGGDNNNKF (SEQ ID NO:37) it did not assemble well and was not infectious in any cell. However, this type of insertion is useful for antigen presentation but not retargeting of the vector. Antigens presented in order arrays on the surface of viruses tend to be more antigenic than if they are presented in random. Another region is aa 454-463 (VSQAGSSGRA; SEQ ID NO:40).

For insertion between aa 146-147

```
AAAV 146-LH nc:
CGTCTTTGAGTCTTCCACCAGACCAAAG (SEQ ID NO: 41)

AAAV 146-LH c:
CACTGCAGCACCTGCTACTACCACAAGAGCGCTCCGACCGGAGACAAGCG
(SEQ ID NO: 42)
```

For substitution at aa 267-274,

```
LHR-267-274F
5'CAACCACCTGTACAAACGAATCCACTGCAGCACCTGCTACTACCACAA
GAGCAACAACAACAAATTCTTTGGATTC-3' (SEQ ID NO: 43)

LHR-267-274R
5'GAATCCAAAGAATTTGTTGTTGTTGCTCTTGTGGTAGTAGCAGGTGCT
GCAGTGGATTCGTTTGTACAGGTGGTTG-3' (SEQ ID NO: 44)
```

For substitution at aa 269-278,

```
LHR-269-278F
CAAACGAATCCAAGGACACTGCAGCACCTGCTACTACCACAAGAGCTTTG
GATTCAGCACC (SEQ ID NO: 45)
```

-continued
```
LHR-269-278R
GGTGCTGAATCCAAAGCTCTTGTGGTAGTAGCAGGTGCTGCAGTGTCCTT
GGATTCGTTTG (SEQ ID NO: 46)
```

For substitution at aa 454-463,

```
LHR-454-463F
TACCTCTGGGCTTTCAGCTCCCACTGCAGCACCTGCTACTACCACAAGAG
CCTTCATTACTCGCGGGCGAC (SEQ ID NO: 47)

LHR-454-463R
GTCGCCCGCGAGTAATGAAGGCTCTTGTGGTAGTAGCAGGTGCTGCAGTG
GGAGCTGAAAGCCCAGAGGTA (SEQ ID NO: 48)
```

Other regions of the AAAV capsid could also accommodate the substitution of amino acids that would allow for epitope presentation on the surface of the virus. All of these regions would have the following characteristics in common: 1) surface exposure, 2) ability to support a substitution of sequence to insert the epitope, 3) allows for capsid assembly. Examples of other insertion or substitution regions on the virus surface are the regions around T385-R394, S588-R601, T589-R600, S455-R462, S455-R463, T546-Q559, R550-T556, V329-1338, G708-T720, Ser 710-Y728 of VP1.

Because of the symmetry of the AAV particles, a substitution in one subunit of the capsid will appear multiple times on the capsid surface. For example the capsid is made of approximately 55 VP3 proteins (i.e., 50 VP3 is 90% of the capsid and there are 60 faces on an icosahedron). Therefore an epitope incorporated in the VP3 protein could be expressed 55 times on the surface of each particle increasing the likelihood of the epitope forming a stable interaction with its target. An epitope inserted upstream of the VP3 ORF may be presented in both the VP2 and VP1 proteins, or up to 10 times on the surface of each particle. In some cases this ligand density may be too high for functional binding or this high a density of epitope may interfere with capsid formation. The epitope density could be lowered by introducing another plasmid into the packaging system for production of recombinant particles and the ratio between the packaging plasmid with the modified VP protein and the wild type VP protein altered to balance the epitope density on the virus surface. Thus one example would be on an epitope that is targeted for the mounds at the 3 fold axis of symmetry. By mixing in 2 wild type rep and cap expression plasmids with 1 mutant rep and cap plasmid, instead of the mutant epitope being found in all three mounds at each three fold axis (60 times), it will only be present in 1 mound (20 times).

Epitopes can be incorporated into the virus capsid for the purpose of 1) altering the tropism of the virus, 2) blocking an immune response directed at the virus, 3) developing a host immune response to the epitope for the purpose of vaccination, and 4) catalyzing a reaction.

Examples of epitopes that can be added to AAAV capsids include but are not limited to the following proteins and protein fragments:

LH receptor binding epitope: Photoaffinity labeling of the lutropin receptor with synthetic peptide for carboxyl terminus of the human choriogonadotropin alpha subunit. Kundu G C, Ji I, McCormick D J, Ji T H. J Biol Chem. 1996 May 10; 271(19): 11063-6 (incorporated herein by reference);

RGD integrin binding epitope: Cell attachment activity of fibronectin can be duplicated by small synthetic fragments of the molecule. Pierschbacher M D, Ruoslahti E. Nature. 1984 May 3-9; 309(5963):30-3 (incorporated herein by reference);

CD13 binding epitope NGRAHA (SEQ ID NO:49): Incorporation of tumor-targeting peptides into recombinant adeno-associated virus capsids. Grifman M, Trepel M, Speece P, Gilbert L B, Arap W, Pasqualini R, Weitzman M D. Mol Ther. 2001 June; 3(6):964-75 (incorporated herein by reference) and F. Curnis, A. Sacchi, L. Borgna, F. Magni, A. Gasparri and A. Corti, Enhancement of tumor necrosis factor alpha antitumor immunotherapeutic properties by targeted delivery to aminopeptidase N (CD13). Nat. Biotechnol. 18 (2000), pp. 1185*1190 (incorporated herein by reference);

Single chain antibody fragments: Q. Yang, Development of novel cell surface CD34-targeted recombinant adenoassociated virus vectors for gene therapy. Hum. Gene Ther. 9 (1998), pp. 1929*1937 (incorporated herein by reference);

Endothelial cell binding epitope SIGYPLP (SEQ ID NO:50): R. Pasqualini and E. Ruoslahti, Organ targeting in vivo using phage display peptide libraries. Nature 380 (1996), pp. 364*366 (incorporated herein by reference) and D. Rajotte, W. Arap, M. Hagedorn, E. Koivunen, R. Pasqualini and E. Ruoslahti, Molecular heterogeneity of the vascular endothelium revealed by in vivo phage display. J. Clin. Invest. 102 (1998), pp. 430*437 (incorporated herein by reference);

Lung targeting peptide CGFECVRQCPERC (SEQ ID NO:51): D. Rajotte and E. Ruoslahti, Membrane dipeptidase is the receptor for a lung-targeting peptide identified by in vivo phage display. J. Biol. Chem. 274 (1999), pp. 11593*11598 (incorporated herein by reference);

Muscle targeting peptide ASSLNIA (SEQ ID NO:52): T. I. Samoylova and B. F. Smith, Elucidation of muscle-binding peptides by phage display screening. Muscle Nerve 22 (1999), pp. 460*466 (incorporated herein by reference);

Tumor endothelium targeting: W. Arap, R. Pasqualini and E. Ruoslahti, Cancer treatment by targeted drug delivery to tumor vasculature in a mouse model. Science 279 (1998), pp. 377*380 (incorporated herein by reference);

Major immunogenic epitope for parvovirus B19 NISLDNPLENPSSLFDLVARIK (SEQ ID NO:53): K. Yoshimoto, A second neutralizing epitope of B19 parvovirus implicates the spike region in the immune response. J. Virol. 65 (1991), pp. 7056*7060 (incorporated herein by reference);

Serpin receptor ligand (KFNKPFVFLI (SEQ ID NO:54)): A small, synthetic peptide for gene delivery via the serpin-enzyme complex receptor. Patel S, Zhang X, Collins L, Fabre J W. J Gene Med. 2001 May-June; 3(3):271-9 (incorporated herein by reference); Hemagglutinin (HA) 91-108: A retro-inverso peptide analogue of influenza virus hemagglutinin B-cell epitope 91-108 induces a strong mucosal and systemic immune response and confers protection in mice after intranasal immunization. Ben-Yedidia T, Beignon A S, Partidos C D, Muller S, Arnon R. Mol Immunol. 2002 October; 39(5-6): 323-31 (incorporated herein by reference); NDV epitope 447 to 455: Newcastle disease virus (NDV) marker vaccine: an immunodominant epitope on the nucleoprotein gene of NDV can be deleted or replaced by a foreign epitope. Mebatsion T, Koolen M J, de Vaan L T, de Haas N, Braber M, Romer-Oberdorfer A, van den Elzen P, van der Marel P. J. Virol. 2002 October; 76(20):10138-46 (incorporated herein by reference); RETANEF (SEQ ID NO:55) HIV-1 epitope vaccine candidate: A novel chimeric Rev, Tat, and Nef (Retanef) antigen as a component of an SIV/HIV vaccine. Hel Z, Johnson J M, Tryniszewska E, Tsai W P, Harrod R, Fullen J, Tartaglia J, Franchini G. Vaccine. 2002 Aug. 19; 20(25-26): 3171-86 (incorporated herein by reference); and Catalytic single chain antibodies: Schultz, P. G. and Lerner, R. A., From molecular diversity to catalysis: lessons from the immune system 1995. Science 269, pp. 1835*1842 (incorporated herein by reference for its teaching of catalytic single chain antibodies responsible for the cleavage of protein substrates).

The capsids can also be assembled into empty particles by expression in mammalian, bacterial, fungal or insect cells. For example, AAV2 particles are known to be made from VP3 and VP2 capsid proteins in baculovirus. The same basic protocol can produce an empty AAAV particle comprising an AAAV capsid protein and also full particles.

The herein described recombinant AAAV nucleic acid derived vector can be encapsidated in an AAV particle. In particular, it can be encapsidated in an AAV1 particle, an AAV2 particle, an AAV3 particle, an AAV4 particle, an AAV5 particle, an AAV6 particle, and AAV7 particle or an AAV8 particle. A portion of any of the capsids, or a chimeric capsid particle as described above can be utilized, by standard methods using the appropriate capsid proteins in the encapsidation process, as long as the nucleic acid vector fits within the size limitation of the particle utilized. The encapsidation process itself is standard in the art. The AAAV replication machinery, i.e. the rep initiator proteins and other functions required for replication, can be utilized to produce the AAAV genome that can be packaged in an AAV1-8 capsid.

The recombinant AAAV virion containing a vector can also be produced by recombinant methods utilizing multiple plasmids. In one example, the AAAV rep nucleic acid would be cloned into one plasmid, the AAAV ITR nucleic acid would be cloned into another plasmid and the nucleic acid encoding a capsid (for example, an AAV capsid from AAV1-AAV8) would be cloned on another plasmid. These plasmids would then be introduced into cells. The cells that were efficiently transduced by all three plasmids, would exhibit specific integration as well as the ability to produce AAAV recombinant virus. Additionally, two plasmids could be used where the AAAV rep nucleic acid would be cloned into one plasmid and the AAAV ITR and AAAV capsid would be cloned into another plasmid. These plasmids would then be introduced into cells. The cells that were efficiently transduced by both plasmids, would exhibit specific integration as well as the ability to produce AAAV recombinant virus.

The capsid proteins of the present invention can have about 70% homology, about 75% homology, 80% homology, 85% homology, 90% homology, 95% homology, 98% homology, 99% homology, or even 100% homology to the protein having the amino acid sequence encoded by the nucleotides set forth in SEQ ID NOS:10, 12 or 14. The percent homology used to identify proteins herein, can be based on a nucleotide-by-nucleotide comparison or more preferable is based on a computerized algorithm as described herein. Variations in the amino acid sequence of the AAAV capsid protein are contemplated herein, as long as the resulting particle comprising an AAAV capsid protein remains antigenically or immunologically distinct from AAV1-8 capsid, as can be routinely determined by standard methods. Specifically, for example, ELISA and Western blots can be used to determine whether a viral particle is antigenically or immunologically distinct from AAV2 or the other serotypes. Furthermore, the AAAV particle preferably retains tissue tropism distinction from AAV2, such as that exemplified in the examples herein. An AAAV chimeric particle comprising at least one AAAV coat protein may have a different tissue tropism from that of an AAAV particle consisting only of AAAV coat proteins, but is still distinct from the tropism of an AAV2 particle.

The invention further provides a recombinant AAAV virion, comprising an AAAV particle containing, i.e., encapsidating, a vector comprising a pair of AAAV inverted terminal repeats. The recombinant vector can further comprise an AAAV Rep-encoding nucleic acid. The vector encapsidated in the particle can further comprise an exogenous nucleic acid inserted between the inverted terminal repeats.

The invention further contemplates chimeric recombinant ITRs that contain a rep binding site and a TRS site recognized by that Rep protein. By "Rep protein" is meant all four of the Rep proteins, Rep 40, Rep 78, Rep 52, Rep 68. Alternatively, "Rep protein" could be one or more of the Rep proteins described herein. One example of a chimeric ITR would consist of an AAAV D region (SEQ ID NOs: 18, 19), an AAAV TRS site (SEQ ID NO: 20), an AAV2 hairpin and an AAV2 binding site. Another example would be an AAAV D region, an AAAV TRS site, an AAV3 hairpin and an AAV3 binding site. In these chimeric ITRs, the D region can be from AAV1-8. The hairpin can be derived from AAV 1-8. The binding site can be derived from any of AAV1-8. The D region and the TRS can be from the same serotype.

The chimeric ITRs can be combined with AAAV Rep protein and any of the AAV serotype capsids to obtain recombinant virion. For example, recombinant virion can be produced by an AAAV D region, an AAAV TRS site, an AAV2 hairpin, an AAV2 binding site, AAAV Rep protein and AAV1 capsid. This recombinant virion would possess the cellular tropism conferred by the AAV1 capsid protein and would possess the efficient replication conferred by the AAAV Rep.

Other examples of the ITR, Rep protein and Capsids that will produce recombinant virus are provided in the list below but not limited to:
AITR+ARep+ACap=virus
AITR+5Rep+1 Cap=virus
AITR+2Rep+2Cap=virus
AITR+7Rep+3Cap=virus
AITR+5Rep+4Cap=virus
AITR+5Rep+6Cap=virus
1ITR+1Rep+ACap=virus
2ITR+2Rep+ACap=virus
4ITR+4Rep+ACap=virus
5ITR+5Rep+ACap=virus
6ITR+6Rep+ACap=virus
(A=Avian, 1=AAV1, 2=AAV2, 3=AAV3, 4=AAV4, 5=AAV5, 6=AAV6)

In any of the constructs described herein, a promoter can be included. As used in the constructs herein, unless otherwise specified, Cap (capsid) refers to any of AAAV VP1, AAAV VP2, AAAV VP3, combinations thereof, functional fragments of any of VP1, VP2 or VP3, or chimeric capsids as described herein. The ITRs of the constructs described herein, can be chimeric recombinant ITRs as described elsewhere in the application.

Conjugates of recombinant or wild-type AAAV virions and nucleic acids or proteins can be used to deliver those molecules to a cell. For example, the purified AAAV can be used as a vehicle for delivering DNA bound to the exterior of the virus. Examples of this are to conjugate the DNA to the virion by a bridge using poly-L-lysine or another charged molecule. Also contemplated are virosomes that contain AAAV structural proteins (AAAV capsid proteins), lipids such as DOTAP, and nucleic acids that are complexed via charge interaction to introduce DNA into cells.

Also contemplated by this invention is a method of delivering a DNA vaccine to a cell, comprising: administering a liposome comprising DNA conjugated to an AAAV virion to a cell thus delivering the DNA vaccine to the cell.

High levels of humoral and cell-mediated immunity can be achieved via administration of DNA vaccines. Numerous studies have shown that immunization of experimental animals with plasmid DNA encoding antigens from a wide spectrum of bacteria, viruses, protozoa and cancers leads to protective humoral and cell-mediated immunity (Gregoriadis G. "Genetic vaccines: strategies for optimization" Pharm Res. 15:661-70 (1998)).

Liposomes have been widely used to enhance the immune response. For example, a DNA vaccine constructed with the CMV promoter conjugated to env gp160 and rev genes has been shown to induce an effective immune response when inoculated via intramuscular, intraperitoneal, subcutaneous, intradermal and intranasal routes (Fukushima I. N. "Cationic liposomes are a strong adjuvant for a DNA vaccine of human immunodeficiency virus type 1" 13:1421-1428 (1997)). By immunizing with pCMV160/REV and cationic liposomes through various routes higher levels of both antibody production and delayed-type hypersensitivity were induced than by using DNA vaccine alone.

DNA vaccines can also be administered in combination with other agents in liposomes to increase levels of immunity. Co-administration of the DNA vaccine with IL-12 and granulocyte/macrophage CSF-expressing plasmids induced high levels of HIV-specific circulating T lymphocytes and in increase in delayed type hypersensitivity when administered by the intranasal route. The results indicate that intranasal administration of this DNA vaccine with liposomes, together with IL-12 and/or granulocyte/macrophage-CSF expressing plasmids, induces a strong level of anti-HIV-1 immune response (Okada E. "Intranasal immunization of a DNA vaccine with IL-12 and granulocyte-macrophage colony-stimulating factor (GM-CSF)-expressing plasmids in liposomes induces strong mucosal and cell-mediated immune responses against HIV-1 antigens" 159:3638-47 (1997)).

The liposome comprising a recombinant AAAV virion and a biological molecule or a DNA vaccine can be delivered to a specific cell type by covalently attaching a targeting moiety to a liposome or allowing the targeting moiety to become integrated into the membrane as the liposome is formed. The targeting moiety can bind to a specific cell type, thus allowing the contents of the liposome to be delivered to a cell. For example, a targeting moiety specific for tumor cells can be incorporated into the liposome. Upon delivery of the liposome, the targeting moiety will bind to a tumor cell allowing thus allowing the toxin to enter the tumor cell. Alternatively, the targeting moiety can be a ligand that binds to a cell surface protein or receptor. Numerous cell-specific cell surface proteins are known which can be targeted by the present invention by incorporating a ligand for the cell surface protein into liposomes.

Also provided by this invention are conjugates that utilize the AAAV capsid or a unique region of the AAAV capsid protein (e.g. VP1, VP2 or VP3 or combinations thereof) to introduce DNA into cells. For example, the AAAV VP3 protein or fragment thereof, can be conjugated to a DNA on a plasmid that is conjugated to a lipid. Cells can be infected using the targeting ability of the VP3 capsid protein to achieve the desired tissue tropism, specific to AAAV. AAAV VP1 and VP2 proteins can also be utilized to introduce DNA or other molecules into cells. By further incorporating the Rep protein and the AAAV TRS into the DNA-containing conjugate, cells can be transduced and targeted integration can be achieved. For example, if AAAV specific targeted integration is desired, a conjugate composed of the AAAV VP3 capsid, AAAV rep or a fragment of AAAV rep, AAAV TRS, the rep binding site, the heterologous DNA of interest, and a lipid, can be utilized to achieve AAAV specific tropism and AAAV specific targeted integration in the genome.

Further provided by this invention are chimeric viruses where AAAV can be combined with herpes virus, baculovirus or other viruses to achieve a desired tropism associated with another virus. For example, the AAAV ITRs could be inserted in the herpes virus and cells could be infected. Post-infection, the ITRs of AAAV could be acted on by AAAV rep provided in the system or in a separate vehicle to rescue AAAV from the genome. Therefore, the cellular tropism of the herpes simplex virus can be combined with AAAV rep mediated targeted integration. Other viruses that could be utilized to construct chimeric viruses include, lentivirus, retrovirus, pseudotyped retroviral vectors, and adenoviral vectors.

In another example, AAAV infects avian cells in much greater efficiencies than any other AAV. Traditionally, wild type AAAV has been propagated in chicken embryonated eggs in co-infection with avian adenoviruses (i.e., Fowl adenovirus type I, better known as CELO virus). Recently, recombinant CELO virus that can replicate in chicken embryonated eggs has been constructed (Anne-Isabelle Michou et al, 1999, J virol. 73(2): 1399). A recombinant AAAV virion that encapsidates a therapeutic gene flanked by AAAV ITRs can be produced in embryonated chicken eggs upon co-infection with a recombinant CELO virus expressing the AAAV's rep and cap gene.

Any of the particles or virions comprising an exogenous nucleic acid encoding a protein described herein can be administered to a fertilized avian egg for the purposes of producing the recombinant protein in an avian egg. This is particularly useful for the production of vaccines as the protein produced in the avian egg can be readily purified by methods known in the art and administered to subjects in need of a vaccine.

The present invention further provides isolated nucleic acids of AAAV. For example, provided is an isolated nucleic acid comprising the nucleotide sequence set forth in SEQ ID NO:1 (AAAV genome). This nucleic acid, or portions thereof, can be inserted into vectors, such as plasmids, yeast artificial chromosomes, or other viral vector (particle), if desired, by standard cloning methods. The present invention also provides an isolated nucleic acid consisting essentially of the nucleotide sequence set forth in SEQ ID NO:1. The nucleotides of SEQ ID NO:1 can have minor modifications and still be contemplated by the present invention. For example, modifications that do not alter the amino acid encoded by any given codon (such as by modification of the third, "wobble," position in a codon) can readily be made, and such alterations are known in the art. Furthermore, modifications that cause a resulting neutral (conserved) amino acid substitution of a similar amino acid can be made in a coding region of the genome. Additionally, modifications as described herein for the AAAV components, such as the ITRs, the p5 promoter, etc. are contemplated in this invention. Furthermore, modifications to regions of SEQ ID NO:1 other than in the ITR, TRS Rep binding site and hairpin are likely to be tolerated without serious impact on the function of the nucleic acid as a recombinant vector.

As used herein, the term "isolated" refers to a nucleic acid separated or significantly free from at least some of the other components of the naturally occurring organism, for example, the cell structural components or viral components commonly found associated with nucleic acids in the environment of the virus and/or other nucleic acids. The isolation of the native nucleic acids can be accomplished, for example, by techniques such as cell lysis followed by phenol plus chloroform extraction, followed by ethanol precipitation of the nucleic acids. The nucleic acids of this invention can be isolated from cells according to any of many methods well known in the art.

As used herein, the term "nucleic acid" refers to single- or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the novel genes discussed herein or may include alternative codons which encode the same amino acid as those provided herein, including that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides).

The present invention additionally provides an isolated nucleic acid that selectively hybridizes with any nucleic acid disclosed herein, including the entire AAAV genome and any unique fragment thereof, including the Rep and capsid encoding sequences (e.g. SEQ ID NOS: 1, 2, 4, 6, 8, 10, 12, 14 and 16-24). Specifically, the nucleic acid can selectively or specifically hybridize to an isolated nucleic acid consisting of the nucleotide sequence set forth in SEQ ID NO:1 (AAAV genome). The present invention further provides an isolated nucleic acid that selectively or specifically hybridizes with an isolated nucleic acid comprising the nucleotide sequence set forth in SEQ ID NO:1 (AAAV genome). By "selectively hybridizes" as used herein is meant a nucleic acid that hybridizes to one of the disclosed nucleic acids under sufficient stringency conditions without significant hybridization to a nucleic acid encoding an unrelated protein, and particularly, without detectably hybridizing to nucleic acids of AAV2 or other AAVs. Thus, a nucleic acid that selectively hybridizes with a nucleic acid of the present invention will not selectively hybridize under stringent conditions with a nucleic acid encoding a different protein or the corresponding protein from a different serotype of the virus, and vice versa. A "specifically hybridizing" nucleic acid is one that hybridizes under stringent conditions to only a nucleic acid found in AAAV. Therefore, nucleic acids for use, for example, as primers and probes to detect or amplify the target nucleic acids are contemplated herein. Nucleic acid fragments that selectively hybridize to any given nucleic acid can be used, e.g., as primers and or probes for further hybridization or for amplification methods (e.g., polymerase chain reaction (PCR), ligase chain reaction (LCR)). Additionally, for example, a primer or probe can be designed that selectively hybridizes with both AAAV and a gene of interest carried within the AAAV vector (i.e., a chimeric nucleic acid).

Stringency of hybridization is controlled by both temperature and salt concentration of either or both of the hybridization and washing steps. Typically, the stringency of hybridization to achieve selective hybridization involves hybridization in high ionic strength solution (6×SSC or 6×SSPE) at a temperature that is about 12-25° C. below the $T_m$ (the melting temperature at which half of the molecules dissociate from their hybridization partners) followed by washing at a combination of temperature and salt concentration chosen so that the washing temperature is about 5° C. to 20° C. below the $T_m$. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The washing temperatures can be used as described above to achieve selective stringency, as is known in the art. (Sambrook et al., *Molecular Cloning: A Laboratory Manual,* 2nd Ed., Cold Spring Harbor Laboratory, Cold Spring Harbor, N.Y., 1989; Kunkel et al. *Methods Enzymol.* 1987:154:367, 1987). For the nucleic acids of the present invention, stringent hybridization conditions for a DNA:DNA hybridization can be at about 65° C. (in aqueous solution) in 6×SSC or 6×SSPE followed by washing at 65° C. Therefore, the present invention provides nucleic acids that selectively hybridize to any of the nucleic acids described herein at about 65° C. (in aqueous solution) in 6×SSC or 6×SSPE followed by washing at 65° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

A nucleic acid that selectively hybridizes to any portion of the AAAV genome is contemplated herein. Therefore, a nucleic acid that selectively hybridizes to AAAV can be of longer length than the AAAV genome, it can be about the same length as the AAAV genome or it can be shorter than the AAAV genome. The length of the nucleic acid is limited on the shorter end of the size range only by its specificity for hybridization to AAAV, i.e., once it is too short, typically less than about 5 to 7 nucleotides in length, it will no longer bind specifically to AAAV, but rather will hybridize to numerous background nucleic acids. Additionally contemplated by this invention is a nucleic acid that has a portion that specifically hybridizes to AAAV and a portion that specifically hybridizes to a gene of interest inserted within AAAV.

The present invention further provides an isolated nucleic acid encoding an avian adeno-associated virus Rep protein. The AAAV Rep proteins are encoded by open reading frame (ORF) 1 of the AAAV genome. Examples of the AAAV Rep genes are shown in the nucleic acid set forth in SEQ ID NO:1, and include nucleic acids consisting essentially of the nucleotide sequences set forth in SEQ ID NOS:4 (Rep52), 2 (Rep78), 8 (Rep40), and 6 (Rep68), and nucleic acids comprising the nucleotide sequences set forth in SEQ ID NOS:2, 4, 6 and 8. Also contemplated herein are vectors comprising nucleotides 1-600 of SEQ ID NO: 1 which encode the first 200 amino acids of Rep. However, the present invention contemplates that the Rep nucleic acid can include any one, two, three, or four of the four Rep proteins, in any order, in such a nucleic acid. Furthermore, minor modifications are contemplated in the nucleic acid, such as silent mutations in the coding sequences, mutations that make neutral or conservative changes in the encoded amino acid sequence, and mutations in regulatory regions that do not disrupt the expression of the gene. Examples of other minor modifications are known in the art. Further modifications can be made in the nucleic acid, such as to disrupt or alter expression of one or more of the Rep proteins in order to, for example, determine the effect of such a disruption; such as to mutate one or more of the Rep proteins to determine the resulting effect, etc. However, in general, a modified nucleic acid encoding a Rep protein will have at least about 70%, about 75%, about 80%, about 85%, about 90%, about 93%, about 95%, about 98% or 100% homology to the Rep nucleic sequences described herein e.g., SEQ ID NOS: 2, 4, 6 and 8, and the Rep polypeptide encoded therein will have overall about 70%, about 75%, about 80%, about 85%, about 90%, about 95%, about 98%, about 99% or 100% homology with the amino acid sequence described herein, e.g., SEQ ID NOS:3, 5, 7 and 9. Percent homology is determined by the techniques described herein.

The present invention also provides an isolated nucleic acid that selectively or specifically hybridizes with a nucleic acid consisting essentially of the nucleotide sequence set forth in SEQ ID NOS: 2, 4, 6 and 8 and an isolated nucleic acid that selectively hybridizes with a nucleic acid comprising the nucleotide sequence set forth in SEQ ID NOS: 2, 4, 6 and 8. "Selectively hybridizing" and "stringency of hybridization" is defined elsewhere herein.

As described above, the present invention provides the nucleic acid encoding a Rep 40 protein and, in particular an isolated nucleic acid comprising the nucleotide sequence set forth in SEQ ID NO: 8, an isolated nucleic acid consisting essentially of the nucleotide sequence set forth in SEQ ID NO: 8, and a nucleic acid encoding the avian adeno-associated virus protein having the amino acid sequence set forth in SEQ ID NO: 9. The present invention also provides the nucleic acid encoding a Rep 52 protein, and in particular an isolated nucleic acid comprising the nucleotide sequence set forth in SEQ ID NO:4, an isolated nucleic acid consisting essentially of the nucleotide sequence set forth in SEQ ID NO:4, and a nucleic acid encoding the avian adeno-associated virus Rep protein having the amino acid sequence set forth in SEQ ID NO:5. The present invention further provides the nucleic acid encoding a Rep 68 protein and, in particular an isolated nucleic acid comprising the nucleotide sequence set forth in SEQ ID NO: 6, an isolated nucleic acid consisting essentially of the nucleotide sequence set forth in SEQ ID NO: 6, and a nucleic acid encoding the avian adeno-associated virus protein having the amino acid sequence set forth in SEQ ID NO: 7. And, further, the present invention provides the nucleic acid encoding a Rep 78 protein, and in particular an isolated nucleic acid comprising the nucleotide sequence set forth in SEQ ID NO:2, an isolated nucleic acid consisting essentially of the nucleotide sequence set forth in SEQ ID NO:, and a nucleic acid encoding the avian adeno-associated virus Rep protein having the amino acid sequence set forth in SEQ ID NO:3. As described elsewhere herein, these nucleic acids can have minor modifications, including silent nucleotide substitutions, mutations causing conservative amino acid substitutions in the encoded proteins, and mutations in control regions that do not or minimally affect the encoded amino acid sequence.

The present invention further provides a nucleic acid encoding the entire AAAV Capsid polypeptide. Furthermore, the present invention provides a nucleic acid encoding each of the three AAAV coat proteins, VP1, VP2, and VP3. Thus, the present invention provides a nucleic acid encoding AAAV VP1, a nucleic acid encoding AAAV VP2, and a nucleic acid encoding AAAV VP3. Thus, the present invention provides a nucleic acid encoding the amino acid sequence set forth in SEQ ID NO:11 (VP1); a nucleic acid encoding the amino acid sequence set forth in SEQ ID NO:13 (VP2), and a nucleic acid encoding the amino acid sequence set forth in SEQ ID NO:15 (VP3). The present invention also specifically provides a nucleic acid comprising SEQ ID NO:10 (VP1 gene); a nucleic acid comprising SEQ ID NO:12 (VP2 gene); and a nucleic acid comprising SEQ ID NO:14 (VP3 gene). The present invention also specifically provides a nucleic acid consisting essentially of SEQ ID NO:10 (VP1 gene), a nucleic acid consisting essentially of SEQ ID NO:12 (VP2 gene), and a nucleic acid consisting essentially of SEQ ID NO:14 (VP3 gene). The present invention also provides a nucleic acid comprising nucleotides 1347-2127 of SEQ ID NO:10 (encoding amino acids 449-709 of VP1). Minor modifications in the nucleotide sequences encoding the capsid, or coat, proteins are contemplated, as described above for other AAAV nucleic acids. However, in general, a modified nucleic acid encoding a capsid protein will have at least about 70%, about 75%, about 80%, about 85%, about 90%, about 93%, about 95%, about 98% or 100% homology to the capsid nucleic acid sequences described herein e.g., SEQ ID NOS: 10, 12, and 14, and the capsid polypeptide encoded therein will have overall about 70%, about 75%, about 80%, about 85%, about 90%, about 95%, about 98%, about 99% or 100% homology with the amino acid sequence described herein, e.g., SEQ ID NOS:11, 13, and 15. Nucleic acids that selectively hybridize with the nucleic acids of SEQ ID NOS: 10, 12, and 14 under the conditions described above are also provided.

The present invention also provides a cell containing one or more of the herein described nucleic acids, such as the AAAV genome, AAAV ORF1 and ORF2, each AAAV Rep protein gene, or each AAAV capsid protein gene. Such a cell can be any desired cell and can be selected based upon the use intended. For example, cells can include bacterial cells, yeast cells, insect cells, human HeLa cells and simian Cos cells as well as other human and mammalian cells and cell lines. Primary cultures as well as established cultures and cell lines can be used. Nucleic acids of the present invention can be delivered into cells by any selected means, in particular depending upon the target cells. Many delivery means are well-known in the art. For example, electroporation, calcium phosphate precipitation, microinjection, cationic or anionic liposomes, and liposomes in combination with a nuclear localization signal peptide for delivery to the nucleus can be utilized, as is known in the art. Additionally, if the nucleic acids are in a viral particle, the cells can simply be transduced with the virion by standard means known in the art for AAV transduction. Small amounts of the recombinant AAAV virus can be made to infect cells and produce more of itself.

The invention provides purified AAAV polypeptides. The term "polypeptide" as used herein refers to a polymer of amino acids and includes full-length proteins and fragments thereof. Thus, "protein," polypeptide," and "peptide" are often used interchangeably herein. Substitutions can be selected by known parameters to be neutral (see, e.g., Robinson W E Jr, and Mitchell W M., AIDS 4:S151-S162 (1990)). As will be appreciated by those skilled in the art, the invention also includes those polypeptides having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff, et al. (in *Atlas of Protein Sequence and Structure* 1978, Nat'l Biomed. Res. Found., Washington, D.C.). These modifications can result in changes in the amino acid sequence, provide silent mutations, modify a restriction site, or provide other specific mutations. The location of any modifications to the polypeptide will often determine its impact on function. Particularly, alterations in regions non-essential to protein function will be tolerated with fewer effects on function. Elsewhere in the application regions of the AAAV proteins are described to provide guidance as to where substitutions, additions or deletions can be made to minimize the likelihood of disturbing the function of the variant.

A polypeptide of the present invention can be readily obtained by any of several means. For example, the polypeptide of interest can be synthesized chemically by standard methods. Additionally, the coding regions of the genes can be recombinantly expressed and the resulting polypeptide isolated by standard methods. Furthermore, an antibody specific for the resulting polypeptide can be raised by standard methods (see, e.g., Harlow and Lane, *Antibodies: A Laboratory Manual*, Cold Spring Harbor Laboratory, Cold Spring Harbor, N.Y., 1988), and the protein can be isolated from a cell expressing the nucleic acid encoding the polypeptide by selective hybridization with the antibody. This protein can be purified to the extent desired by standard methods of protein purification (see, e.g., Sambrook et al., *Molecular Cloning: A Laboratory Manual*, 2nd Ed., Cold Spring Harbor Laboratory, Cold Spring Harbor, N.Y., 1989).

Typically, to be unique, a polypeptide fragment of the present invention will be at least about 5 amino acids in length; however, unique fragments can be 6, 7, 8, 9, 10, 20, 30, 40, 50, 60, 70, 80, 90, 100 or more amino acids in length. A unique polypeptide will typically comprise such a unique fragment; however, a unique polypeptide can also be determined by its overall homology. A unique polypeptide can be 6, 7, 8, 9, 10, 20, 30, 40, 50, 60, 70, 80, 90, 100 or more amino acids in length. Uniqueness of a polypeptide fragment can readily be determined by standard methods such as searches of computer databases of known peptide or nucleic acid sequences or by hybridization studies to the nucleic acid encoding the protein or to the protein itself, as known in the art. The uniqueness of a polypeptide fragment can also be determined immunologically as well as functionally. Uniqueness can be simply determined in an amino acid-by-amino acid comparison of the polypeptides.

An antigenic or immunoreactive fragment of this invention is typically an amino acid sequence of at least about 5 consecutive amino acids, and it can be derived from the AAAV polypeptide amino acid sequence. An antigenic AAAV fragment is any fragment unique to the AAAV protein, as described herein, against which an AAAV-specific antibody can be raised, by standard methods. Thus, the resulting antibody-antigen reaction should be specific for AAAV.

The present invention provides an isolated AAAV Rep protein. An AAAV Rep polypeptide is encoded by ORF1 of AAAV. The present invention also provides each individual AAAV Rep protein. Thus the present invention provides AAAV Rep 40 (e.g., SEQ ID NO: 9), or a unique fragment thereof. The present invention provides AAAV Rep 52 (e.g., SEQ ID NO: 5), or a unique fragment thereof. The present invention provides AAAV Rep 68 (e.g., SEQ ID NO: 7), or a unique fragment thereof. The present invention provides an example of AAAV Rep 78 (e.g., SEQ ID NO: 3), or a unique fragment thereof. By "unique fragment thereof" is meant any smaller polypeptide fragment encoded by an AAAV rep gene that is of sufficient length to be found only in the Rep polypeptide. Substitutions and modifications of the amino acid sequence can be made as described above and, further, can include protein processing modifications, such as glycosylation, to the polypeptide.

The present invention further provides an AAAV Capsid polypeptide or a unique fragment thereof. AAAV capsid polypeptide is encoded by ORF 2 of AAAV. The present invention further provides the individual AAAV capsid proteins, VP1, VP2 and VP3 or unique fragments thereof. Thus, the present invention provides an isolated polypeptide having the amino acid sequence set forth in SEQ ID NO:11 (VP1). The present invention additionally provides an isolated polypeptide having the amino acid sequence set forth in SEQ ID NO:13 (VP2). The present invention also provides an isolated polypeptide having the amino acid sequence set forth in SEQ ID NO:15 (VP3). By "unique fragment thereof" is meant any smaller polypeptide fragment encoded by any AAAV capsid gene that is of sufficient length to be found only in the AAAV capsid protein. Substitutions and modifications of the amino acid sequence can be made as described above and, further, can include protein processing modifications, such as glycosylation, to the polypeptide. However, an AAAV Capsid polypeptide including all three coat proteins will have greater than about 56% overall homology to the polypeptide encoded by the nucleotides set forth in SEQ ID NOS:10, 12 or 14. The protein can have about 65%, about 70%, about 75%, about 80%, about 85%, about 90%, 93%, 95%, 97% or even 100% homology to the amino acid sequence encoded by the nucleotides set forth in SEQ ID NOS: 10, 12 or 14. An AAAV VP1 polypeptide can have at least about 58%, about 60%, about 70%, about 80%, about 90%, 93%, 95%, 97% or about 100% homology to the amino acid sequence set forth in SEQ ID NO:10. An AAAV VP2 polypeptide can have at least about 58%, about 60%, about 70%, about 80%, about 90%, 93%, 95%, 97% or about 100% homology to the amino acid sequence set forth in SEQ ID NO:12. An AAAV VP3 polypeptide can have at least about 60%, about 70%, about 80%, about 90%, 93%, 95%, 97% or about 100% homology to the amino acid sequence set forth in SEQ ID NO:14.

The present invention further provides an isolated antibody that specifically binds an AAAV Rep protein or a unique epitope thereof. Also provided are isolated antibodies that specifically bind the AAAV Rep 52 protein, the AAAV Rep 40 protein, the AAAV Rep 68 protein and the AAAV Rep 78 protein having the amino acid sequences set forth in SEQ ID NO:5, SEQ ID NO: 9, SEQ ID NO: 7 and SEQ ID NO: 3, respectively or that specifically binds a unique fragment thereof. Clearly, any given antibody can recognize and bind one of a number of possible epitopes present in the polypeptide; thus only a unique portion of a polypeptide (having the epitope) may need to be present in an assay to determine if the antibody specifically binds the polypeptide.

The present invention additionally provides an isolated antibody that specifically binds any of the avian adeno-associated virus Capsid proteins (VP1, VP2 or VP3), a unique epitope thereof, or the polypeptide comprising all three AAAV coat proteins. Also provided is an isolated antibody that specifically binds the AAAV capsid protein having the amino acid sequence set forth in SEQ ID NO:11 (VP1), or that specifically binds a unique fragment thereof. The present invention further provides an isolated antibody that specifically binds the AAAV Capsid protein having the amino acid sequence set forth in SEQ ID NO:13 (VP2), or that specifically binds a unique fragment thereof. The invention additionally provides an isolated antibody that specifically binds the AAAV Capsid protein having the amino acid sequence set forth in SEQ ID NO:15 (VP3), or that specifically binds a unique fragment thereof. Again, any given antibody can recognize and bind one of a number of possible epitopes present in the polypeptide; thus only a unique portion of a polypeptide (having the epitope) may need to be present in an assay to determine if the antibody specifically binds the polypeptide.

The antibody can be a component of a composition that comprises an antibody that specifically binds the AAAV protein. The composition can further comprise, e.g., serum, serum-free medium, or a pharmaceutically acceptable carrier such as physiological saline, etc.

By "an antibody that specifically binds" an AAAV polypeptide or protein is meant an antibody that selectively binds to an epitope on any portion of the AAAV peptide such that the antibody binds specifically to the corresponding AAAV polypeptide without significant background. Specific binding by an antibody further means that the antibody can be used to selectively remove the target polypeptide from a sample comprising the polypeptide or and can readily be determined by radioimmunoassay (RIA), bioassay, or enzyme-linked immunosorbant (ELISA) technology. An ELISA method effective for the detection of the specific antibody-antigen binding can, for example, be as follows: (1) bind the antibody to a substrate; (2) contact the bound antibody with a sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe the color change.

An antibody can include antibody fragments such as Fab fragments which retain the binding activity. Antibodies can be made as described in, e.g., Harlow and Lane, *Antibodies: A Laboratory Manual*, Cold Spring Harbor Laboratory, Cold Spring Harbor, N.Y. (1988). Briefly, purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. Individual hybridomas are then propagated as individual clones serving as a source for a particular monoclonal antibody.

The present invention additionally provides a method of screening a cell for infectivity by AAAV comprising contacting the cell with AAAV and detecting the presence of AAAV in the cells. AAAV particles can be detected using any standard physical or biochemical methods.

The present invention provides a method of screening for cells that are permissive to AAAV infection comprising identifying the presence of N-linked terminal lactose on the surface of a cell, contacting the N-linked terminal lactose containing cell with AAAV and detecting the presence of AAAV virus in the cell, whereby if AAAV virus is detected in the cells, the N-linked terminal lactose containing cell is permissive to AAAV infection. In one example of such a method, based on the teaching in the Examples, uses *Erythrina corralodendron* lectin to detect cells that would allow efficient binding of AAAV and possible transduction. A closely related method using sialic acid binding lectins to screen for AAV5 transduction is described in Walters et al. (Adeno-associated virus serotype 4 (AAV4) and AAV5 both require sialic acid binding for hemagglutination and efficient transduction but differ in sialic acid linkage specificity, J Virol. 2001 August; 75(15):6884-93, incorporated herein by reference).

For the screening methods of the present invention, monoclonal antibodies to different forms of conjugated lactose can be produced (Sato et al JBC 2000. May 19; 275(20):15422-31). Cells are contacted with these antibodies to select cells that contain the appropriate N-linked terminal lactose. A number of antibodies exist which bind specific lactose conjugates and can be used to screen for N-linked terminal lactose containing cells. These antibodies can be fluorescently labeled and used in situ. Alternatively, antibodies can be bound to a plate and target cells added. The wells are then washed and cells that express the antigen will bind to the N-linked terminal lactose antibody. Cells that bind to the sialic acid can be visualized by staining. Another way to screen for permissive cells is to chemically remove the glycans from the cell surface and fractionate these by thin layer chromatography. The presence of the correct form of N-linked terminal lactose can be confirmed by hybridizing the blot with labeled virus. Free virus is washed off and the specifically bound virus visualized by detecting the label. Alternatively, whole membrane proteins could be used and separated by PAGE, transferred to a membrane and probed as described above.

Additionally, physical methods that can be used for this detection include DNA based methods such as 1) polymerase chain reaction (PCR) for viral DNA or RNA or 2) direct hybridization with labeled probes, and immunological methods such as by 3) antibody directed against the viral structural or non-structural proteins. Catalytic methods of viral detection include, but are not limited to, detection of site and strand specific DNA nicking activity of Rep proteins or replication of an AAV origin-containing substrate. Reporter genes can also be utilized to detect cells that transduce AAAV. For example, β-gal, green fluorescent protein or luciferase can be inserted into a recombinant AAAV. The cell can then be contacted with the recombinant AAAV, either in vitro or in vivo and a calorimetric assay could detect a color change in the cells that would indicate transduction of AAAV in the cell. Additional detection methods are outlined in Fields, *Virology*, Raven Press, New York, N.Y. 1996.

For screening a cell for infectivity by AAAV, wherein the presence of AAAV in the cells is determined by nucleic acid hybridization methods, a nucleic acid probe for such detection can comprise, for example, a unique fragment of any of the AAAV nucleic acids provided herein. The uniqueness of any nucleic acid probe can readily be determined as described herein. Additionally, the presence of AAAV in cells can be determined by fluorescence, antibodies to gene products, focus forming assays, plaque lifts, Western blots and chromogenic assays. The nucleic acid can be, for example, the nucleic acid whose nucleotide sequence is set forth in SEQ ID NO: 1, 2, 4, 6, 8, 10, 12, 14, and 16-24 or a unique fragment thereof.

The present invention includes a method of determining the suitability of an AAAV vector for administration to a subject comprising administering to an antibody-containing sample from the subject an antigenic fragment of an isolated AAAV Rep or Capsid protein, and detecting neutralizing antibody-antigen reaction in the sample, the presence of a neutralizing reaction indicating the AAAV vector may be unsuitable for use in the subject. The present method of determining the suitability of an AAAV vector for administration to a subject can comprise contacting an antibody-containing sample from the subject with a unique antigenic or immunogenic fragment of an AAAV Rep protein (e.g. Rep 40, Rep 52, Rep 68, Rep 78) and detecting an antibody-antigen reaction in the sample, the presence of a reaction indicating the AAAV vector to be unsuitable for use in the subject. The AAAV Rep proteins are provided herein, and their antigenic fragments are routinely determined. The AAAV capsid protein can be used to select an antigenic or immunogenic fragment, for example from the amino acid sequence set forth in SEQ ID NO:11 (VP1), the amino acid sequence set forth in SEQ ID NO: 13 (VP2) or the amino acid sequence set forth in SEQ ID NO:15 (VP3). Alternatively, or additionally, an antigenic or immunogenic fragment of an isolated AAAV Rep protein can be utilized in this determination method. The AAAV Rep protein from which an antigenic fragment is selected can have the amino acid sequence encoded by the nucleic acid set forth in SEQ ID NO:1, the amino acid sequence set forth in SEQ ID NO:3, or the amino acid sequence set forth in SEQ ID NO:5, the amino acid sequence set forth in SEQ ID NO: 7, or the amino acid sequence set forth in SEQ ID NO:9.

The AAAV polypeptide fragments can be analyzed to determine their antigenicity, immunogenicity and/or specificity. Briefly, various concentrations of a putative immunogenically specific fragment are prepared and administered to a subject and the immunological response (e.g., the production of antibodies or cell mediated immunity) of an animal to each concentration is determined. The amounts of antigen administered depend on the subject, e.g. a human, rabbit or a guinea pig, the condition of the subject, the size of the subject, etc. Thereafter an animal so inoculated with the antigen can be exposed to the AAAV viral particle or AAAV protein to test the immunoreactivity or the antigenicity of the specific immunogenic fragment. The specificity of a putative antigenic or immunogenic fragment can be ascertained by testing sera, other fluids or lymphocytes from the inoculated animal for cross reactivity with other closely related viruses, such as AAV1-8.

By the "suitability of an AAAV vector for administration to a subject" is meant a determination of whether the AAAV vector will elicit a neutralizing immune response upon administration to a particular subject. A vector that does not elicit a significant immune response is a potentially suitable vector, whereas a vector that elicits a significant, neutralizing immune response (e.g. at least 90%) is thus likely to be unsuitable for use in that subject. Significance of any detectable immune response is a standard parameter understood by the skilled artisan in the field. For example, one can incubate the subject's serum with the virus, then determine whether that virus retains its ability to transduce cells in culture. If such virus cannot transduce cells in culture, the vector likely has elicited a significant immune response.

Alternatively, or additionally, one skilled in the art could determine whether or not AAAV administration would be suitable for a particular cell type of a subject. For example, the artisan could culture muscle cells in vitro and transduce the cells with AAAV in the presence or absence of the subject's serum. If there is a reduction in transduction efficiency, this could indicate the presence of a neutralizing antibody or other factors that may inhibit transduction. Normally, greater than 90% inhibition would have to be observed in order to rule out the use of AAAV as a vector. However, this limitation could be overcome by treating the subject with an immunosuppressant that could block the factors inhibiting transduction.

As will be recognized by those skilled in the art, numerous types of immunoassays are available for use in the present invention to detect binding between an antibody and an AAAV polypeptide of this invention. For instance, direct and indirect binding assays, competitive assays, sandwich assays, and the like, as are generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, N.Y. (1988). For example, enzyme immunoassays such as immunofluorescence assays (IFA), enzyme linked immunosorbent assays (ELISA) and immunoblotting can be readily adapted to accomplish the detection of the antibody. An ELISA method effective for the detection of the antibody bound to the antigen can, for example, be as follows: (1) bind the antigen to a substrate; (2) contact the bound antigen with a fluid or tissue sample containing the antibody; (3) contact the above with a secondary antibody specific for the antigen and bound to a detectable moiety (e.g., horseradish peroxidase enzyme or alkaline phosphatase enzyme); (4) contact the above with the substrate for the enzyme; (5) contact the above with a color reagent; (6) observe color change.

The antibody-containing sample of this method can comprise any biological sample which would contain the antibody or a cell containing the antibody, such as blood, plasma, serum, bone marrow, saliva, urine and mucus.

The present invention also provides a method of producing the AAAV virus by transducing a cell with the nucleic acid encoding the virus. The present invention also provides AAAV produced by the method of transducing a cell with the nucleic acid encoding the virus.

The present method further provides a method of delivering an exogenous (heterologous) nucleic acid to a cell comprising administering to the cell an AAAV particle containing a vector comprising the nucleic acid inserted between a pair of AAV inverted terminal repeats, thereby delivering the nucleic acid to the cell.

The AAV ITRs in the vector for the herein described delivery methods can be AAAV ITRs (SEQ ID NOS: 16 and 17). Furthermore, the AAV ITRs in the vector for the herein described nucleic acid delivery methods can also comprise AAV1-8 inverted terminal repeats.

The present invention also includes a method of delivering a heterologous nucleic acid to a subject comprising administering to a cell from the subject an AAAV particle containing a vector comprising the nucleic acid inserted between a pair of AAV inverted terminal repeats, and returning the cell to the subject, thereby delivering the nucleic acid to the subject. The AAV ITRs can be any AAV ITRs, including AAAV ITRs, AAV5 ITRs and AAV2 ITRs. For example, in an ex vivo administration, cells are isolated from a subject by standard means according to the cell type and placed in appropriate culture medium, again according to cell type (see, e.g., ATCC catalog). Viral particles are then contacted with the cells as described above, and the virus is allowed to transduce the cells. Cells can then be transplanted back into the subject's body, again by means standard for the cell type and tissue (e.g., in general, U.S. Pat. No. 5,399,346; for neural cells, Dunnett, S. B. and Björklund, A., eds., *Transplantation: Neural Transplantation—A Practical Approach*, Oxford University Press, Oxford (1992)). If desired, prior to transplantation, the cells can be studied for degree of transduction by the virus, by known detection means and as described herein. Cells for ex vivo transduction followed by transplantation into a subject can be selected from those listed above, or can be any other selected cell. Preferably, a selected cell type is examined for its capability to be transfected by AAAV. Preferably, the selected cell will be a cell readily transduced with AAAV particles; however, depending upon the application, even cells with relatively low transduction efficiencies can be useful, particularly if the cell is from a tissue or organ in which even production of a small amount of the protein or antisense RNA encoded by the vector will be beneficial to the subject.

The present invention further provides a method of delivering a nucleic acid to a cell in a subject comprising administering to the subject an AAAV particle containing a vector comprising the nucleic acid inserted between a pair of AAV inverted terminal repeats, thereby delivering the nucleic acid to a cell in the subject. Administration can be an ex vivo administration directly to a cell removed from a subject, such as any of the cells listed above, followed by replacement of the cell back into the subject, or administration can be in vivo administration to a cell in the subject. For ex vivo administration, cells are isolated from a subject by standard means according to the cell type and placed in appropriate culture medium, again according to cell type (see, e.g., ATCC catalog). Viral particles are then contacted with the cells as described above, and the virus is allowed to transfect the cells. Cells can then be transplanted back into the subject's body, again by means standard for the cell type and tissue (e.g., for neural cells, Dunnett, S. B. and Björklund, A., eds., *Transplantation: Neural Transplantation—A Practical Approach*, Oxford University Press, Oxford (1992)). If desired, prior to transplantation, the cells can be studied for degree of transfection by the virus, by known detection means and as described herein.

The present invention further provides a method of delivering a nucleic acid to a cell in a subject having neutralizing antibodies to AAV1-8 comprising administering to the subject an AAAV particle containing a vector comprising the nucleic acid, thereby delivering the nucleic acid to a cell in the subject. A subject that has neutralizing antibodies to AAV1-8 can readily be determined by any of several known means, such as contacting AAV1-8 protein(s) with an antibody-containing sample, such as blood, from a subject and detecting an antigen-antibody reaction in the sample. Delivery of the AAV1-8 particle can be by either ex vivo or in vivo administration as herein described. Thus, a subject who might have an adverse immunogenic reaction to a vector administered in an AAV2 viral particle can have a desired nucleic acid delivered using an AAV1-8 particle. This delivery system can be particularly useful for subjects who have received therapy utilizing AAV1-8 particles in the past and have developed antibodies to AAV1-8. An AAAV regimen can now be substituted to deliver the desired nucleic acid.

In any of the methods of delivering heterologous nucleic acids to a cell or subject described herein, the AAAV-conjugated nucleic acid or AAAV particle-conjugated nucleic acids described herein can be used.

In vivo administration to a human subject or an animal model can be by any of many standard means for administering viruses, depending upon the target organ, tissue or cell. Virus particles can be administered orally, parenterally (e.g., intravenously), by intramuscular injection, by direct tissue or organ injection, by intraperitoneal injection, topically, transdermally, via aerosol delivery, via the mucosa or the like. Viral nucleic acids (non-encapsidated) can also be administered, e.g., as a complex with cationic liposomes, or encapsulated in anionic liposomes. The present compositions can include various amounts of the selected viral particle or non-encapsidated viral nucleic acid in combination with a pharmaceutically acceptable carrier and, in addition, if desired, may include other medicinal agents, pharmaceutical agents, carriers, adjuvants, diluents, etc. Parental administration, if used, is generally characterized by injection. Injectables can be prepared in conventional forms, either as liquid solutions or suspensions, solid forms suitable for solution or suspension in liquid prior to injection, or as emulsions. Dosages will depend upon the mode of administration, the disease or condition to be treated, and the individual subject's condition, but will be that dosage typical for and used in administration of other AAV vectors, such as AAV2 vectors. Often a single dose can be sufficient; however, the dose can be repeated if desirable.

Administration methods can be used to treat brain disorders such as Parkinson's disease, Alzheimer's disease, and demyelination disease. Other diseases that can be treated by these methods include metabolic disorders such as, muscoloskeletal diseases, cardiovascular disease, cancer, and autoimmune disorders.

Administration of this recombinant AAAV virion to the cell can be accomplished by any means, including simply contacting the particle, optionally contained in a desired liquid such as tissue culture medium, or a buffered saline solution, with the cells. The virion can be allowed to remain in contact with the cells for any desired length of time, and typically the virion is administered and allowed to remain indefinitely. For such in vitro methods, the virion can be administered to the cell by standard viral transduction methods, as known in the art and as exemplified herein. Titers of virus to administer can vary, particularly depending upon the cell type, but will be typical of that used for AAV transduction in general which is well known in the art. Additionally the titers used to transduce the particular cells in the present examples can be utilized.

The cells that can be transduced by the present recombinant AAAV virion can include any desired cell, such as the following cells and cells derived from the following tissues, human as well as other mammalian tissues, such as primate, horse, sheep, goat, pig, dog, rat, and mouse and avian species: Adipocytes, Adenocyte, Adrenal cortex, Amnion, Aorta, Ascites, Astrocyte, Bladder, Bone, Bone marrow, Brain, Breast, Bronchus, Cardiac muscle, Cecum, Cervix, Chorion, Colon, Conjunctiva, Connective tissue, Cornea, Dermis, Duodenum, Endometrium, Endothelium, Endothelial cells, Epithelial tissue, Epithelial cells, Epidermis, Esophagus, Eye, Fascia, Fibroblasts, Foreskin, Gastric, Glial cells, Glioblast, Gonad, Hepatic cells, Histocyte, Ileum, Intestine, small Intestine, Jejunum, Keratinocytes, Kidney, Larynx, Leukocytes, Lipocyte, Liver, Lung, Lymph node, Lymphoblast, Lymphocytes, Macrophages, Mammary alveolar nodule, Mammary gland, Mastocyte, Maxilla, Melanocytes, Mesenchymal, Monocytes, Mouth, Myelin, Myoblasts Nervous tissue, Neuroblast, Neurons, Neuroglia, Osteoblasts, Osteogenic cells, Ovary, Palate, Pancreas, Papilloma, Peritoneum, Pituicytes, Pharynx, Placenta, Plasma cells, Pleura, Prostate, Rectum, Salivary gland, Skeletal muscle, Skin, Smooth muscle, Somatic, Spleen, Squamous, Stomach, Submandibular gland, Submaxillary gland, Synoviocytes, Testis, Thymus, Thyroid, Trabeculae, Trachea, Turbinate, Umbilical cord, Ureter, and Uterus.

The methods of the present invention are also useful for the delivery of AAAV vectors that express ribozymes or small interfering RNAs (siRNAs). Both methods can reduce protein expression by minimizing or completely abolishing mRNA levels of targeted genes. Applications in the poultry industry are also contemplated. These include delivery of a ribozyme or siRNA against chicken myostatin, a gene controlling muscle mass. In addition, the ability of AAAV vectors to deliver genes to a variety of tissues to express genetic information effectively for long periods of time, and to have a good safety profile make avian AAVs an attractive vector for genetic immunization of chickens. Avian AAV vectors could be used for in ovo or post-hatch vaccination of chickens against diseases such as Marek's, coccidiosis, Newcastle disease, etc.

Also, a hallmark of avian AAV infection is the inhibition of avian viruses during co-infection. The present invention shows that this is a function of the avian AAV non-structural proteins. Incorporation of these sequences into a viral vector or addition of recombinant protein to eggs could be used as a method to inhibit viral infection and promote growth/development.

A method of blocking AAAV infection is provided. The method is based on the findings in the Examples that AAAV requires N-linked terminal lactose present on cell surface proteins for efficient binding and entry. Thus, lactose conjugates, dendrimer nanoparticles with terminal lactose, or *Erythrina corralodendron* lectin can be used as agents to block AAAV infection of a cell. The synthesis of dendrimers has been described (Schchepinov, M. S., Udalova, I. A., Bridgman, A. J., Southern, E. M., 1997, Nucleic Acids Res. 25:4447-4454).

A method of inducing an immune response to AAAV in a subject comprising administering an AAAV particle comprising the capsid protein (SEQ ID NO: 11, SEQ ID NO: 12 or SEQ ID NO:13) or epitope thereof, wherein the capsid protein or epitope thereof comprises an epitope that induces an immune response in a subject. The capsid protein can also include epitopes of other (non-AAAV) proteins (as described herein) such that an immune response is directed against the non-AAAV epitope.

A method of blocking an immune response against AAAV in a subject comprising administering an AAAV particle comprising the capsid protein (SEQ ID NO: 11, SEQ ID NO: 12 or SEQ ID NO:13) or epitope thereof, wherein the capsid protein or epitope thereof comprises an epitope that blocks the immune response to AAAV in a subject. The capsid protein can also include epitopes of other (non-AAAV) proteins (as described herein) such that the immune response that is blocked is an immune response directed against the non-AAAV epitope.

A method of producing a recombinant protein is provided, comprising administering an AAAV particle comprising an exogenous nucleic acid encoding a protein to an embryonated avian egg; and b) purifying the protein from the egg. The protein purified by a method of the invention is also provided.

EXAMPLES

To understand the nature of AAAV virus and to determine its usefulness as a vector for gene transfer, it was cloned and sequenced.

Materials and Methods
Cell Culture and Virus Propagation.

293T and COS cells were maintained in IMEM and AMEM, respectively, containing 10% FBS, DF1 cells (spontaneously immortalized chicken embryonic fibroblasts), QNR cells (quail neuroretinal cells), A549 and primary chicken embryonic fibroblasts (CEF) were maintained in DMEM supplemented with 10% FBS, primary chicken embryonic kidney cells were maintained in BME supplemented with 10% FBS, primary chicken pituitary cells were maintained in DMEM supplemented with 5% horse serum, QT6 cells (quail fibrosarcoma) were maintained in Ham's F12K supplemented with 10% FBS, LMH cells (chicken hepatoma cells) cells were maintained in Waymouth's media supplemented with 10% FBS, DT-90 (chicken lymphoblastoma cells) were maintained in DMEM supplemented with 15% FBS, 5% chicken serum and 0.015% β-mercaptoethanol. Human primary fibroblasts were obtained from Clonetics and maintained in serum-free proprietary medium supplied by the manufacturer. AAAV (ATCC, VR-865) was propagated in ten day old Spafas pathogen free embryonated chick eggs co-infected with the Phelps strain of fowl adenovirus type I (FAV1; ATCC, VR-486). AAAV at $10^4$-$10^7$ and FAV1 at $10^5$ infectious particles in saline were simultaneously injected in the chorioallantoic cavity of eggs and incubated for 96 hrs at 37 C. At the end of the incubation allantoamniotic fluids (AAFs) were harvested and clarified by centrifugation at 6000 g for 10 min.

Viral DNA Isolation, Cloning and Sequencing.

Virus from infected clarified AAFs was precipitated by centrifugation at 100,000 g for 2 hr. The supernatant was discharged and the virus-containing pellet was resuspended in proteinase K digestion buffer (50 mM Tris pH=8, 20 mM EDTA, 0.5% SDS, 200 µg/ml proteinase K) and incubated at 45 C for 2 h. Following a phenol-chloroform extraction and ethanol precipitation, the viral DNA was resuspended in TE buffer containing 0.1 M Nacl. The single stranded viral DNA was annealed by heating to 95 C for 5 min followed by slow cooling to 65 C for 6 h. The annealed viral DNA was separated electrophoretically in 1% agarose gel and the double stranded AAAV DNA of approximately 4.7 kb was excised and purified using a gel extraction kit (Qiagen). The viral DNA was further processed to fill in the ends by treating with DNA polymerase (Klenow fragment) at 37 C for 15 min in the presence of dNTPs. The whole genome was then blunt end cloned in the pPCR-script cloning vector containing the LacZ gene allowing blue-white screening of ampicilin resistant colonies (Stratagene). Colonies that contained large inserts (4.7 kb) were initially screened by restriction digestion and three clones were selected for sequencing. No sequence differences were found in these three clones. Sequence of the entire genome (except ITRs) was determined using an ABI 373A automated sequencer and FS dye-terminator chemistry (ABI). Due to high degree of secondary structure, ITRs were sequenced by isothermal non-cycling sequencing chemistry using radiolabeled dCTP (Epicentre). One of the clones (PAAAV) that contained the entire consensus sequence of AAAV was further used to generate packaging and vector plasmids for construction of recombinant AAAV (rAAAV) virus. The complete DNA sequence of AAAV have been submitted to GenBank (Accession number AY186198).

Sequence Analysis.

DNA and protein sequence alignments were performed using the Clustal W multiple sequence alignment tool of the Biology Workbench web based software (SDSC). Promoters, transcription initiation and splice sites were predicted using the Neural Network Promoter Prediction web paged software (BDGP). The presence of potential transcription binding sites was analyzed using the MatInspector computer program (54). Putative motifs in the Rep proteins were identified using the BLIMPS program that search for motifs in the Blocks protein database (28).

Southern Blot Hybridization.

The ability of pAAAV to support self-excision, packaging and generation of nuclease resistant wild type AAAV particles was examined. 293T cells seeded in 6-well plates were transfected using calcium phosphate co-precipitation with pAAAV alone, pAAAV plus pAd12 (a helper plasmid containing the E2 and E4 ORFs and VA RNAs of Ad5) and pAAAV plus infection with Ad5. In addition, LMH cells seeded in gelatin-coated 6-well plates were similarly transfected with pAAAV alone or with pAAAV plus infection with FAV1. After 48 hr, clarified lysates were prepared using three freeze-thaw cycles and centrifugation at 3800×g for 20 min. The lysate (~100 µl) was treated with 5 units of DNAse for 2 hr at 37 to remove vector and unpackaged progeny. Subsequently, the solution were adjusted to contain 20 mM EDTA (pH=8), 0.5% SDS and 200 µg/ml proteinase K and incubated at 45 C for 2 hr. After one phenol-chloroform extraction, nucleic acids were precipitated with addition of an equal volume of isopropanol, and the pellet was resuspended in 30 µl of TE buffer containing 0.1 M NaCl. The samples were heated to 95 C for 5 min, slowly cooled down to 65 C at which point and incubated for 5 hr. After electrophoresis and blotting, the membrane was probed with a $^{32}$P-labeled 1.2 kb BamH1 fragment of pAAAV.

Generation of Recombinant AAAV Particles.

For production of recombinant particles we three different helper plasmids were generated and examined, pMA$_3$VRC, pCA$_3$VRC, pA$_3$VRC, containing the AAAV rep and cap genes under control of an MMTV, CMV or the native p5 promoters, respectively. For generation of pMA$_3$VRC, the rep and cap ORFs (nucleotides 243-4482) was produced by PCR with pfu polymerase (Stratagene) as specified by the manufacturer using primers containing BstZ107 and NotI sites. The PCR products were digested with BstZ107 and NotI and ligated in a BstZ107/NotI fragment of pMMTV2.1 (18) containing an MMTV promoter and SV40 polyA. For generation of pCA₃VRC, the rep and cap ORFs (nucleotides 243-4482) was produced by PCR with pfu polymerase and blunt end ligated in the pCMV-script (Stratagene) vector, which contains a CMV promoter and SV40 polyA. For generation of pA₃VRC, the rep and cap genes of AAAV including the p5 promoter and polyA signal (nucleotides 142-4516) was produced by PCR using pfu polymerase and blunt-end ligated in pPCR-script. Orientation of inserts was verified by restriction digestion analysis, and final clones confirmed by sequencing. For generation of the vector carrying the β-galactosidase gene flanked by AAAV ITRs, the plasmid pAAAV was digested with BsmB1 (NEB). BsmB1 does not cut in the plasmid backbone but cut at positions 838, 1111, 2590, 4419 and 4530 of the AAAV genome. The resulting fragment that contained the plasmid backbone and 700 bp of AAAV genome flanked by ITRs was used to ligated a BsmB1-BsmI linker. The resulting plasmid was digested with Pml1 (cuts at nucleotide 146 of AAAV genome) and BsmI and used to ligated a BstZ107-BsmI fragment of pAAV₂RnLacZ (18) that contains the P-galactosidase gene under control of an RSV promoter and SV40 polyA tail. The resulting plasmid (pA₃VRSVβGal) was co-transfected with one of the helper plasmids described above and pAd12 in 293T cells plated in 150 cm dishes. Forty-eight hours post-transfection, cells were harvested and quantitated with a hematocytometer, and rAAAV prepared using standard CsCl gradient purification. The number of rAAAV genomes was estimated using real time quantitative PCR (QPCR) and expressed as nuclease resistant particles per cell recovered after transfections (DRP/cell). Titration of rAAAV was performed in exponentially growing CEF, DF-1, LMH, QNR, QT6, DT-90, 293T, COS and primary embryonic chicken kidney cells and non-dividing primary pituitary cells plated in 96 well plates, and transduced with serial dilutions of recombinant virus for 48 h as previously described (20).

To obtain AAAV genomic DNA for cloning, a stock of AAAV was obtained from ATCC (VR-865) and coinfected with Fowl adenovirus type I in day 10 embryonated chicken eggs. Virus was concentrated after subjecting infected allantoamniotic fluids to high-speed centrifugation. Viral DNA was released by SDS-Proteinase K digestion and purified by gel electrophoresis after annealing the complementary single strands by heating the purified DNA to 95° C. and slowly cooling to 65° C. Preliminary experiments indicated that 10⁵ infectious particles of FAV1 resulted in productive infection without succumbing the embryo prematurely. Co-infection with at least 10⁵ infectious particles of AAAV was required to detect viral DNA (~4.7 kb) by ethidium bromide staining. After recovery and end-filling, the double stranded AAAV genome was blunt-end ligated and cloned into pPCR-script. Several clones that contained an insert of approximately 4.7 kb were initially screened by restriction digestion and all gave bands similar in size to those previously reported (30). Three of these clones were sequenced and all gave identical sequences. One of the clones was randomly selected and used in subsequent analysis (pAAAV).

To verify that pAAAV can support self-excision, viral DNA replication, and packaging in mammalian and avian cells, viral lysates were prepared from 293T and LMH cells transfected with pAAAV and infected with wild type Ad5 or FAV1, respectively. In addition, the ability of an Ad5 plasmid to provide helper functions was examined in 293T cells. Southern blot analysis showed encapsidated (nuclease resistant particles) AAAV progeny in the presence of wtAd5 or Ad helper plasmid in 293T cells and FAV1 in LMH cells but not in the absence (FIGS. 1a and b). This result suggests that pAAAV can support rescue of AAAV in mammalian and avian cells in the presence of mammalian or avian adenoviral genes.

Figure 3A:
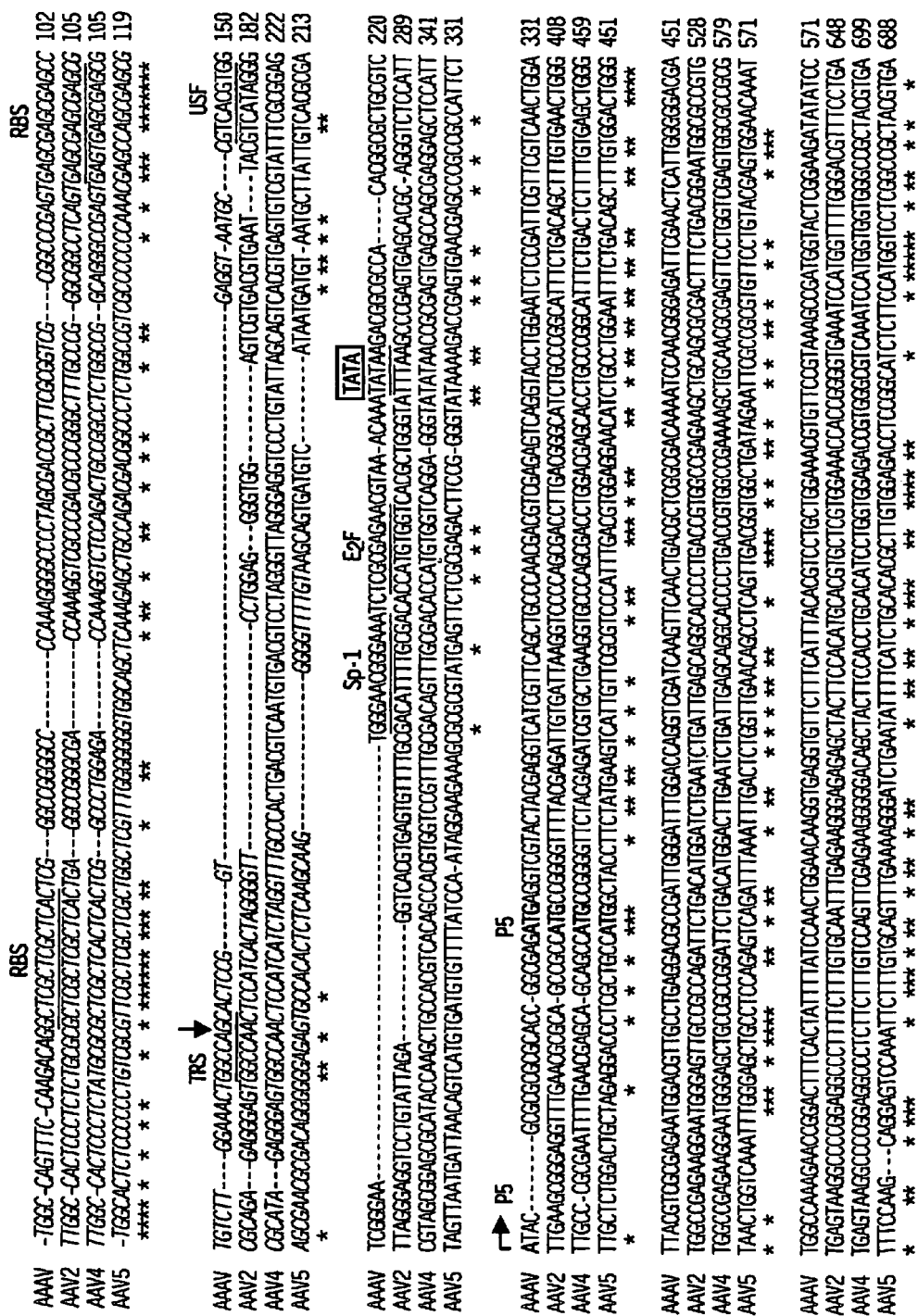
FIG. 3 is the sequence of an AAAV genome. The genomes of AAAV (SEQ ID NO:1), AAV2 (SEQ ID NO:26), AAV4 (SEQ ID NO:27) and AAV5 (SEQ ID NO:28) were aligned using Clustal W. The sequences of the ITRs are presented in italics. The putative trs is indicated by vertical arrow and the putative RBS is underlined. Proposed transcription factor binding sites and the polyadenylation signal are also underlined. Proposed transcription initiation sites of the p5, p19 and p40 promoters and splice donor and acceptor sites are indicated by horizontal arrows. Initiation and termination codons are presented in bold letters.
Figure 3B:
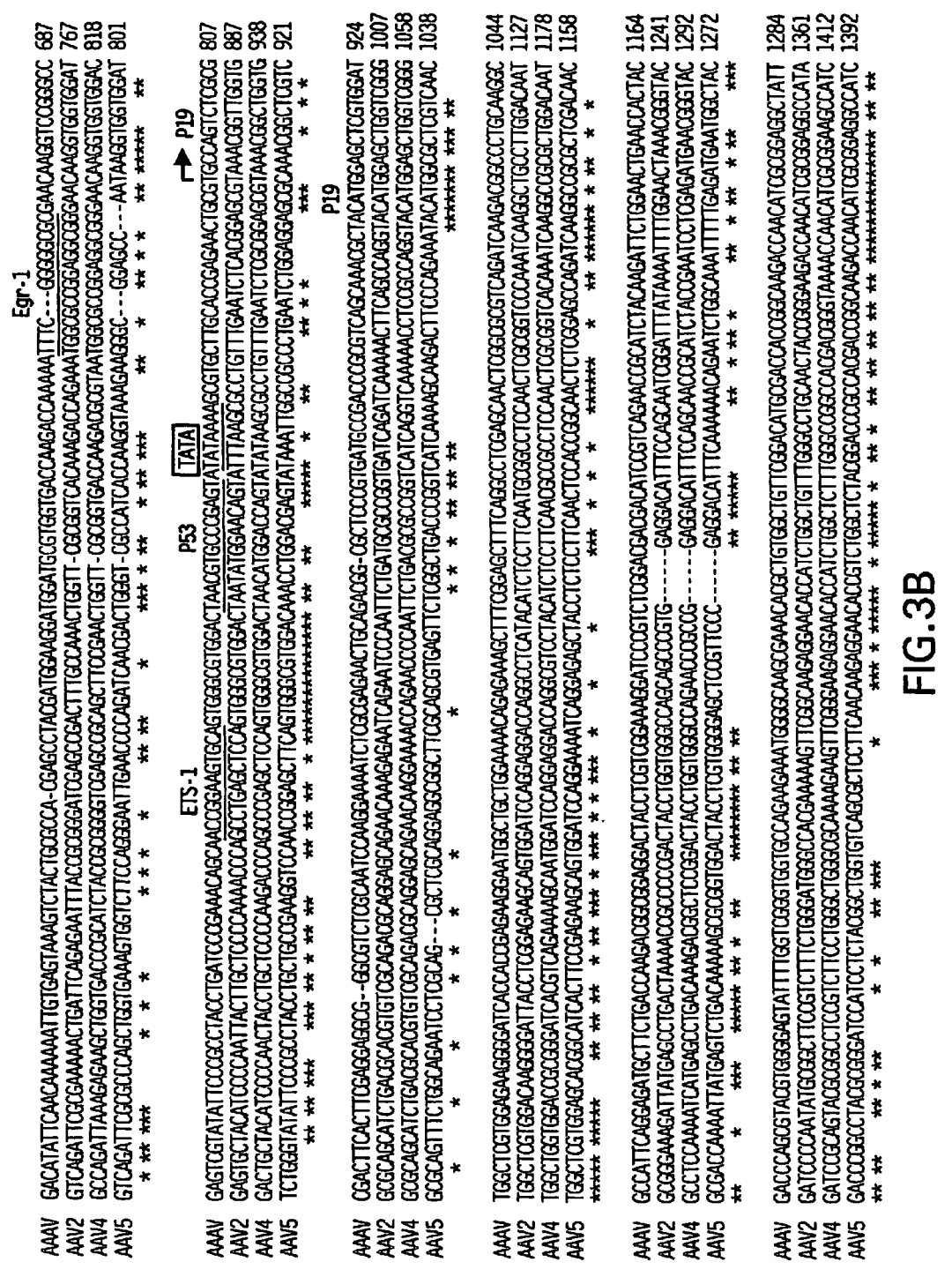
Figure 3C:
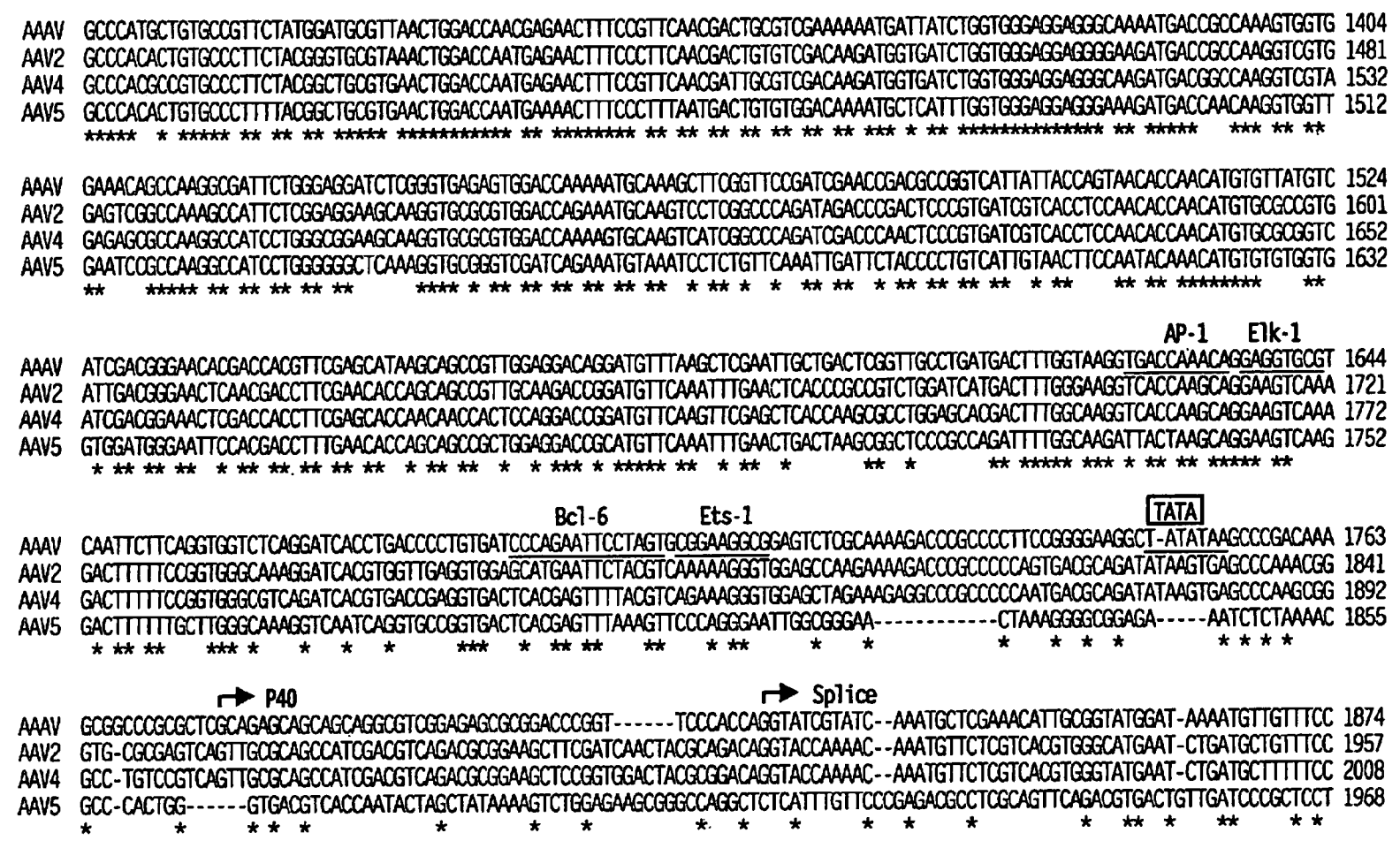
Figure 3D:
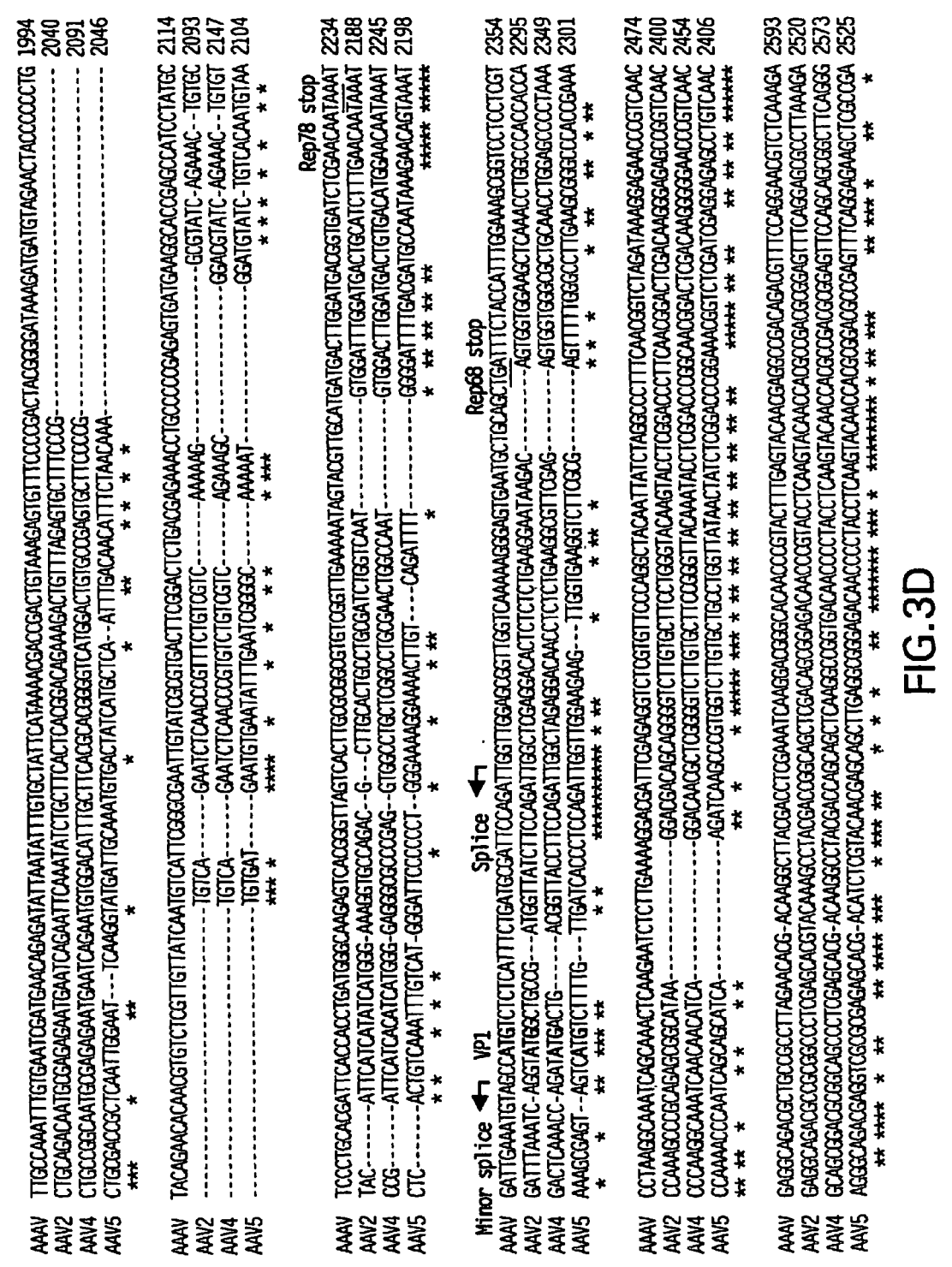
Figure 3E:
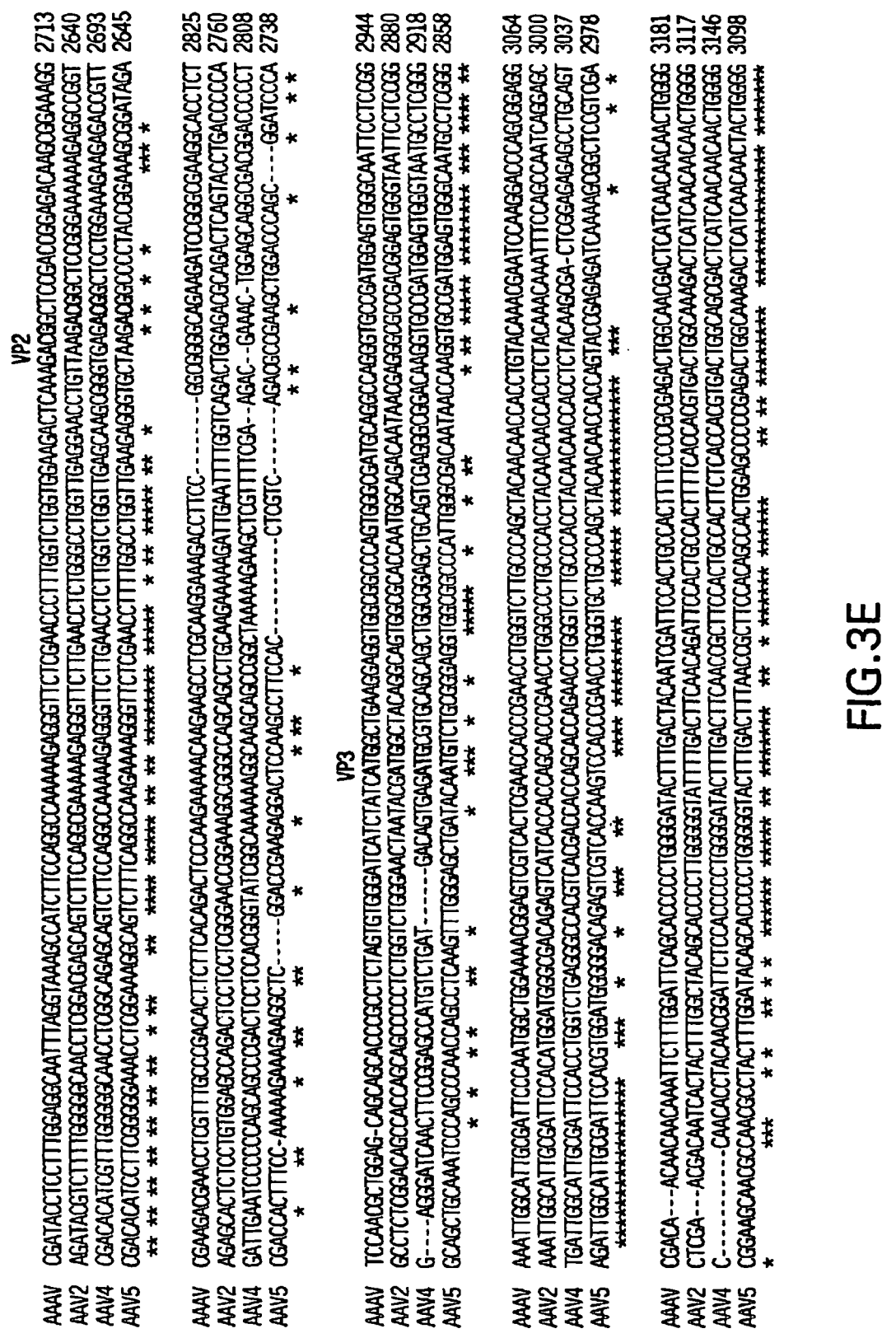
Figure 3F:
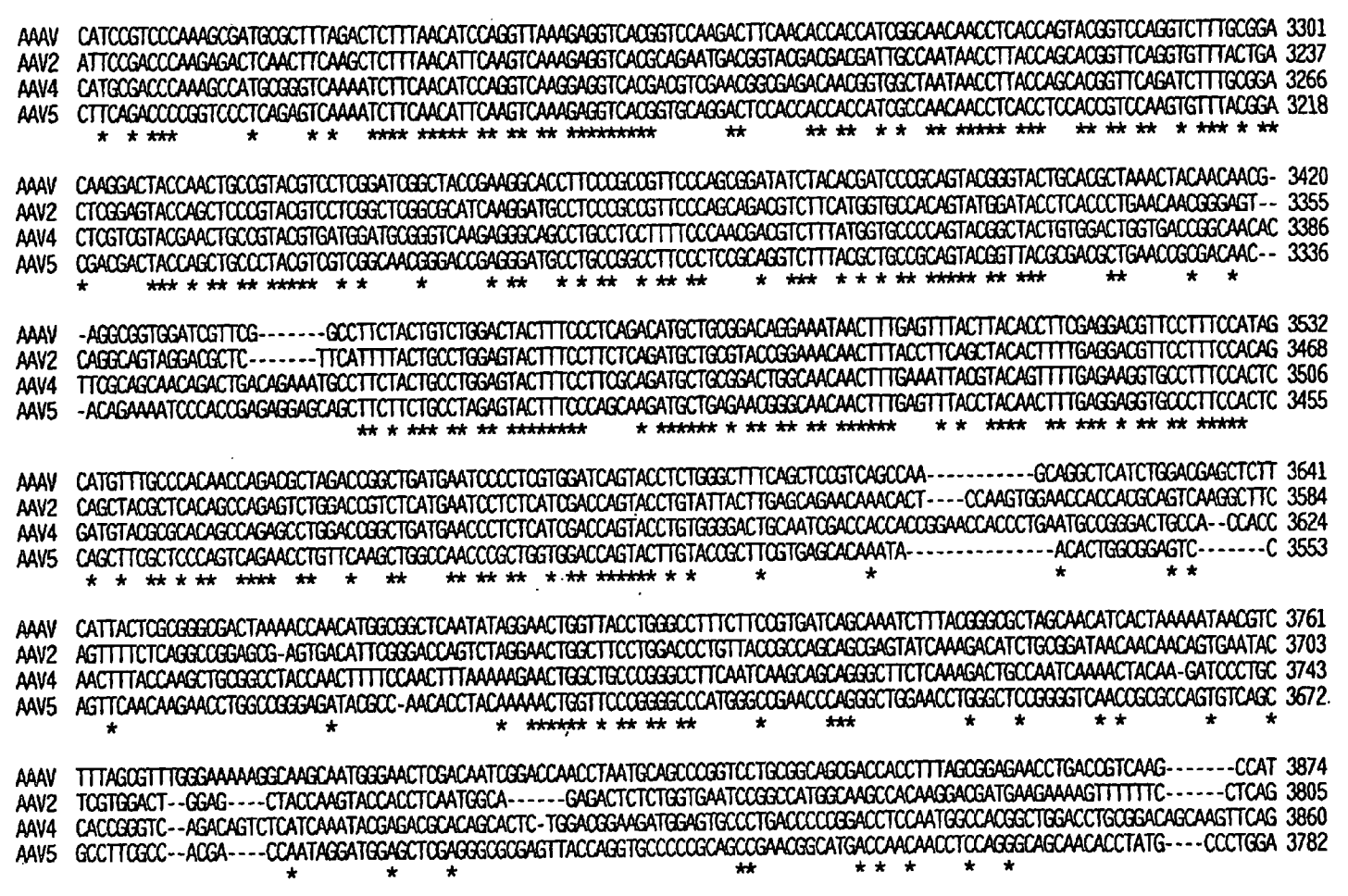
Figure 3G:
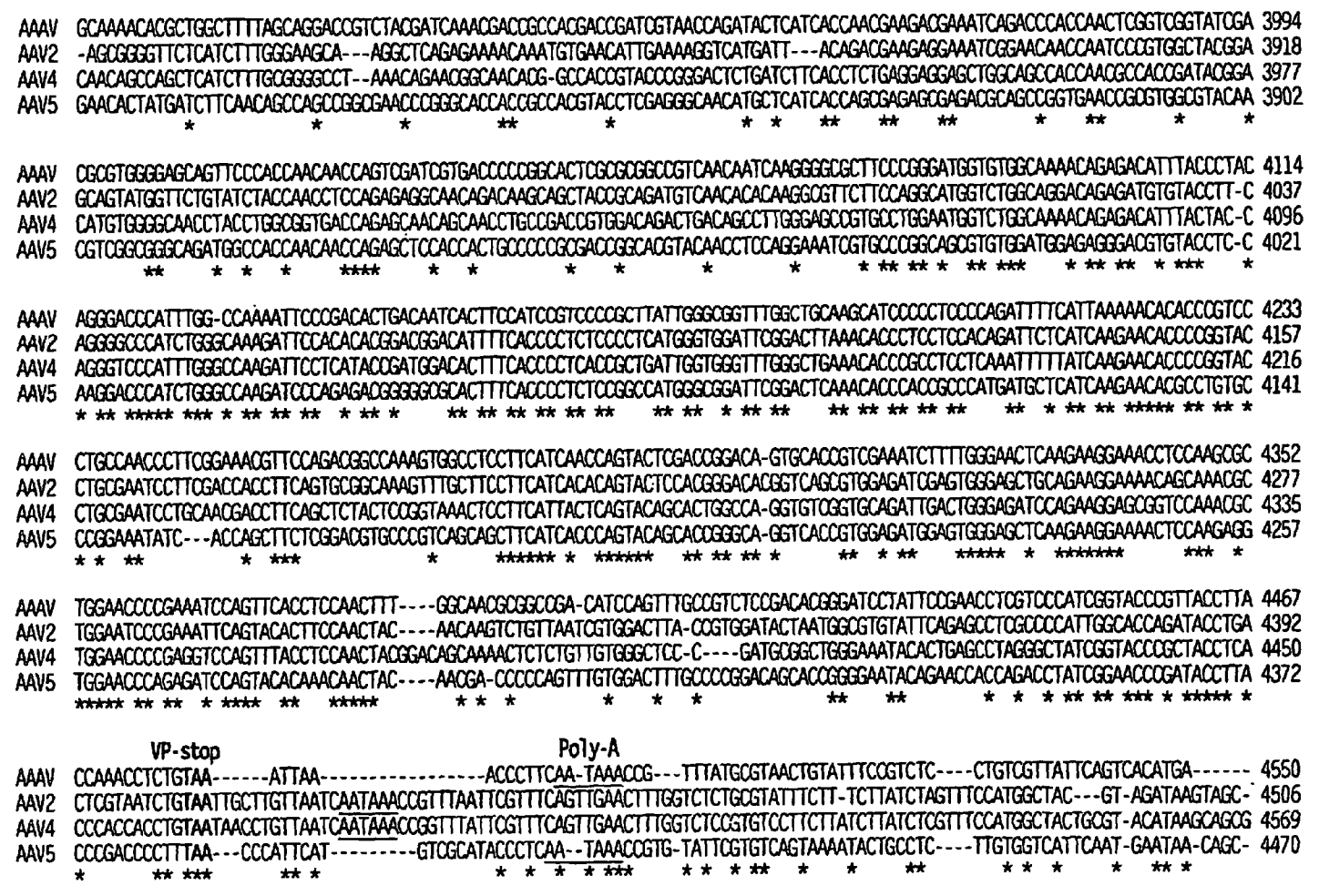
Figure 3H:
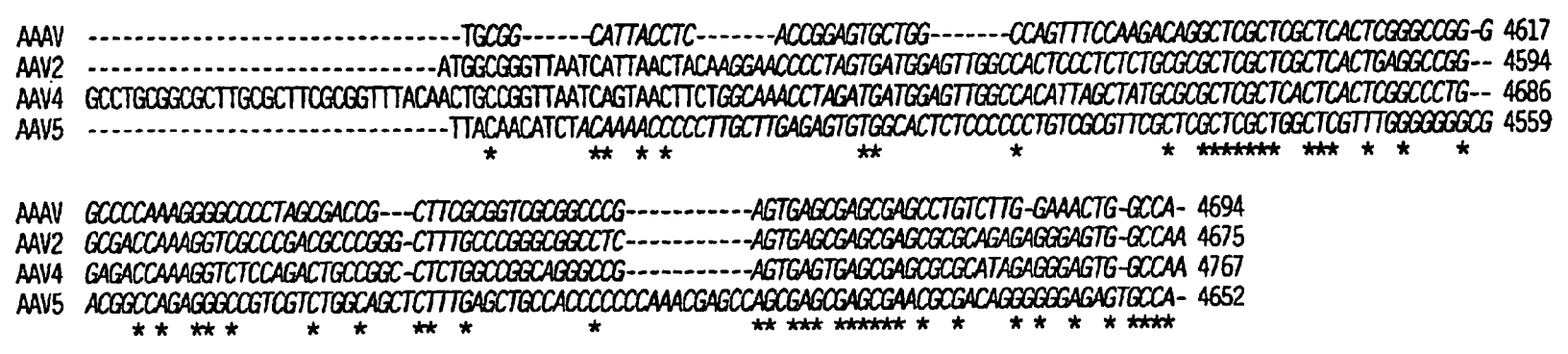

The AAAV ITR is composed of 142 nucleotides with the first 122 forming the characteristic T-shaped palindromic structure (FIG. 3), and it is 60-62% homologous with the ITRs of serotypes 2, 3, 4, and 6 and 48% homologous with AAV5. A tandem repeat of GAGY in the ITR, which serves as the binding element of Rep78 and Rep68 (RBE), is conserved between AAAV and the other AAVs (FIG. 3,4). The trs recognition motif of serotypes 2, 3, 4 and 6 (CCGGT'TG) is highly homologous with that of the putative AAAV trs (CCGGT'CG) and weekly homologous with AAV5 trs site (ACGGT'GT). In addition, the spacing between the RBE and the putative trs is similar to that found in other serotypes, a characteristic that has been shown to be essential for Rep activity (12).

It has been proposed that a potential inverted repeat flanking the core trs sequence of AAV serotypes might be required for Rep trs nicking (11). Such an inverted repeat is not found around the AAAV trs sequence. This observation may indicate that Avian Rep nicking does not require any secondary structure around the core trs element. Methylation interference experiments have indicated the importance of the CTTTG motif found at the tip of one palindrome in AAV2 Rep binding (57). Most of this motif is conserved in AAAV ITR (CTTCG) and only one T residues is changed to C. Interestingly, the AAV4 ITR has a similar substitution in this motif (CTCTG). Thus, irrespectively of the overall nucleotide sequence homology, the secondary structure and the elements required for viral replication are conserved in the AAAV ITR.

The entire AAAV genome (FIG. 3) is 4,694 nucleotides in length and has similar organization with that of other AAVs. It has two inverted terminal repeats and two distinct ORFs. The entire genome of AAAV displays 56-65% identity at the nucleotide level with the other known AAVs. The p5 promoter region of AAAV is much shorter and shows some divergence from homologous regions of other AAV serotypes. Core regulatory elements such as the TATAA box and Ebox/USF are conserved, however YY1 and Rep binding sites are not present. This suggests that AAAV gene expression might be regulated differently from that of other AAVs. The p19 promoter, the p40 promoter, and poly(A) can also be identified in the AAAV genome by homology to those in primate AAV serotypes. Based on the general organization and sequence, these elements are highly conserved.

Figure 4A:
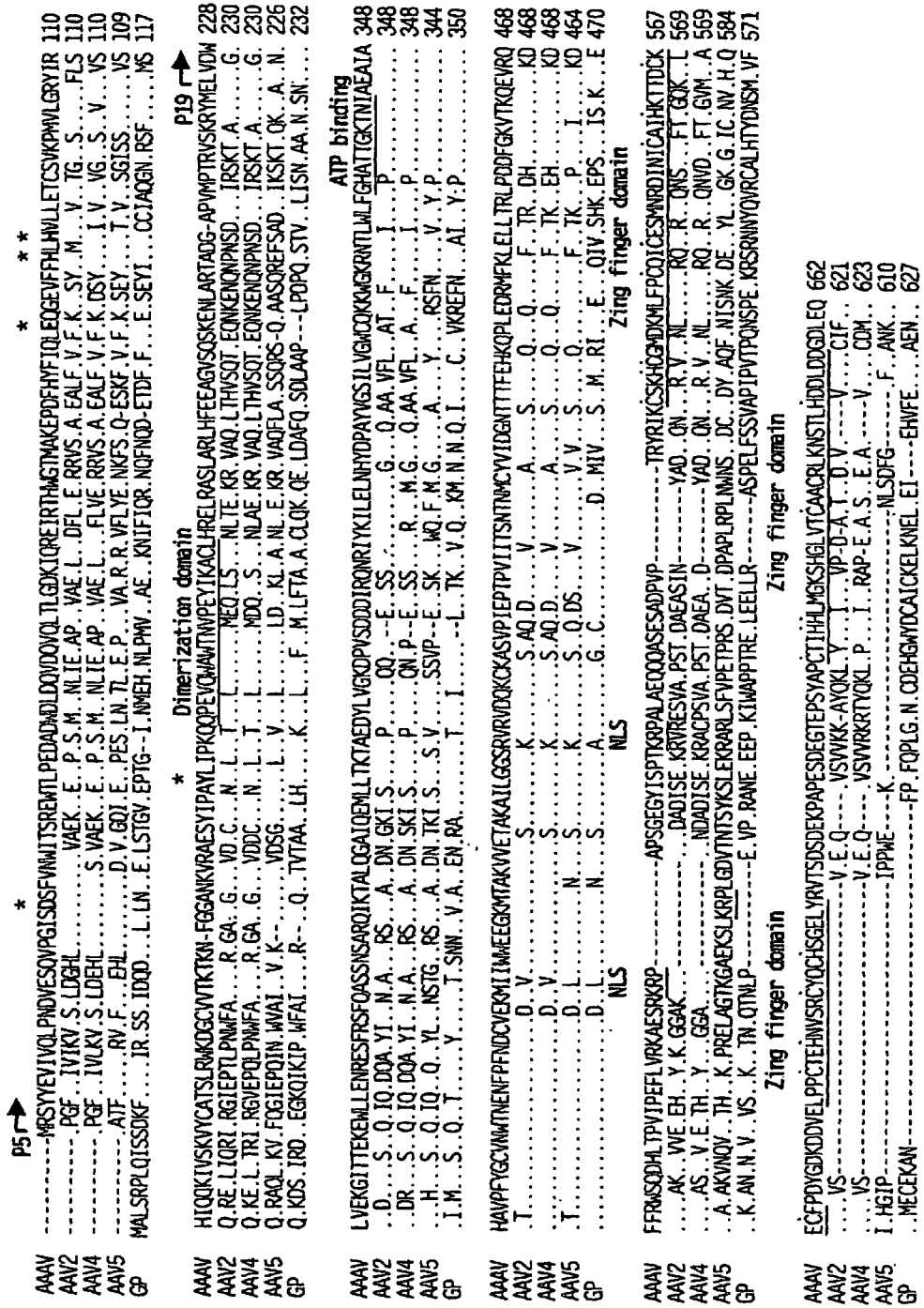

Clustal W protein sequence alignment indicate the left ORF of AAAV is 46-54% identical and equally divergent from that of the primate AAVs and the GPV Rep ORF (FIG. 4a) and only 18-22% identical with the Rep ORF of other mammalian autonomous parvovirus. In comparison, the Rep ORF of isolates 1, 2, 3, 4, 6, 7 and 8 are greater than 90% similar and approximately 67-70% identical with that of AAV5 Rep ORF. The central region of the AAAV Rep ORF (aa 322 to 470), which is present in all Rep proteins, displays the greatest identity (82%) with the same region of the other AAVs and the GPV. This region of the Rep proteins is necessary for ATPase and helicase activity and contains an ATP-binding site (aa 334 to 349) and a divalent cation binding site at amino acid residue 421 (44, 61, 65). The amino terminus (aa 1 to 251) is 42-45% similar between AAAV and the other AAVs. This region of the Rep78 and Rep68 proteins is required for DNA binding and trs endonuclease activities (22, 50). A tyrosine residue at 155 is homologous to the Tyr156 in AAV2 that functions as the active nucleophile in the trs endonuclease site (22, 62). The active site is assembled by the spatial convergence of a divalent metal ion that is tetrahedrally coordinated by Asp24, Glu83, His90 and His92. In addition Glu6 is required for the correct orientation of the two active sites imidazoles from His90 and His92 (31). All of these amino acid residues are strictly conserved among AAV serotypes including AAAV. Furthermore, a helix region important for Rep multimerization (aa 159-179) is also conserved in AAAV. The carboxyl terminal portion (aa 490-662) of the unspliced AAAV Rep proteins appears highly divergent, displaying less than 15% homology with the primate serotypes. However, a characteristic Zinc finger motif was identified using the BLIMPS algorithm. This feature is conserved in all AAV serotypes.

Figure 4B:
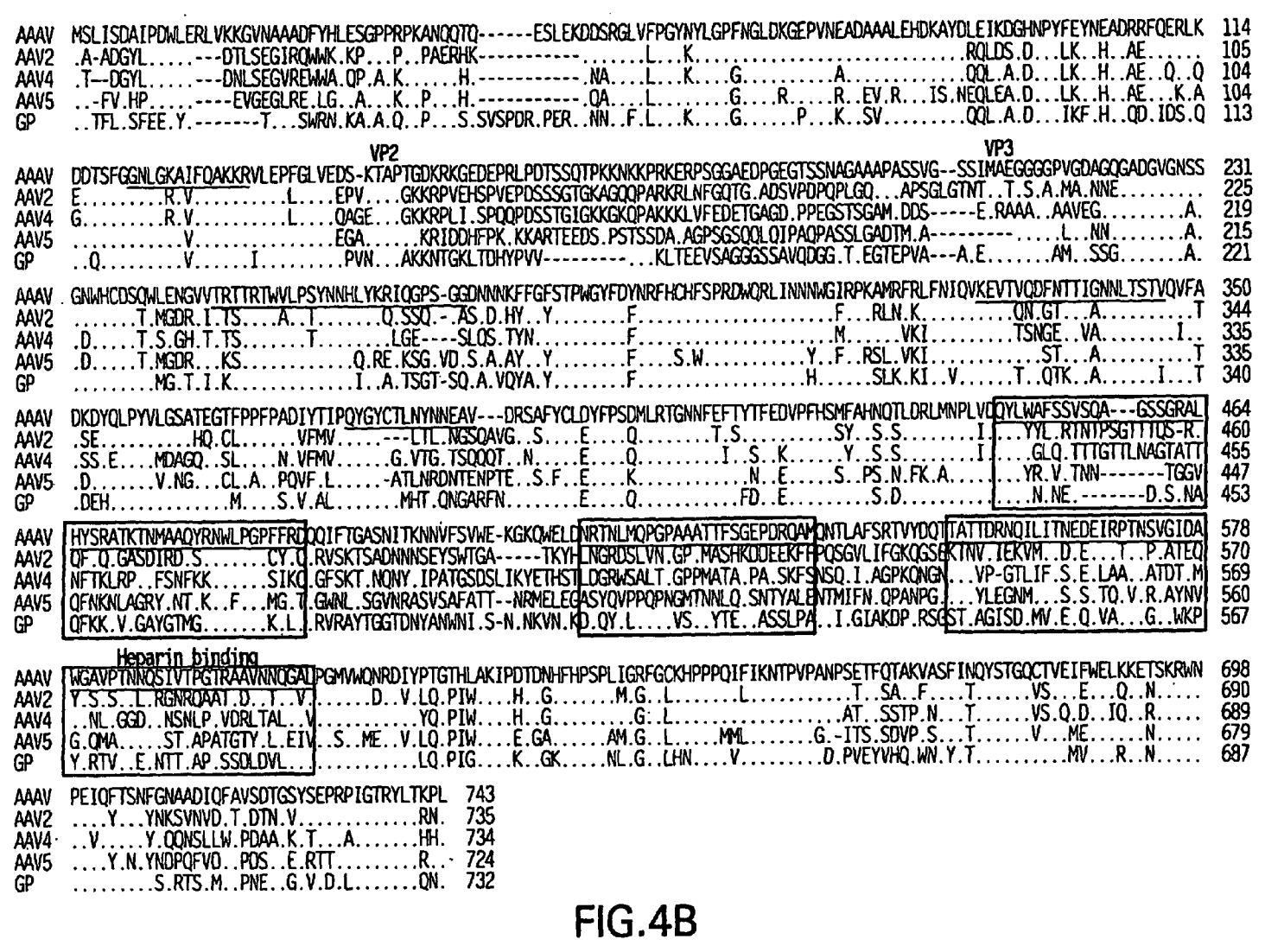

The right ORF of AAAV, which encodes the three viral capsid proteins, is approximately 54-57% identical to the capsid ORF of the other AAVs and the GPV (FIG. 4b). It has been previously reported (6) that the AAAV capsid proteins VP1, VP2 and VP3 have apparent molecular weights of 92, 69 and 61 kDa, respectively, as determined by SDS-PAGE. The calculated molecular masses based on amino acid composition for VP1, VP2 and VP3 are 83, 67 and 60 kDa. We also subjected purified AAAV virions to SDS-PAGE and found that they have MW 91, 68 and 60 kDa (data not shown). As with the primate AAVs and the goose and duck autonomous parvoviruses, the AAAV cap gene contains two ATG initiator codons, one for VP1 and the other for VP3. The unusual ACG initiator codon for VP2 is also conserved in AAAV.

Clustal W alignment of the VP ORFs indicated the presence of conserved and divergent regions. The N terminus of VP1 (aa 1-143), which is required for particle formation, is relatively conserved among AAAV, AAV2, AAV4, AAV5 and GPV. However, the start site for VP2 and VP3 are found in a divergent region. Based on the published three-dimensional structure of the canine parvovirus and comparisons of parvovirus capsid sequences (15), most of the divergent regions among AAAV, AAV2, AAV4 and AAV5 and GPV are located on the exterior of the virus, thus suggesting different uptake mechanisms and altered tissue tropism.

Figure 5A:
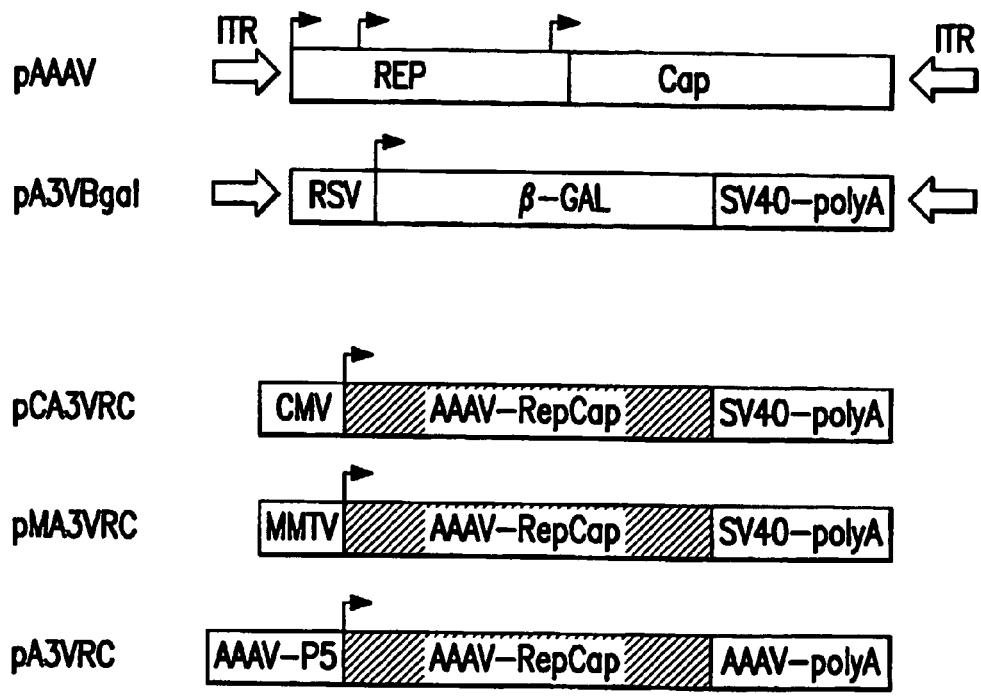
FIGS. 5A and 5B show vector constructs for generation of recombinant AAAV virus and transduction of chicken fibroblasts. A) Wild type AAAV, vector plasmid (pA3Vbgal) and production yields of rAAAV using helper plasmids providing the rep gene under control of CMV, MMTV or the native P5 promoter. The helper plasmids pCA3VRC, pMA3VRC, pA3VRC were individually co-transfected with pA3Vbgal and an adenovirus helper plasmid in 293T cells and rAAAV was produced as described in Material and Methods. The number of rAAAV genomes produced in each group was determined by quantitative PCR and is expressed as DNAse resistant particle/cell (DPN/cell). ITR: inverted terminal repeats from AAAV, RSV: Rous Sarcoma virus long terminal repeat promoter, CMV: cytomegalovirus immediate early promoter, MMTV murine leukemia virus long terminal repeat promoter, β-Gal: β-galactosidase gene, SV40-polyA: polyadenylation signal from SV40. B) Relative transduction efficiency of primary chicken embryonic fibroblasts (CEF) and immortalized chicken embryonic fibroblasts (DF1) with equal particles of rAAAV expressing LacZ.

In the present study, recombinant AAAV particles containing the gene for nuclear localized β-galactosidase were constructed. Virus was produced as previously described (19, 20) by constructing a vector plasmid containing the β-galactosidase gene under control of an RSV promoter flanked by AAAV ITRs (pA3Vβgal, FIG. 5a), and a helper plasmid containing the AAAV rep and cap genes. Virus was isolated from 293T cell lysates by CsCl banding, and the distribution of recombinant virus across the gradient was determined by QPCR analysis of gradient fractions. The majority of packaged genomes were found in fractions with a density of 1.42 g/cm$^3$, which is similar to that of wt AAAV. We also examined the yield of rAAAV when using helper plasmids with the rep gene under control of three different promoters, CMV, MMTV or the native P5 promoter (FIG. 5a). The different helper plasmids (pCA3VRC, pMA3VRC, pA3VRC) were co-transfected with pA3Vbgal and an adenovirus helper plasmid in 293T cells and rAAAV was purified from the three different CVLs using CsCl gradients. The number of rAAAV genomes was determined by QPCR. In three independent trials, the yield of rAAAV was 5-fold and 15-fold greater using the stronger CMV promoter compared with the MMTV and the native P5 promoter, respectively (FIG. 5a). This finding with rAAAV is in contrast to previous work with AAV2 that demonstrated the use of a CMV promoter inhibited the production of rAAV2 (39).

In preliminary studies, it was observed that the addition of detergents during virus purification affected infectivity. To better understand the effect of detergents, we prepared rAAAV in the presence of the following conditions: 0.5% deoxycholate, 0.5% CHAPS, 0.5% octylglucoside (OCG) or no detergent, respectively. The virus from the four groups was purified using CsCl gradients and rAAAV genomes were quantitated using quantitative PCR. No effect was observed on yield of viral particles or density of rAAAV in the four preparations. After dialysis against PBS, transduction efficiency was measured by titration on CEF cells. Addition of OCG or CHAPS had no significant effect on transduction efficiency. However, deoxycholate which is a stronger ionic detergent reduced transduction efficiency almost 10-fold.

Tissue tropism of rAAAV was determined in CEF, DF1, LMH, DT-90, QNR, QT6, 293T, COS, primary chicken embryonic kidney cells, primary chicken pituitary cells and primary human fibroblasts and compared with that of rAAV2, rAAV4 and rAAV5 (Table 1). Table 1 shows the titers for rAAAV, rAAV2, rAAV4 and rAAV5 expressing LacZ in avian and mammalian cell lines and primary cells. Transductions were performed as described in Methods and Materials and efficiency was expressed as transducing units per 10$^6$ recombinant particles.

Figure 5B:
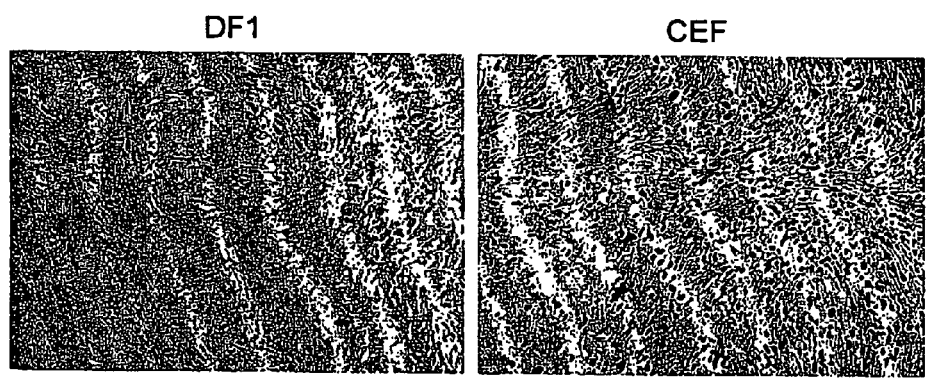

Transduction efficiency of rAAAV was 10-300 fold higher in avian cells compared with that of rAAV2, rAAV4 and rAAV5. In contrast, transduction of the mammalian cells in the panel by rAAAV was almost absent. This observation suggests that AAAV is using a different uptake or transduction mechanism compared with the primate AAVs. Interestingly, rAAAV exhibited ~15-fold higher transduction efficiency in primary chicken embryonic fibroblasts compared to immortalized embryonic fibroblasts (FIG. 5B).

The present invention also showed that AAAV ITR can function as a universal ITR for packaging with AAV2, 5 Rep proteins. Cross packaging experiments were carried out by transducing 293T cells with the two production plasmids (an ITR containing plasmid and a RepCap production plasmid) indicate and a third helper plasmid to supply adenovirus function. Forty-eight hours post transfection, cells were harvested and the amount of DNAse resistance virus measured by quantitative PCR.

TABLE 1

| | Transducing units per 10$^6$ genomes | | | |
|---|---|---|---|---|
| Cell type | rAAAV | rAAV2 | rAAV4 | rAAV5 |
| CEF | 7140 ± 380 | 25 ± 3.5 | 84 ± 6.3 | 58 ± 5.7 |
| DF-1 | 530 ± 35 | 8 ± 0.9 | 45 ± 4.7 | 60 ± 6.1 |
| LMH | 2380 ± 145 | 230 ± 25 | 34 ± 5.6 | 40 ± 4.9 |
| DT-90 | ND | ND | ND | ND |
| QNR | 1260 ± 90 | 176 ± 18 | 42 ± 5.2 | 185 ± 26 |
| QT6 | 930 ± 62 | 112 ± 21 | 23 ± 3.8 | 33 ± 5 |
| Chicken Primary Embryonic Kidney cells | 8080 ± 560 | 422 ± 46 | 350 ± 40 | 235 ± 38 |
| Chicken Primary pituitary cells | 4640 ± 375 | 144 ± 17 | 70 ± 12 | 91 ± 8.4 |
| 293T | ND | 4500 ± 355 | 3130 ± 270 | 684 ± 57 |
| COS | 5 ± 0.7 | 6920 ± 420 | 3550 ± 165 | 592 ± 53 |
| A549 | ND | 2190 ± 315 | 1360 ± 140 | 26 ± 4.3 |
| Humary primary fibroblasts | ND | 1990 ± 170 | 1130 ± 145 | 292 ± 31 |

Numbers represent the mean ± standard error from four independent transduction assays.
ND = none detected.

Characterization of Binding and Transduction

The characterization of the binding and transduction requirements is important for the optimal utilization of a vector. Therefore we have examined the binding and transduction requirements of avian AAV (AAAV). To date, primate AAVs have been shown to require cell surface expression of either heparin sulfate proteoglycans (HSPG) (AAV2, 3) or sialic acid (AAV4, 5) for virus binding and attachment. However our studies with avian AAV indicate that neither is required. Surprisingly, AAAV required a distinct form of glycosylation, terminal lactose, for efficient binding and transduction, which is unique a distinct from that of the primate AAVs.

Figure 6:
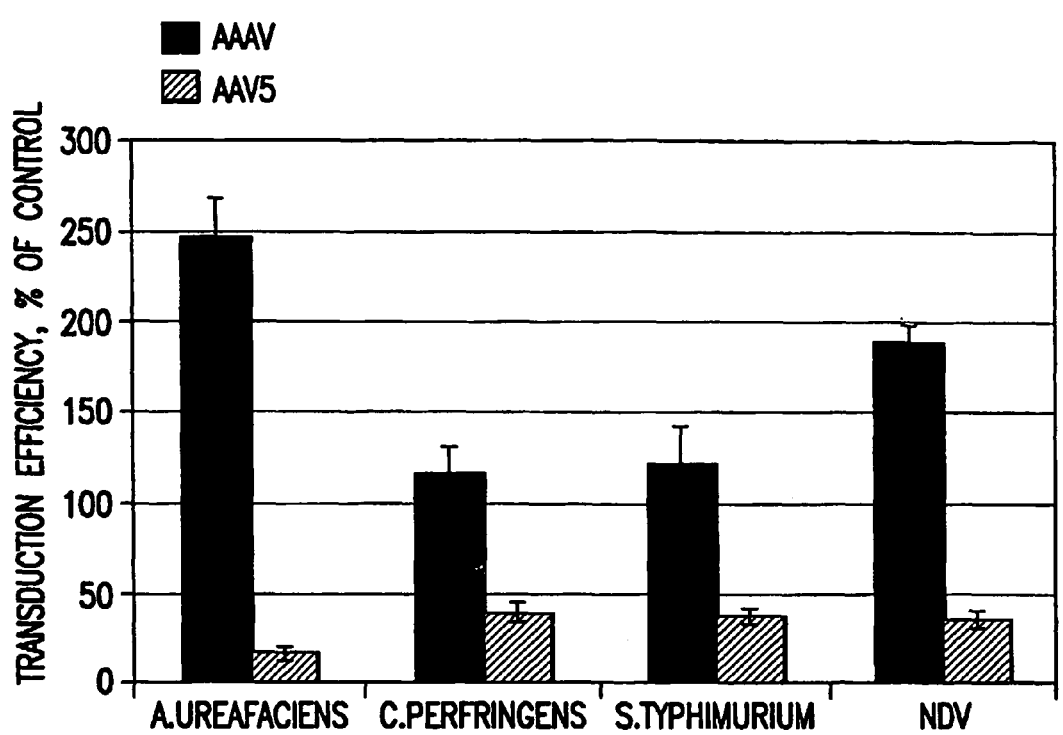
FIG. 6 shows results with neuraminidase indicating that while AAV5 is sensitive to sialic acid treatment AAAV is not.
Figure 7:
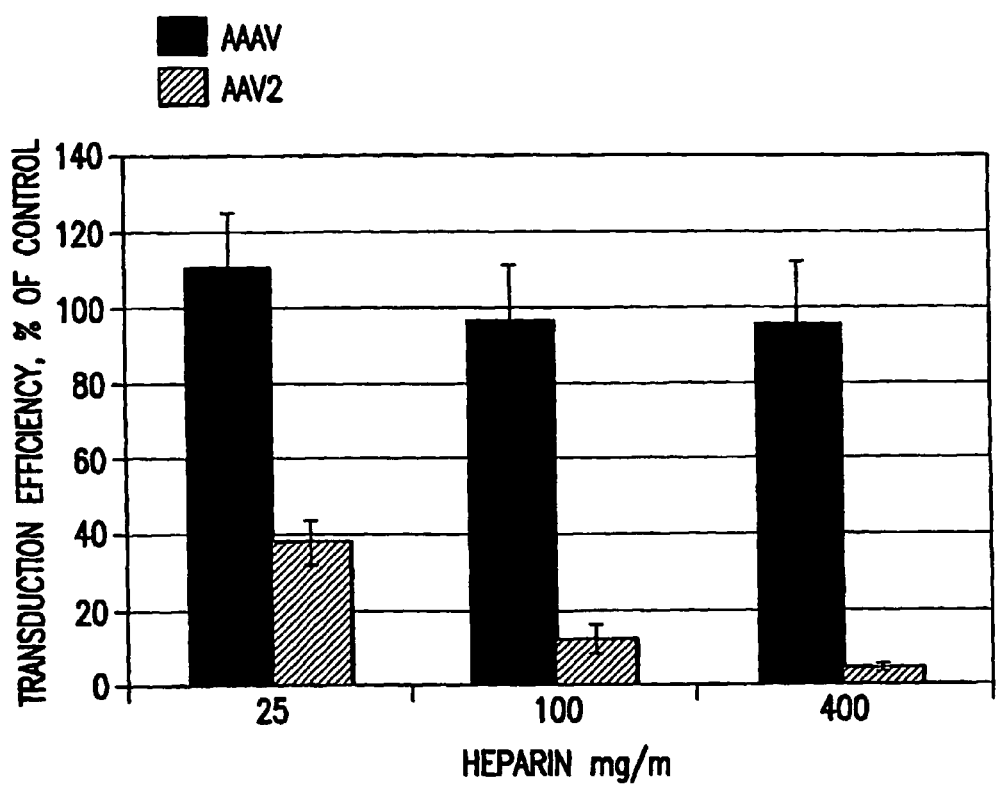
FIG. 7 shows that while AAV2 is sensitive to heparin competition, AAAV is not.
Figure 8:
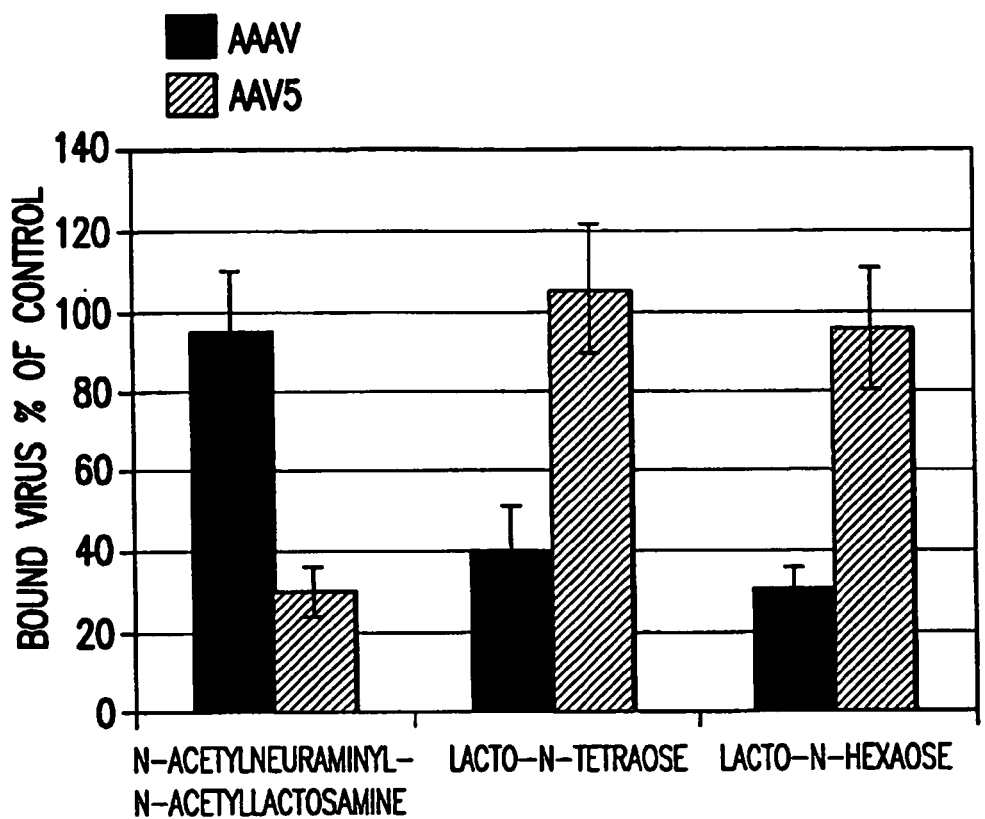
FIG. 8 shows the role of terminal lactose in AAAV binding by incubating virus with different conjugates that had either terminal lactose or sialic acid. AAV5 is sensitive to competition with sialic acid conjugates but AAAV is not. However AAAV is competed by terminal lactose conjugates confirming ERCR lectin result.
Figure 9A:
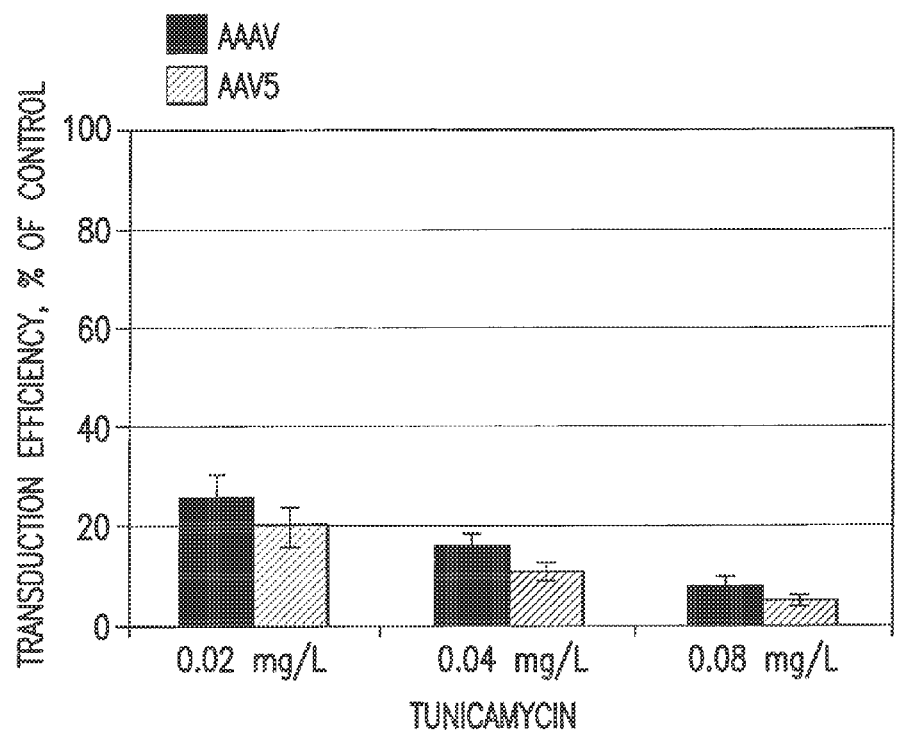
FIGS. 9A and 9B show that treatment with tunicamycin blocks virus binding and transduction, suggesting that glycosylation is N-linked. AAV5 is the control.
Figure 9B:
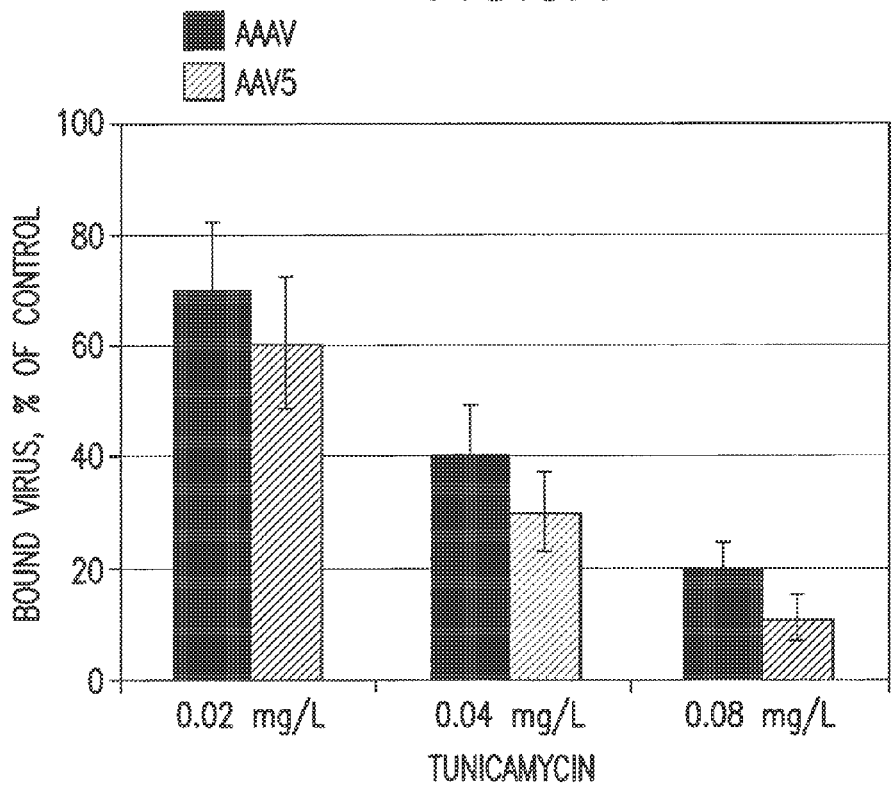
Figure 11A:
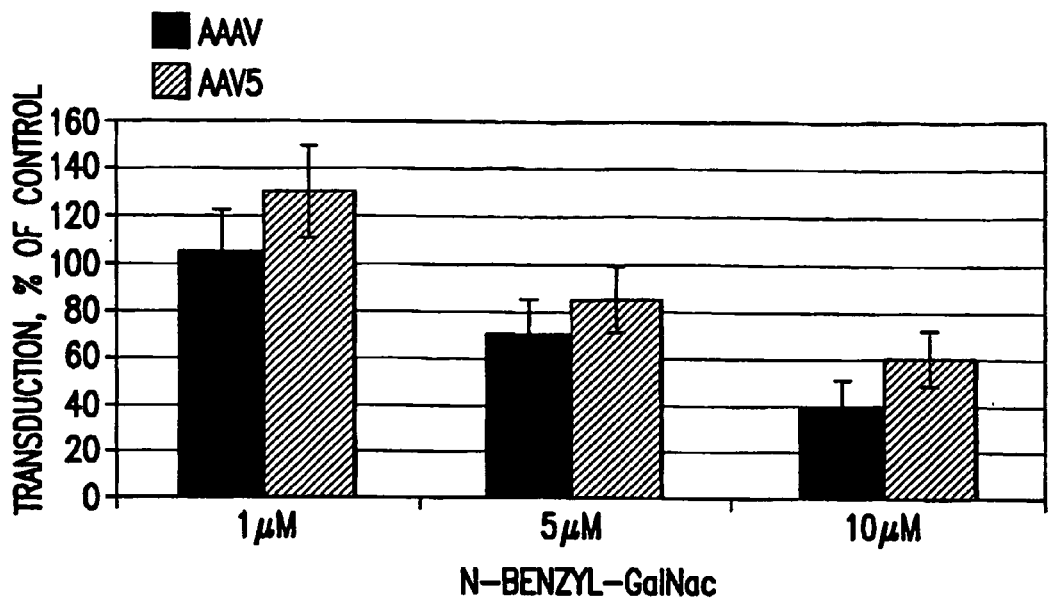
FIGS. 11A and 11B show that the linkage is probably not an O-linkage.
Figure 11B:
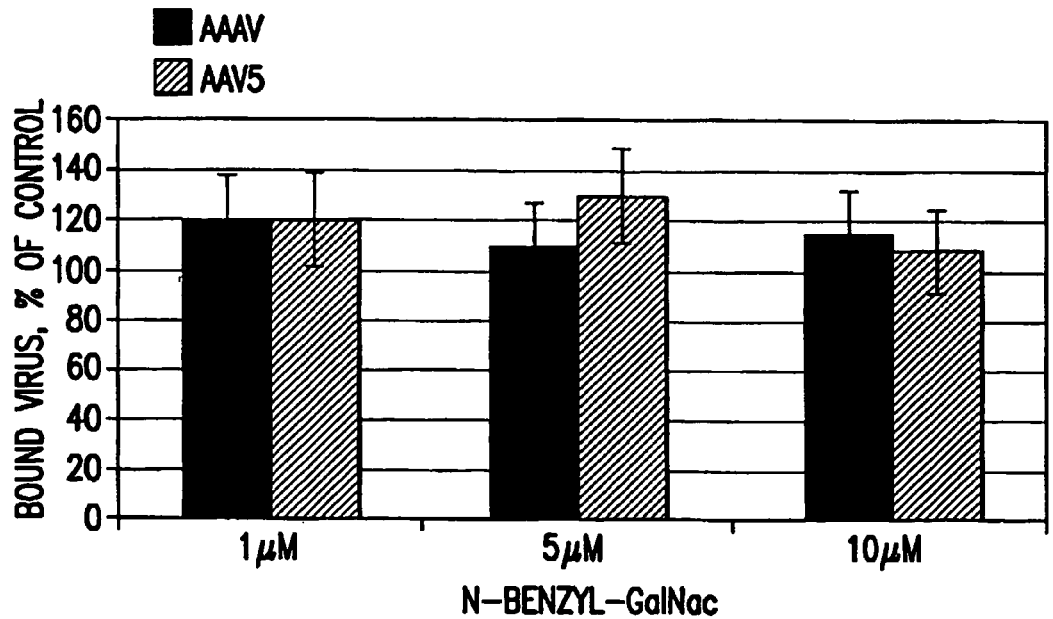

Initial experiments with AAAV demonstrated that transduction is insensitive to competition with soluble heparin, which blocks binding with HSPG, soluble sialoconjugates, which blocks binding with sialic acid, or treatment with neuraminidase, which removes cell surface sialic acid (FIGS. 7, 8 and 6, respectively). Thus, Avian AAV appeared to be requiring a unique cell surface epitope. To characterize this epitope we treated DF-1 cells with several different inhibitors of glycosylation. Treatment with tunicamycin, which inhibits N-linked glycosylation, blocked both virus binding and transduction. In contrast, treatment with the O-linked inhibitor N-benzyl gal NAc had no effect (FIGS. 9 and 11, respectively).

Figure 12A:
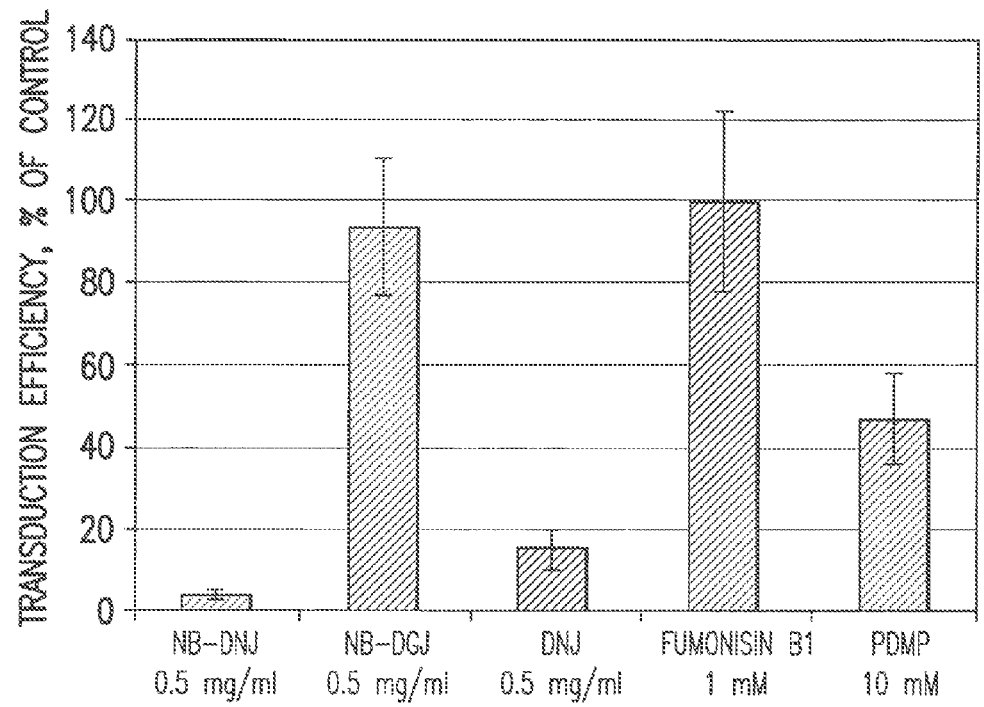
FIGS. 12A and 12B show results with a series of N-linked inhibitors: NB-DNJ is a specific inhibitor of ER glucosidase I, II, and glycolipid; NB-DGJ glycolipid synthesis inhibiting properties as NB-DNJ; DNJ inhibits glucosidase 1,2; Fumonisin B1 is an inhibitor of ceramide synthesis; and PDMP is an inhibitor of glycosphingolipid synthesis.
Figure 12B:
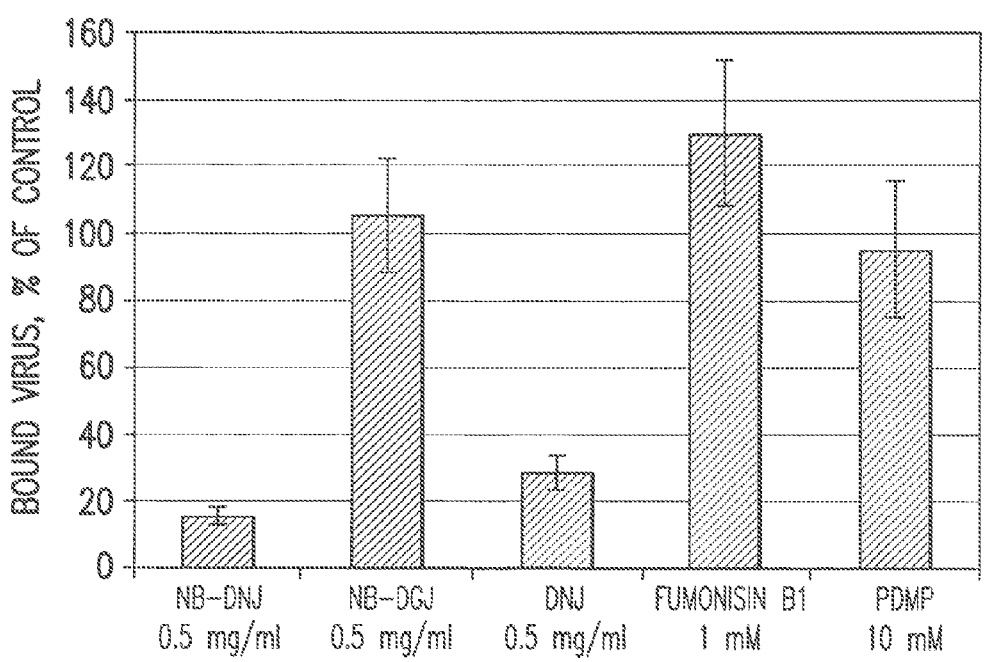

Similar results were obtained with other N-linked inhibitors including N-butyl deoxynojirimycin and the unmodified form deoxynojirimycin. PDMP and Fumonisin B1, which inhibit the glycosylation of sphingolipids and ceramides, had no effect on AAAV binding or transduction suggesting that the carbohydrate necessary for binding was attached to a protein (FIG. 12). Lack of inhibition by Fumonisin B1 and PDMP and DGJ suggest lipids are not involved, but inhibition of binding and transduction with NB-DNJ and DNJ suggests glycoprotein is involved.

Figure 10:
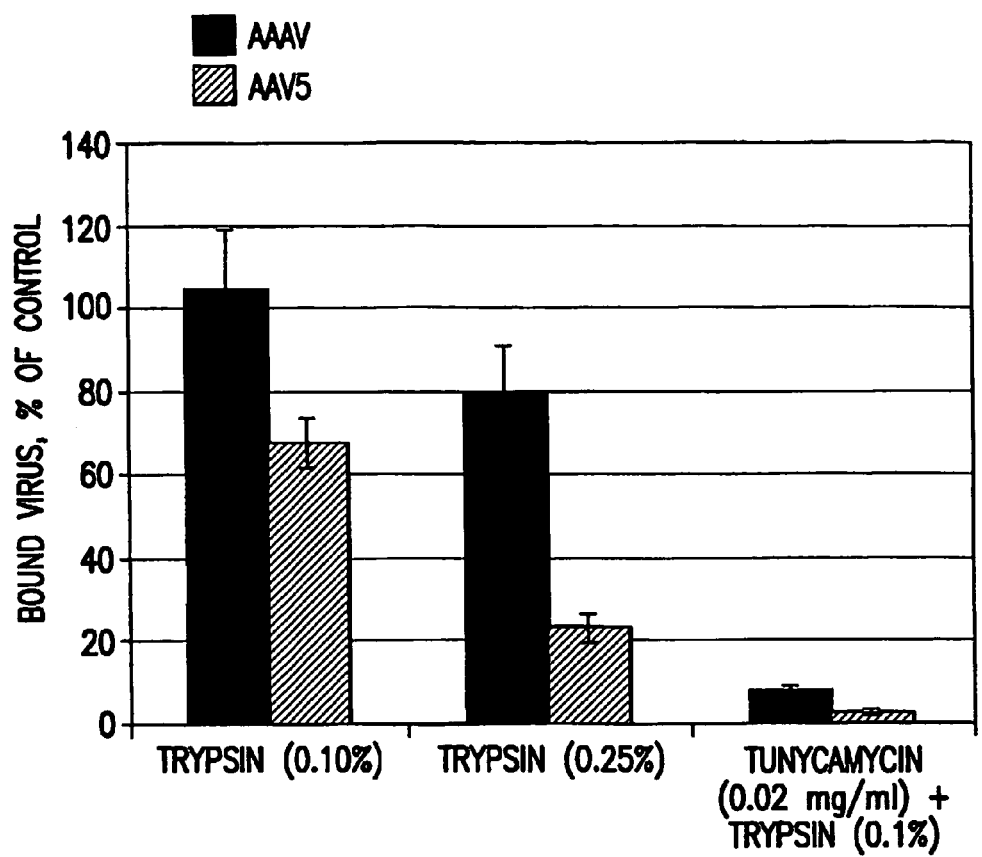
FIG. 10 confirms that glycoprotein is involved in AAAV binding and transduction, cells were treated with broad specificity protease, trypsin. Like AAV5, trypsin minimally effects virus binding. However treatment with low levels of tunicamycin dramatically increased the inhibition in binding observed with trypsin treatment.

Initial experiments to block transduction by treatment with the protease trypsin had no effect on transduction (FIG. 10). While trypsin is considered a broad specificity protease, its activity can be blocked by glycosylation; therefore we tested trypsin treatment after incubating the cells with low levels of tunicamycin which did not effectively block transduction. Treatment with trypsin or low levels of tunicamycin alone inhibited 0% or 25% of AAAV transduction respectively. However, the combination of the two inhibited greater than 90% of AAAV transduction confirming that AAAV required the presence of a N-linked glycoprotein for efficient transduction (FIG. 10).

Figure 13A:
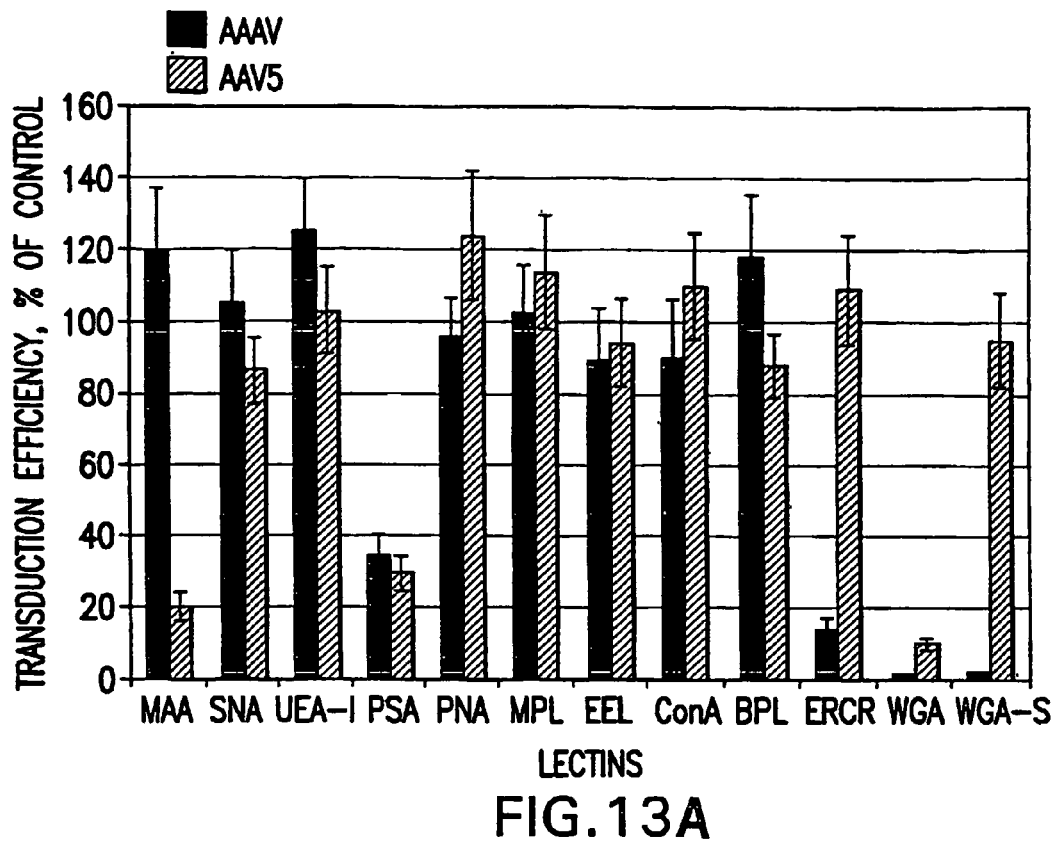
FIGS. 13A and 13B show results using several lectins and confirms previous results that sialic acid is not important (WGA vs WGA-s). *Erythrina corralodendron* (ERCL) which binds terminal poly lactose does inhibit suggesting that the virus is binding terminal lactose.
Figure 13B:
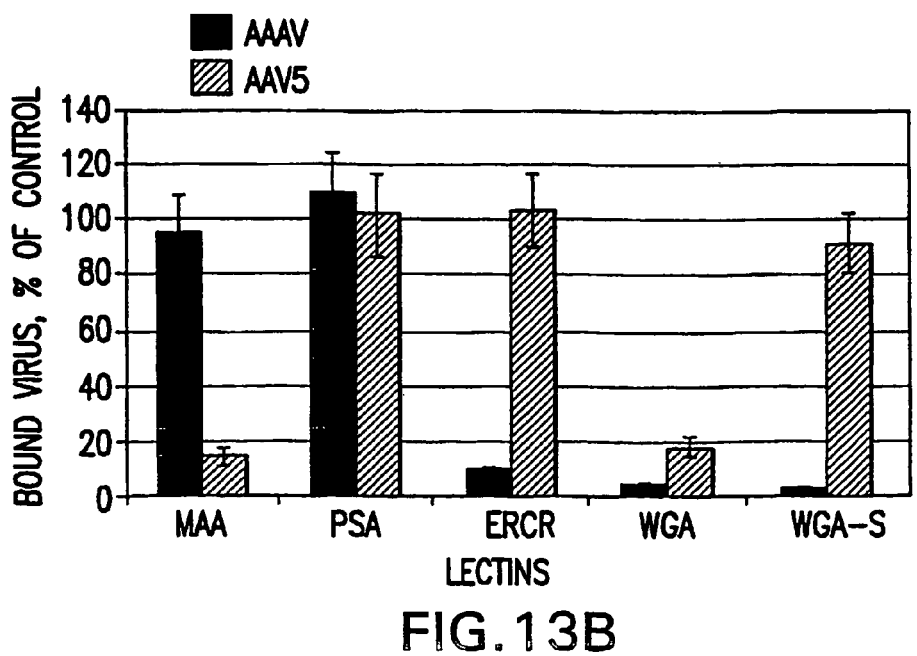

To further identify the carbohydrate component we tested a series of lectins for the ability to block virus binding and transduction (FIG. 13). These lectins are briefly described as follows:

MAA—This lectin binds glycoconjugates having galactosyl (b-1,4) N-acetylglucosamine structures. *Maackia amurensis* lectin I seems to tolerate substitution of N-acetyllactosamine with sialic acid at the 3 position of galactose;

SNA—*Sambucus nigra* lectin binds preferentially to sialic acid attached to terminal galactose in (a-2,6), and to a lesser degree, (a-2,3), linkage;

UEA-I—UEA I binds to many glycoproteins and glycolipids containing a-linked fucose residues;

PSA—This lectin has specificity toward a-linked mannose-containing oligosaccharides, with an N-acetylchitobiose-linked a-fucose residue included in the receptor sequence;

PHA-P—This lectin binds to complex carbohydrate structures on the cell surface;

MPL—This lectin prefers alpha linked N-acetylgalactosamine structures;

EEL—This lectin has a carbohydrate binding specificity toward type I or type 2 chain blood group B structures but will bind other oligosaccharides containing galactosyl (a-1,3) galactose;

Con A—recognizes a commonly occurring sugar structure, a-linked mannose;

BPL—Binding appears to be highest for glycoconjugates containing galactosyl (b-1,3) N-acetylgalactosamine structures but oligosaccharides with a terminal alpha linked N-acetylgalactosamine can also bind;

ERCL—*Erythrina* corallodendron has an affinity for N-acetyllactosamine, N-acetyl-D-galactosamine, lactose and D-galactose;

WGA—The receptor sugar for WGA is N-acetylglucosamine, with preferential binding to dimers and trimers of this sugar. WGA can bind oligosaccharides containing terminal N-acetylglucosamine or chitobiose, structures which are common to many serum and membrane glycoproteins; and WGA-s succinylated wheat germ agglutinin does not bind to sialic acid residues, unlike the native form, but retains its specificity toward N-acetylglucosamine (Eur. J. Biochem. 98, 39, 1979 and Eur. J. Biochem. 104, 147, 1980).

In agreement with the neuraminidase data, lectins MAA and SNA, which bind sialic acid, had no effect on AAAV binding or transduction (FIG. 13). Furthermore, both WGA and the succinylated form, which does not bind sialic acid, both inhibited AAAV binding and transduction in agreement with the MAA and SNA data. Binding and transduction were also inhibited by *Erythrina corralodendron* lectin which binds terminal poly lactose, suggesting that AAAV may bind this carbohydrate complex. To test this hypothesis, competition experiments were carried out with soluble sialolactose conjugates or lactose complexes alone. While AAAV was inhibited by the terminal lactose conjugates, AAV5 was not, confirming the results of the lectin blocking experiments (FIG. 8).

Taken together, these results indicate that AAAV requires N-linked terminal lactose present on cell surface proteins for efficient binding and entry. While other proteins may be involved in transduction, terminal lactose should be considered as a co-receptor for AAAV binding and entry. This finding was completely unexpected and very different from that of primate AAVs.

Based on this data, the use of lactose affinity chromatography (e.g., columns) for the purification of AAAV is provided. An example of lactose affinity chromatography is described by Tasumi et al., Primary structure and characteristics of a lectin from skin mucus of the Japanese eel *Anguilla japonica*, J Biol. Chem. 2002 Jul. 26; 277(30):27305-11 (which is incorporated herein by reference).

Throughout this application, various publications are referenced. The disclosures of these publications in their entireties are hereby incorporated by reference into this application in order to more fully describe the state of the art to which this invention pertains.

REFERENCES

1. Arella, M., S. Garzon, J. Bergeron, and P. Tijssen. *Handbook of Parvoviruses*. Vol. 1. ed. P. Tijssen. Boca Raton, Fla., CRC Press, 1990.
2. Bachmann, P. A., M. D. Hoggan, E. Kurstak, J. L. Melnick, H. G. Pereira, P. Tattersall, and C. Vago. 1979. Interverology 11: 248-254.
3. Bantel-Schaal, U. and M. Stohr. 1992. J. Virol. 66: 773-779.
4. Chang, L. S., Y. Shi, and T. Shenk. 1989. J. Virol. 63: 3479-88.
5. Chejanovsky, N. and B. J. Carter. 1989. Virology 173: 120-128.

6. Chejanovsky, N. and B. J. Carter. 1989. Virology 171: 239-247.
7. Chiorini, J. A., S. M. Wiener, R. M. Kotin, R. A. Owens, SRM Kyöstiö, and B. Safer. 1994. J. Virol. 68: 7448-7457.
8. Chiorini, J. A., M. D. Weitzman, R. A. Owens, E. Urcelay, B. Safer, and R. M. Kotin. 1994. J. Virol. 68: 797-804.
9. Chiorini, J. A., C. M. Wendtner, E. Urcelay, B. Safer, M. Hallek, and R. M. Kotin. 1995. Human Gene Therapy 6: 1531-1541.
10. Chiorini, J. A., L. Yang, B. Safer, and R. M. Kotin. 1995. J. Virol. 69: 7334-7338.
11. Dixit, M., M. S. Webb, W. C. Smart, and S. Ohi. 1991: Gene 104: 253-7.
12. Fisher, R. E. and H. D. Mayor. 1991. J Theor Biol 149: 429-39.
13. Flotte, T. R., S. A. Aflone, C. Conrad, S. A. McGrath, R. Solow, H. Oka, P. L. Zeitlin, W. B. Guggino, and B. J. Carter. 1993. Proc. Natl. Acad. Sci. 90: 10613-10617.
14. Flotte, T. R., S. A. Afione, R. Solow, M. L. Drumm, D. Markakis, W. B. Guggino, P. L. Zeitlin, and B. J. Carter. 1993. J Biol Chem 268: 3781-90.
15. Hermonat, P. L., M. A. Labow, R. Wright, K. I. Berns, and N. Muzyczka. 1984. J. Virol. 51: 329-339.
16. Hermonat, P. L. and N. Muzyczka. 1984. Proc Natl Acad Sci USA 81: 6466-70.
17. Hunter, L. A. and R. J. Samulski. 1992. J. Virol. 66: 317-24.
18. Ito, M. and H. D. Mayor. 1968. J. Immuno. 100: 61-68.
19. Janik, J. E., M. M. Huston, K. Cho, and J. A. Rose. 1989. Virology 168: 320-9.
20. Kaplitt, M. G., P. Leone, R. J. Samulski, X. Xiao, D. W. Pfaff, K. L. O'Malley, and J. M. During. 1994. Nature Genetics 8: 148-154.
21. Kotin, R. M., M. Siniscalco, R. J. Samulski, X. Zhu, L. Hunter, C. A. Laughlin, S. McLaughlin, N. Muzyczka, M. Rocchi, and K. I. Berns. 1990. Proc. Natl. Acad. Sci. (USA) 87: 2211-2215.
22. Laughlin, C. A., N. Jones, and B. J. Carter. 1982. J. Virol. 41: 868-76.
23. Laughlin, C. A., M. W. Myers, D. L. Risin, B. J. Carter. 1979. Virology 94: 162-74.
24. McCarty, D. M., J. Pereira, I. Zolotukhin, X. Zhou, J. H. Ryan, and N. Muzyczka. 1994. J. Virol. 68: 4988-4997.
25. Mendelson, E., J. P. Trempe, and B. J. Carter. 1986. J. Virol. 60: 823-832.
26. Mizukami, H., N. S. Young, and K. E. Brown. 1996. Virology 217: 124-130.
27. Muster, C. J., Y. S. Lee, J. E. Newbold, and J. Leis. 1980. J. Virol. 35: 653-61.
28. Muzyczka, N. 1992. Curr Top Microbiol Immunol 158: 97-129.
29. Parks, W. P., J. L. Melnick, R. Rongey, and H. D. Mayor. 1967. J. Virol. 1: 171-180.
30. Podsakoff, G., K. K. Jr Wong, and S. Chatterjee. 1994. J. Virol. 68: 5656-5666.
31. Rose, J. A., M. D. Hoggan, F. Koczot, and A. J. Shatkin. 1968. J. Virol. 2: 999-1005.
32. Russell, D. W., A. D. Miller, and I. E. Alexander. 1994. Proc. Natl. Acad. Sci. USA 91: 8915-8919.
33. Ryan, J. H., S. Zolotukhin, and N. Muzyczka. 1996. J. Virol. 70: 1542-1553.
34. Samulski, R. J., K. I. Berns, M. Tan, and N. Muzyczka. 1982. Proc Natl Acad Sci USA 79: 2077-81.
35. Samulski, R. J., L. S. Chang, and T. Shenk. 1989. J. Virol. 63: 3822-8.
36. Sanes, J. R., J. L. R. Rubenstein, and J. F. Nicocas. 1986. EMBO 5: 3133-3142.
37. Senaphthy, P., J. D. Tratschin, and B. J. Carter. 1984. J Mol Biol 179: 1-20.
38. Tratschin, J. D., I. L. Miller, and B. J. Carter. 1984. J. Virol. 51: 611-619.
39. Trempe, J. P. and B. J. Carter. 1988. J. Virol. 62: 68-74.
40. Trempe, J. P., E. Mendelson, and B. J. Carter. 1987. Virology 161: 18-28.
41. Walsh, C. E., J. M. Liu, X. Xiao, N. S. Young, A. W. Nienhuis, and R. J. Samulski. 1992. Proc Natl Acad Sci USA 89: 7257-61.
42. Winocour, E., M. F. Callaham, and E. Huberman. 1988. Virology 167: 393-9.
43. Jaksch, M., K. D. Gerbitz, and C. Kilger. 1995. Clin. Biochem. 28:503-509
44. Burcin, M. M., O'Malley, B. W. and S. Y. Tsai. 1998. Frontiers in Bioscience 3:1-7.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A nucleic acid vector comprising:
   a) a pair of inverted terminal repeats (ITRs), each of which is capable of forming a T-shaped hairpin structure, and wherein at least one inverted terminal repeat (ITR) comprises SEQ ID NO:20 and SEQ ID NO:21; and,
   b) a heterologous nucleic acid sequence between the inverted terminal repeats,
   wherein at least one ITR can be used as an origin of replication.

2. The nucleic acid vector of claim 1, wherein said inverted terminal repeats independently comprise a nucleic acid sequence at least 70% identical to SEQ ID NO:16 or SEQ ID NO:17.

3. The nucleic acid vector of claim 1, wherein said inverted terminal repeats independently comprise a nucleic acid sequence at least 90% identical to SEQ ID NO:16 or SEQ ID NO:17.

4. The nucleic acid vector of claim 1, wherein each of said inverted terminal repeats independently comprises SEQ ID NO: 16 or SEQ ID NO: 17.

5. The nucleic acid vector of claim 1, wherein said heterologous nucleic acid sequence is functionally linked to a promoter.

6. The nucleic acid vector of claim 1, wherein said heterologous nucleic acid sequence is functionally linked to a promoter comprising SEQ ID NO:24.

7. A recombinant AAAV virion comprising
   a) a pair of inverted terminal repeats (ITRs), each of which is capable of forming a T-shaped hairpin structure, and wherein at least one inverted terminal repeat comprises SEQ ID NO:20 and SEQ ID NO:21; and,
   b) a heterologous nucleic acid sequence between the inverted terminal repeats,
   wherein at least one ITR can be used as an origin of replication.

8. The recombinant AAAV virion of claim 7, wherein said inverted terminal repeats independently comprise a nucleic acid sequence at least 70% identical to SEQ ID NO:16 or SEQ ID NO:17.

9. The recombinant AAAV virion of claim 7, wherein said inverted terminal repeats independently comprise a nucleic acid sequence at least 90% identical to SEQ ID NO:16 or SEQ ID NO:17.

10. The recombinant AAAV virion of claim 7, wherein each of said inverted terminal repeats independently comprises SEQ ID NO: 16 or SEQ ID NO: 17.

11. The recombinant AAAV virion of claim 7, wherein said heterologous nucleic acid sequence is functionally linked to a promoter.

12. The recombinant AAAV virion of claim 7, wherein said heterologous nucleic acid sequence is functionally linked to a promoter comprising SEQ ID NO:24.

13. A vector comprising a nucleic acid sequence selected from the group consisting of SEQ ID NO:10, SEQ ID NO:12 and SEQ ID NO:14, wherein the vector is a plasmid, a yeast artificial chromosome or a non-AAV viral vector.

14. A vector that encodes a protein comprising SEQ ID NO:11, SEQ ID NO: 13 or SEQ ID NO: 15, wherein the vector is a plasmid, a yeast artificial chromosome or a non-AAV viral vector.

15. A vector system for producing infectious AAAV particles, said vector system comprising at least one nucleic acid molecule selected from the group consisting of:
   (a) a nucleic acid molecule comprising a pair of inverted terminal repeats (ITRs), each of which is capable of forming a T-shaped hairpin structure, and a heterologous nucleic acid sequence between the inverted terminal repeats, wherein at least one inverted terminal repeat comprises SEQ ID NO:20 and SEQ ID NO:21, and wherein at least one ITR can be used as an origin of replication; and,
   (b) a recombinant nucleic acid molecule that encodes a protein comprising SEQ ID NO:11, SEQ ID NO:13 or SEQ ID NO:15, wherein the recombinant nucleic acid molecule is a plasmid, a yeast artificial chromosome or a non-AAV vector.

16. The vector system of claim 15, wherein said inverted terminal repeats independently comprise a nucleic acid sequence at least 70% identical in sequence to SEQ ID NO: 16 or SEQ ID NO: 17.

17. The vector system of claim 15, wherein said inverted terminal repeats independently comprise a nucleic acid sequence at least 90% identical in sequence to at least one sequence selected from SEQ ID NO:16 and SEQ ID NO:17.

18. The vector system of claim 15, wherein each of said inverted terminal repeats independently comprises SEQ ID NO: 16 or SEQ ID NO: 17.

19. The vector system of claim 15, wherein said heterologous nucleic acid sequence is functionally linked to a promoter.

20. The vector system of claim 15, wherein said encoded protein capable of forming infectious AAAV particles comprises an amino acid sequence selected from the group consisting of SEQ ID NO:11, SEQ ID NO:13 and SEQ ID NO:15.

21. A nucleic acid vector comprising:
   (a) a nucleic acid sequence comprising a pair of inverted terminal repeats (ITRs) flanking a heterologous nucleic acid sequence, each inverted terminal repeat being capable of forming a T-shaped hairpin structure, wherein at least one inverted terminal repeat comprises SEQ ID NO:20 and SEQ ID NO:21, and wherein at least one ITR can be used as an origin of replication;
   (b) a nucleic acid sequence encoding a protein comprising SEQ ID NO:11, SEQ ID NO:13 or SEQ ID NO:15; and
   (c) a nucleic acid sequence encoding a protein comprising an amino acid sequence selected from the group consisting of SEQ ID NO:3, SEQ ID NO:5, SEQ ID NO:7 and SEQ ID NO:9.

* * * * *